US010611850B2

(12) United States Patent
Christian et al.

(10) Patent No.: US 10,611,850 B2
(45) Date of Patent: Apr. 7, 2020

(54) CRYSTALLINE ANTIBODY FORMULATIONS

(71) Applicant: AMGEN INC., Thousand Oaks, CA (US)

(72) Inventors: Twinkle R. Christian, Thousand Oaks, CA (US); Christi L. Clogston, Camarillo, CA (US); Timothy David Osslund, Camarillo, CA (US)

(73) Assignee: Amgen Inc., Thousand Oaks, CA (US)

( * ) Notice: Subject to any disclaimer, the term of this patent is extended or adjusted under 35 U.S.C. 154(b) by 202 days.

(21) Appl. No.: 15/326,316

(22) PCT Filed: Jul. 13, 2015

(86) PCT No.: PCT/US2015/040211
§ 371 (c)(1),
(2) Date: Jan. 13, 2017

(87) PCT Pub. No.: WO2016/010924
PCT Pub. Date: Jan. 21, 2016

(65) Prior Publication Data
US 2017/0198058 A1 Jul. 13, 2017

Related U.S. Application Data

(60) Provisional application No. 62/024,399, filed on Jul. 14, 2014.

(51) Int. Cl.
*C07K 16/40* (2006.01)
*A61K 39/395* (2006.01)

(52) U.S. Cl.
CPC ........ *C07K 16/40* (2013.01); *A61K 39/39591* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 6,020,004 A | 3/2000 | Gombotz et al. | |
| 6,036,978 A | 3/2000 | Gombotz et al. | |
| 6,083,534 A | 7/2000 | Wallach et al. | |
| 6,245,740 B1 | 6/2001 | Goldenberg et al. | |
| 6,432,449 B1 | 8/2002 | Goldenberg et al. | |
| 6,451,346 B1 | 9/2002 | Shah et al. | |
| 6,541,033 B1 | 4/2003 | Shah | |
| 6,541,606 B2 | 4/2003 | Margolin et al. | |
| 8,030,457 B2 | 10/2011 | Jackson et al. | |
| 2011/0027287 A1* | 2/2011 | Jackson .................. | A61K 31/22 424/139.1 |

FOREIGN PATENT DOCUMENTS

| | | |
|---|---|---|
| WO | 02/072636 A2 | 9/2002 |
| WO | 2009/026558 A1 | 2/2009 |
| WO | 2012/154999 A1 | 11/2012 |
| WO | 2013/166448 A1 | 11/2013 |
| WO | 2016/010927 A1 | 1/2016 |

OTHER PUBLICATIONS

Rudikoff et al. (Proc Natl Acad Sci USA 1982 vol. 79 p. 1979).*
MacCallunn et al. (J. Mol. Biol. 1996 262, 732-745).*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Lamminmaki et al. (JBC 2001, 276:36687-36694).*
Akers, Excipient-Drug Interactions in Parenteral Formulations, 2002, Journal of Pharmaceutical Sciences, vol. 91, No. 11: 2283-2300.
Arnon et al., Complexes and Conjugates of CIS-Pt for Immunotargeted Chemotherapy, Adv. Exp. Med. Biol. 303, 79-90 (1991).
Basu, S. K., Govardhan, C. P., Jung, C. W., Margolin, A. L. (2004) Protein crystals for the delivery of biopharmaceuticals, Expert Opin. Biol. Ther. 4(3), 301-317.
Costet et al., Hepatic PCSK9 Expression is Regulated by Nutritional Status via Insulin and Sterol Regulatory Element-binding Protein 1C, The Journal of Biological Chemistry, vol. 281, No. 10, pp. 6211-6218, 2006.
Dreuth, J., Haas C. (1992) Protein crystals and their stability, J. Crystal Growth 122, pp. 107-109.
Egor Trilisky et al.: Crystallization and liquid-liquid separation of monoclonal antibodies and fc-fusion proteins: Screening results, Biotechnology Progress, vol. 27, No. 4, Jul. 8, 2011, pp. 1054-1067.
Fundamental Immunology, Ch. 7 (Paul, W., ed, 2nd ed. Raven Press, N.Y. (1989).
Gilliland, A Biological Macromolecule Crystallization Database: A Basis for a Crystallization Strategy, Journal of Crystal Growth, 90: 51-59, (1988).
Greenfield et al., Evaluation in Vitro of Adriamycin Immunoconjugates Synthesized Using an Acid-sensitive Hydrazone Linker, Cancer Research 50, 6600-6607, (1990).
Hagedorn H. C.; Jensen, B. N.; Krarup, N. B.; Woodstrup, I., Protamine insulinate, (1936) J. Am. Med. Assn. 106, 177-180.
Jen, A., Merkle, H.P. (2001) Diamonds in the rough: Protein crystals from a formulation perspective, Pharm. Res. 18, 1483-1488.
Jenkins, T. W. (1998) Three solutions of the protein solubility problem, Protein Science 7: 376-382.
Johnson, I. S. (2003) The trials and tribulations of producing the first genetically engineered drug. Nat. Rev. Drug. Discovery 2, 747-751.
Kabat et al., Sequences of Proteins of Immunological Interest, 5th Ed. Public Health Service, National Institutes of Health, Bethesda, Md. (1991).
Kiseleva et al., Anti DNA-transDDP (II) Antibodies for Detecting Specific DNA Sequences, Mol. Biol. (USSR) 25, 508-514 (1991).
Liang et al., "Proprotein convertase substilisin/kexin type 9 antagonism reduces low-density lipoprotein cholesterol in statin-treated hypercholesterolemic nonhuman primates, Journal of Pharmacology and Experimental Therapeutics", American Society for Pharmacology and Experimental Therapeutics, US, vol. 340, No. 2, Feb. 1, 2012, pp. 228-236.

(Continued)

*Primary Examiner* — Sharon X Wen
(74) *Attorney, Agent, or Firm* — Connie Wong

(57) ABSTRACT

Described herein are anti-PCSK9 antibody crystals, methods of making such antibody crystals and formulations comprising the antibody crystals.

33 Claims, 10 Drawing Sheets

Specification includes a Sequence Listing.

(56) References Cited

OTHER PUBLICATIONS

McPherson, Crystallization of Macromolecules: General Principles, Methods Enzymol 114: 112-120 (1985).

PCT International Search Report and PCT Written Opinion of the International Searching Authority for International Application No. PCT/US2015/040211.

Pechenov, S., Shenoy, B., Yang, M. X., Basu, S., Margolin, A. L. (2004) Injectable controlled release formulations incorporating protein crystals, Journal of Controlled Releases 96, 149-158.

Shields et al., High Resolution Mapping of the Binding Site on Human IgG1 for FcγRI, FcγRII, FcγRIII, and FcRn and Design of IgG1 Variants with Improved Binding to the FcγR, The Journal of Biological Chemistry, 276(9):6591-6604 (2001).

Shire, S.J., Zahra, S., Liu, J. (2004) Challenges in the development of high concentration formulations, Journal of Pharmaceutical Sciences, vol. 93, No. 6, pp. 1390-1402.

The Protein Data Bank: A Computer-based Archival File for Macromolecular Structure at the Brookhaven National Laboratory (www.rcsb.org/pdb/; Bernstein et al., 1977, J Mol Biol 112: 535-542.

Van G Ni et al., A PCSK9-binding antibody that structurally mimics the EPG(A) domain of LDL-receptor reduces LDL cholesterol in vivo, Journal of Lipid Research, American Society for Biochemistry and Molecular Biology, Inc. US, vol. 52, No. 1, Jan. 2011, pp. 78-86.

Yang, M.X., Shenoy, B., Disttler, M., Patel, R., McGrath, M., Pechenov, S., Margolin, A.L. (2003) Crystalline monoclonal antibodies for subcutaneous delivery, PNAS, vol. 100, pp. 6934-6939.

PCT International Search Report and PCT Written Opinion of the International Search Authority for International Application No. PCT/US2015/040217.

* cited by examiner

FIG. 1A
SEQ ID NO:1

QEDEDGDYEELVLALRSEEDGLAEAPEHGTTATFHRCAKDPWRLPGTYVVVLKEE
THLSQSERTARRLQAQAARRGYLTKILHVFHGLLPGFLVKMSGDLLELALKLPHV
DYIEEDSSVFAQSIPWNLERITPPRYRADEYQPPDGGSLVEVYLLDTSIQSDHRE
IEGRVMVTDFENVPEEDGTRFHRQASKCDSHGTHLAGVVSGRDAGVAKGASMRSL
RVLNCQGKGTVSGTLIGLEFIRKSQLVQPVGPLVVLLPLAGGYSRVLNAACQRLA
RAGVVLVTAAGNFRDDACLYSPASAPEVITVGATNAQDQPVTLGTLGTNFGRCVD
LFAPGEDIIGASSDCSTCFVSQSGTSQAAAHVAGIAAMMLSAEPELTLAELRQRL
IHFSAKDVINEAWFPEDQRVLTPNLVAALPPSTHGAGWQLFCRTVWSAHSGPTRM
ATAIARCAPDEELLSCSSFSRSGKRRGERMEAQGGKLVCRAHNAFGGEGVYAIAR
CCLLPQANCSVHTAPPAEASMGTRVHCHQQGHVLTGCSSHWEVEDLGTHKPPVLR
PRGQPNQCVGHREASIHASCCHAPGLECKVKEHGIPAPQGQVTVACEEGWTLTGC
SALPGTSHVLGAYAVDNTCVVRSRDVSTTGSTSEEAVTAVAICCRSRHLAQASQE
LQ

FIG. 1B-1

```
                10        20        30        40        50
            ----------|---------|---------|---------|---------|
Query    :  atgggcaccgtcagctccaggcggtcctggtggccgctgccactgctgct    SEQ ID NO:2
Frame1   :   M  G  T  V  S  S  R  R  S  W  W  P  L  P  L  L      SEQ ID NO:3

60        70        80        90       100
            ----------|---------|---------|---------|---------|
Query    :  gctgctgctgctgctcctgggtcccgcgggcgcccgtgcgcaggaggacg
Frame1   :   L  L  L  L  L  G  P  A  G  A  R  A  Q  E  D  E 110       120       130       140       150
            ----------|---------|---------|---------|---------|
Query    :  aggacggcgactacgaggagctggtgctagccttgcgctccgaggaggac
Frame1   :   D  G  D  Y  E  E  L  V  L  A  L  R  S  E  E  D 50          160       170       180       190       200
            ----------|---------|---------|---------|---------|
Query    :  ggcctggccgaagcacccgagcacggaaccacagccaccttccaccgctg
Frame1   :   G  L  A  E  A  P  E  H  G  T  T  A  T  F  H  R  C 210       220       230       240       250
            ----------|---------|---------|---------|---------|
Query    :  cgccaaggatccgtggaggttgcctggcacctacgtggtggtgctgaagg
Frame1   :   A  K  D  P  W  R  L  P  G  T  Y  V  V  V  L  K  E 50          260       270       280       290       300
            ----------|---------|---------|---------|---------|
Query    :  aggagacccacctctcgcagtcagagcgcactgcccgccgcctgcaggcc
Frame1   :   E  T  H  L  S  Q  S  E  R  T  A  R  R  L  Q  A 310       320       330       340       350
            ----------|---------|---------|---------|---------|
Query    :  caggctgcccgccggggatacctcaccaagatcctgcatgtcttccatgg
Frame1   :   Q  A  A  R  R  G  Y  L  T  K  I  L  H  V  F  H  G 50          360       370       380       390       400
            ----------|---------|---------|---------|---------|
Query    :  ccttcttcctggcttcctggtgaagatgagtggcgacctgctggagctgg
Frame1   :   L  L  P  G  F  L  V  K  M  S  G  D  L  L  E  L  A 410       420       430       440       450
            ----------|---------|---------|---------|---------|
Query    :  ccttgaagttgccccatgtcgactacatcgaggaggactcctctgtcttt
Frame1   :   L  K  L  P  H  V  D  Y  I  E  E  D  S  S  V  F 50          460       470       480       490       500
            ----------|---------|---------|---------|---------|
Query    :  gcccagagcatcccgtggaacctggagcggattacccctccgcggtaccg
Frame1   :   A  Q  S  I  P  W  N  L  E  R  I  T  P  P  R  Y  R 510       520       530       540       550
            ----------|---------|---------|---------|---------|
Query    :  ggcggatgaataccagcccccccgacggaggcagcctggtggaggtgtatc
Frame1   :   A  D  E  Y  Q  P  P  D  G  G  S  L  V  E  V  Y  L
```

FIG. 1B-2

```
            50        560        570        580        590        600
           ----------|----------|----------|----------|----------|
Query   : tcctagacaccagcatacagagtgaccaccgggaaatcgagggcagggtc
Frame1  :   L  D  T  S  I  Q  S  D  H  R  E  I  E  G  R  V 610        620        630        640        650
           ----------|----------|----------|----------|----------|
Query   : atggtcaccgacttcgagaatgtgcccgaggaggacgggacccgcttcca
Frame1  :   M  V  T  D  F  E  N  V  P  E  E  D  G  T  R  F  H 50        660        670        680        690        700
           ----------|----------|----------|----------|----------|
Query   : cagacaggccagcaagtgtgacagtcatggcacccacctggcaggggtgg
Frame1  :   R  Q  A  S  K  C  D  S  H  G  T  H  L  A  G  V  V 710        720        730        740        750
           ----------|----------|----------|----------|----------|
Query   : tcagcggccgggatgccggcgtggccaagggtgccagcatgcgcagcctg
Frame1  :   S  G  R  D  A  G  V  A  K  G  A  S  M  R  S  L 50        760        770        780        790        800
           ----------|----------|----------|----------|----------|
Query   : cgcgtgctcaactgccaagggaagggcacggttagcggcaccctcatagg
Frame1  :   R  V  L  N  C  Q  G  K  G  T  V  S  G  T  L  I  G 810        820        830        840        850
           ----------|----------|----------|----------|----------|
Query   : cctggagtttattcggaaaagccagctggtccagcctgtggggccactgg
Frame1  :   L  E  F  I  R  K  S  Q  L  V  Q  P  V  G  P  L  V 50        860        870        880        890        900
           ----------|----------|----------|----------|----------|
Query   : tggtgctgctgcccctggcgggtgggtacagccgcgtcctcaacgccgcc
Frame1  :   V  L  L  P  L  A  G  G  Y  S  R  V  L  N  A  A 910        920        930        940        950
           ----------|----------|----------|----------|----------|
Query   : tgccagcgcctggcgagggctggggtcgtgctggtcaccgctgccggcaa
Frame1  :   C  Q  R  L  A  R  A  G  V  V  L  V  T  A  A  G  N 50        960        970        980        990       1000
           ----------|----------|----------|----------|----------|
Query   : cttccgggacgatgcctgcctctactccccagcctcagctcccgaggtca
Frame1  :   F  R  D  D  A  C  L  Y  S  P  A  S  A  P  E  V  I 1010       1020       1030       1040       1050
           ----------|----------|----------|----------|----------|
Query   : tcacagttggggccaccaatgcccaggaccagccggtgaccctggggact
Frame1  :   T  V  G  A  T  N  A  Q  D  Q  P  V  T  L  G  T 50       1060       1070       1080       1090       1100
           ----------|----------|----------|----------|----------|
Query   : ttggggaccaactttggccgctgtgtggacctctttgccccaggggagga
Frame1  :   L  G  T  N  F  G  R  C  V  D  L  F  A  P  G  E  D
```

FIG. 1B-3

```
          100        1110       1120       1130       1140       1150
          ----------|----------|----------|----------|----------|
Query   : catcattggtgcctccagcgactgcagcacctgctttgtgtcacagagtg
Frame1  :  I  I  G  A  S  S  D  C  S  T  C  F  V  S  Q  S  G 150        1160       1170       1180       1190       1200
          ----------|----------|----------|----------|----------|
Query   : ggacatcacaggctgctgcccacgtggctggcattgcagccatgatgctg
Frame1  :  T  S  Q  A  A  A  H  V  A  G  I  A  A  M  M  L 200        1210       1220       1230       1240       1250
          ----------|----------|----------|----------|----------|
Query   : tctgccgagccggagctcaccctggccgagttgaggcagagactgatcca
Frame1  :  S  A  E  P  E  L  T  L  A  E  L  R  Q  R  L  I  H 250        1260       1270       1280       1290       1300
          ----------|----------|----------|----------|----------|
Query   : cttctctgccaaagatgtcatcaatgaggcctggttccctgaggaccagc
Frame1  :  F  S  A  K  D  V  I  N  E  A  W  F  P  E  D  Q  R 300        1310       1320       1330       1340       1350
          ----------|----------|----------|----------|----------|
Query   : gggtactgaccccaacctggtggccgccctgccccccagcacccatggg
Frame1  :  V  L  T  P  N  L  V  A  A  L  P  P  S  T  H  G 350        1360       1370       1380       1390       1400
          ----------|----------|----------|----------|----------|
Query   : gcaggttggcagctgttttgcaggactgtgtggtcagcacactcggggcc
Frame1  :  A  G  W  Q  L  F  C  R  T  V  W  S  A  H  S  G  P 400        1410       1420       1430       1440       1450
          ----------|----------|----------|----------|----------|
Query   : tacacggatggccacagccatcgcccgctgcgccccagatgaggagctgc
Frame1  :  T  R  M  A  T  A  I  A  R  C  A  P  D  E  E  L 450        1460       1470       1480       1490       1500
          ----------|----------|----------|----------|----------|
Query   : tgagctgctccagtttctccaggagtgggaagcggcggggcgagcgcatg
Frame1  :  S  C  S  S  F  S  R  S  G  K  R  R  G  E  R  M 500        1510       1520       1530       1540       1550
          ----------|----------|----------|----------|----------|
Query   : gaggcccaaggggcaagctggtctgccgggccacaacgcttttggggg
Frame1  :  E  A  Q  G  G  K  L  V  C  R  A  H  N  A  F  G  G 550        1560       1570       1580       1590       1600
          ----------|----------|----------|----------|----------|
Query   : tgagggtgtctacgccattgccaggtgctgcctgctaccccaggccaact
Frame1  :  E  G  V  Y  A  I  A  R  C  C  L  L  P  Q  A  N  C 600        1610       1620       1630       1640       1650
          ----------|----------|----------|----------|----------|
Query   : gcagcgtccacacagctccaccagctgaggccagcatggggacccgtgtc
Frame1  :  S  V  H  T  A  P  P  A  E  A  S  M  G  T  R  V
```

FIG. 1B-4

```
              650       1660      1670      1680      1690      1700
         ----------|---------|---------|---------|---------|
Query  : cactgccaccaacagggccacgtcctcacaggctgcagctcccactggga
Frame1 :  H  C  H  Q  Q  G  H  V  L  T  G  C  S  S  H  W  E 700       1710      1720      1730      1740      1750
         ----------|---------|---------|---------|---------|
Query  : ggtggaggaccttggcacccacaagccgcctgtgctgaggccacgaggtc
Frame1 :  V  E  D  L  G  T  H  K  P  P  V  L  R  P  R  G  Q 750       1760      1770      1780      1790      1800
         ----------|---------|---------|---------|---------|
Query  : agcccaaccagtgcgtgggccacagggaggccagcatccacgcttcctgc
Frame1 :   P  N  Q  C  V  G  H  R  E  A  S  I  H  A  S  C 800       1810      1820      1830      1840      1850
         ----------|---------|---------|---------|---------|
Query  : tgccatgccccaggtctggaatgcaaagtcaaggagcatggaatcccggc
Frame1 :  C  H  A  P  G  L  E  C  K  V  K  E  H  G  I  P  A 850       1860      1870      1880      1890      1900
         ----------|---------|---------|---------|---------|
Query  : ccctcaggggcaggtgaccgtggcctgcgaggagggctggaccctgactg
Frame1 :   P  Q  G  Q  V  T  V  A  C  E  E  G  W  T  L  T  G 900       1910      1920      1930      1940      1950
         ----------|---------|---------|---------|---------|
Query  : gctgcagcgccctccctgggacctcccacgtcctgggggcctacgccgta
Frame1 :   C  S  A  L  P  G  T  S  H  V  L  G  A  Y  A  V 950       1960      1970      1980      1990      2000
         ----------|---------|---------|---------|---------|
Query  : gacaacacgtgtgtagtcaggagccgggacgtcagcactacaggcagcac
Frame1 :  D  N  T  C  V  V  R  S  R  D  V  S  T  T  G  S  T 2010      2020      2030      2040      2050
         ----------|---------|---------|---------|---------|
Query  : cagcgaagaggccgtgacagccgttgccatctgctgccggagccggcacc
Frame1 :   S  E  E  A  V  T  A  V  A  I  C  C  R  S  R  H  L 50       2060      2070      2080      2090      2100
         ----------|---------|---------|---------|---------|
Query  : tggcgcaggcctcccaggagctccag
Frame1 :  A  Q  A  S  Q  E  L  Q
```

FIG. 2A

21B12 Heavy chain variable regions:

Nucleotide sequence of heavy chain variable region:

5'CAGGTTCAGCTGGTGCAGTCTGGAGCTGAGGTGAAGAAGCCTGGG
GCCTCAGTGAAGGTCTCCTGCAAGGCTTCTGGTTACACCTTAACCAG
CTATGGTATCAGCTGGGTGCGACAGGCCCCTGGACAAGGGCTTGAGT
GGATGGGATGGGTCAGTTTTATAATGGTAACACAAACTATGCACAG
AAGCTCCAGGGCAGAGGCACCATGACCACAGACCCATCCACGAGCA
CAGCCTACATGGAGCTGAGGAGCCTGAGATCTGACGACACGGCCGT
GTATTACTGTGCGAGAGGCTACGGTATGGACGTCTGGGGCCAAGGG
ACCACGGTCACCGTCTCCTCT3' (SEQ ID NO:4)

Amino acid sequence of heavy chain variable region:

QVQLVQSGAEVKKPGASVKVSCKASGYTLTSYGISWVRQAPGQGLEW
MGWVSFYNGNTNYAQKLQGRGTMTTDPSTSTAYMELRSLRSDDTAVY
YCARGYGMDVWGQGTTVTVSS (SEQ ID NO:5)

Alternative Nucleotide sequence of heavy chain variable region:

5'GAGGTTCAGCTGGTGCAGTCTGGAGCTGAGGTGAAGAAGCCTGGG
GCCTCAGTGAAGGTCTCCTGCAAGGCTTCTGGTTACACCTTAACCAG
CTATGGTATCAGCTGGGTGCGACAGGCCCCTGGACAAGGGCTTGAGT
GGATGGGATGGGTCAGTTTTATAATGGTAACACAAACTATGCACAG
AAGCTCCAGGGCAGAGGCACCATGACCACAGACCCATCCACGAGCA
CAGCCTACATGGAGCTGAGGAGCCTGAGATCTGACGACACGGCCGT
GTATTACTGTGCGAGAGGCTACGGTATGGACGTCTGGGGCCAAGGG
ACCACGGTCACCGTCTCCTCT3' (SEQ ID NO:6)

Alternative Amino acid sequence of heavy chain variable region:

EVQLVQSGAEVKKPGASVKVSCKASGYTLTSYGISWVRQAPGQGLEW
MGWVSFYNGNTNYAQKLQGRGTMTTDPSTSTAYMELRSLRSDDTAVY
YCARGYGMDVWGQGTTVTVSS (SEQ ID NO:7)

FIG. 2B

21B12 Light chain variable regions:

Nucleotide sequence of light chain variable region:

5'CAGTCTGCCCTGACTCAGCCTGCCTCCGTGTCTGGGTCTCCTGGAC
AGTCGATCACCATCTCCTGCACTGGAACCAGCAGTGACGTTGGTGGT
TATAACTCTGTCTCCTGGTACCAACAGCACCCAGGCAAAGCCCCCAA
ACTCATGATTTATGAGGTCAGTAATCGGCCCTCAGGGGTTTCTAATC
GCTTCTCTGGCTCCAAGTCTGGCAACACGGCCTCCCTGACCATCTCT
GGGCTCCAGGCTGAGGACGAGGCTGATTATTACTGCAATTCATATAC
AAGCACCAGCATGGTATTCGGCGGAGGGACCAAGCTGACCGTCCTA
3' (SEQ ID NO:8)

Amino acid sequence of light chain variable region:

QSALTQPASVSGSPGQSITISCTGTSSDVGGYNSVSWYQQHPGKAPKLM
IYEVSNRPSGVSNRFSGSKSGNTASLTISGLQAEDEADYYCNSYTSTSMV
FGGGTKLTVL (SEQ ID NO:9)

Alternative Nucleotide sequence of light chain variable region:

5'GAGTCTGCCCTGACTCAGCCTGCCTCCGTGTCTGGGTCTCCTGGAC
AGTCGATCACCATCTCCTGCACTGGAACCAGCAGTGACGTTGGTGGT
TATAACTCTGTCTCCTGGTACCAACAGCACCCAGGCAAAGCCCCCAA
ACTCATGATTTATGAGGTCAGTAATCGGCCCTCAGGGGTTTCTAATC
GCTTCTCTGGCTCCAAGTCTGGCAACACGGCCTCCCTGACCATCTCT
GGGCTCCAGGCTGAGGACGAGGCTGATTATTACTGCAATTCATATAC
AAGCACCAGCATGGTATTCGGCGGAGGGACCAAGCTGACCGTCCTA
3' (SEQ ID NO:10)

Alternative Amino acid sequence of light chain variable region:

ESALTQPASVSGSPGQSITISCTGTSSDVGGYNSVSWYQQHPGKAPKLM
IYEVSNRPSGVSNRFSGSKSGNTASLTISGLQAEDEADYYCNSYTSTSMV
FGGGTKLTVL (SEQ ID NO:11)

FIG. 3

Constant Domains

Human IgG2:

ASTKGPSVFPLAPCSRSTSESTAALGCLVKDYFPEPVTVSWNSGALTSG
VHTFPAVLQSSGLYSLSSVVTVPSSNFGTQTYTCNVDHKPSNTKVDKTV
ERKCCVECPPCPAPPVAGPSVFLFPPKPKDTLMISRTPEVTCVVVDVSHE
DPEVQFNWYVDGVEVHNAKTKPREEQFNSTFRVVSVLTVVHQDWLNG
KEYKCKVSNKGLPAPIEKTISKTKGQPREPQVYTLPPSREEMTKNQVSLT
CLVKGFYPSDIAVEWESNGQPENNYKTTPPMLDSDGSFFLYSKLTVDKS
RWQQGNVFSCSVMHEALHNHYTQKSLSLSPGK (SEQ ID NO: 12)

Human IgG4:

ASTKGPSVFPLAPCSRSTSESTAALGCLVKDYFPEPVTVSWNSGALTSG
VHTFPAVLQSSGLYSLSSVVTVPSSSLGTKTYTCNVDHKPSNTKVDKRV
ESKYGPPCPSCPAPEFLGGPSVFLFPPKPKDTLMISRTPEVTCVVVDVSQ
EDPEVQFNWYVDGVEVHNAKTKPREEQFNSTYRVVSVLTVLHQDWLN
GKEYKCKVSNKGLPSSIEKTISKAKGQPREPQVYTLPPSQEEMTKNQVS
LTCLVKGFYPSDIAVEWESNGQPENNYKTTPPVLDSDGSFFLYSRLTVD
KSRWQEGNVFSCSVMHEALHNHYTQKSLSLSLGK (SEQ ID NO: 13)

Human lambda:

QPKAAPSVTLFPPSSEELQANKATLVCLISDFYPGAVTVAWKADSSPVK
AGVETTTPSKQSNNKYAASSYLSLTPEQWKSHRSYSCQVTHEGSTVEKT
VAPTECS (SEQ ID NO: 14)

Human kappa:

TVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVT
KSFNRGEC (SEQ ID NO: 15)

FIG. 4A

21B12 Light chains:

21B12 mature light chain:

QSALTQPASVSGSPGQSITISCTGTSSDVGGYNSVSWYQQHPGKAPKLMIY
EVSNRPSGVSNRFSGSKSGNTASLTISGLQAEDEADYYCNSYTSTSMVFGG
GTKLTVLGQPKAAPSVTLFPPSSEELQANKATLVCLISDFYPGAVTVAWKA
DSSPVKAGVETTTPSKQSNNKYAASSYLSLTPEQWKSHRSYSCQVTHEGST
VEKTVAPTECS (SEQ ID NO:16)

Alternative 21B12 mature light chain:

ESALTQPASVSGSPGQSITISCTGTSSDVGGYNSVSWYQQHPGKAPKLMIY
EVSNRPSGVSNRFSGSKSGNTASLTISGLQAEDEADYYCNSYTSTSMVFGG
GTKLTVLGQPKAAPSVTLFPPSSEELQANKATLVCLISDFYPGAVTVAWKA
DSSPVKAGVETTTPSKQSNNKYAASSYLSLTPEQWKSHRSYSCQVTHEGST
VEKTVAPTECS (SEQ ID NO:17)

FIG. 4B

21B12 Heavy chains:

21B12 mature heavy chain:

QVQLVQSGAEVKKPGASVKVSCKASGYTLTSYGISWVRQAPGQGLEWMG
WVSFYNGNTNYAQKLQGRGTMTTDPSTSTAYMELRSLRSDDTAVYYCAR
GYGMDVWGQGTTVTVSSASTKGPSVFPLAPCSRSTSESTAALGCLVKDYF
PEPVTVSWNSGALTSGVHTFPAVLQSSGLYSLSSVVTVPSSNFGTQTYTCN
VDHKPSNTKVDKTVERKCCVECPPCPAPPVAGPSVFLFPPKPKDTLMISRT
PEVTCVVVDVSHEDPEVQFNWYVDGVEVHNAKTKPREEQFNSTFRVVSV
LTVVHQDWLNGKEYKCKVSNKGLPAPIEKTISKTKGQPREPQVYTLPPSRE
EMTKNQVSLTCLVKGFYPSDIAVEWESNGQPENNYKTTPPMLDSDGSFFL
YSKLTVDKSRWQQGNVFSCSVMHEALHNHYTQKSLSLSPGK (SEQ ID NO:18)

Alternative 21B12 mature heavy chain:

EVQLVQSGAEVKKPGASVKVSCKASGYTLTSYGISWVRQAPGQGLEWMG
WVSFYNGNTNYAQKLQGRGTMTTDPSTSTAYMELRSLRSDDTAVYYCAR
GYGMDVWGQGTTVTVSSASTKGPSVFPLAPCSRSTSESTAALGCLVKDYF
PEPVTVSWNSGALTSGVHTFPAVLQSSGLYSLSSVVTVPSSNFGTQTYTCN
VDHKPSNTKVDKTVERKCCVECPPCPAPPVAGPSVFLFPPKPKDTLMISRT
PEVTCVVVDVSHEDPEVQFNWYVDGVEVHNAKTKPREEQFNSTFRVVSV
LTVVHQDWLNGKEYKCKVSNKGLPAPIEKTISKTKGQPREPQVYTLPPSRE
EMTKNQVSLTCLVKGFYPSDIAVEWESNGQPENNYKTTPPMLDSDGSFFL
YSKLTVDKSRWQQGNVFSCSVMHEALHNHYTQKSLSLSPGK (SEQ ID NO:19)

CRYSTALLINE ANTIBODY FORMULATIONS

CROSS REFERENCE TO RELATED APPLICATIONS

This application is a national stage application under 35 U.S.C. § 371 of International Application No. PCT/US2015/040211, having an international filing date of Jul. 13, 2015, which claims the benefit of, and priority to U.S. Provisional Application No. 62/024,399 filed Jul. 14, 2014, which is incorporated in its entirety by reference herein.

INCORPORATION BY REFERENCE OF MATERIAL SUBMITTED ELECTRONICALLY

This application contains, as a separate part of disclosure, a Sequence Listing in computer-readable form (filename: Seq List10-07-13_ST25.txt, created Jun. 26, 2014 which is 42 KB in size), which is incorporated by reference in its entirety.

BACKGROUND

Monoclonal antibodies are extensively used as biotherapeutics with an increasing demand to meet high concentrations of over a 100 mg/ml for delivery. This presents a challenge for solubility limited proteins via a subcutaneous route, since the preferred subcutaneous administration limit is 1.2 ml (Yang, M. X., Shenoy, B., Disttler, M., Patel, R., McGrath, M., Pechenov, S., Margolin, A. L. (2003) Crystalline monoclonal antibodies for subcutaneous delivery, PNAS 100, 6934-6939). Development of high concentration formulation poses a lot of challenges from a formulation, analytical, stability, manufacturing and drug delivery point of view (Shire, S. J., Zahra, S., Liu, J. (2004) Challenges in the development of high concentration formulations, *J. Pharm. Sci.* 93, 1390-1402). So far, high concentration formulation demands have been met by addition of excipients like amino acids, sugars and salts that increase stability, reduce aggregation and viscosity (Shire, supra and Jenkins, T. W. (1998) Three solutions of the protein solubility problem, *Protein Science* 7: 376-382).

Protein crystals are often viewed as only the intermediates to a protein structure but they also have an important role from a formulation perspective. Protein molecules in the crystalline form have the lowest entropy thus making them 3-6 kcal/ml more stable than in the liquid state (Dreuth, J., Haas, C. (1992) Protein crystals and their stability, *J. Crystal Growth* 122, 107-109). The main advantages of crystalline formulation include high protein concentration, lower viscosity, stability, elimination of frequent dosage due to high concentration and controlled release properties (Yang, supra, and Basu, S. K., Govardhan, C. P., Jung, C. W., Margolin, A. L. (2004) Protein crystals for the delivery of biopharmaceuticals, *Expert Opin. Biol. Thera.* 4, 301-317).

Crystallization conditions can be manipulated to achieve different morphologies for desired controlled release properties (Pechenov, S., Shenoy, B., Yang, M. X., Basu, S., Margolin, A. L. (2004) Injectable controlled release formulations incorporating protein crystals, *Journal of Controlled Release* 96, 149-158). Insulin crystalline formulations were first reported in 1920's and today, it is not only the first recombinant protein therapeutic approved by the FDA, it is also the first approved crystalline protein therapeutic (Hagedorn H. C.; Jensen, B. N.; Krarup, N. B.; Wodstrup, I. Protamine insulinate, (1936) J. Am. Med. Assn. 106, 177-180; Johnson, I. S. (2003) The trials and tribulations of producing the first genetically engineered drug. Nat. Rev. Drug. Discovery 2, 747-751; and Basu, S. K., Govardhan, C. P., Jung, C. W., Margolin, A. L. (2004) Protein crystals for the delivery of biopharmaceuticals, Expert Opin. Biol. Thera. 4, 301-317). Macromolecules are challenging to crystallize due to their inherent flexibility, but, once crystallized, often pose challenges from a formulation and regulatory perspective (Basu, supra, and Jen, A., Merkle, H. P. (2001) Diamonds in the rough: Protein crystals from a formulation perspective, Pharm. Res. 18, 1483-1488.).

SUMMARY OF THE INVENTION

The invention relates to crystals of anti-PCSK9 immunoglobulin type G (IgG) antibodies (more specifically, antibody 21B12) that are suitable for use in crystalline formulations for parenteral administration; solutions, salts and methods for producing such crystals; methods of using such crystals to prepare crystalline formulations for use as medicaments, and methods of using such crystalline formulations for treating mammals, specifically humans.

In the crystals or formulations described herein, the anti-PCSK9 IgG can comprise the heavy and light chain complementary determining regions (CDRs) of antibody, 21B12. Thus, in some embodiments, the antibody is an IgG comprising a light chain complementarity region (CDR) of the CDRL1 sequence in SEQ ID NO:9, a CDRL2 of the CDRL2 sequence in SEQ ID NO:9, and a CDRL3 of the CDRL3 sequence in SEQ ID NO:9, and a heavy chain complementarity determining region (CDR) of the CDRH1 sequence in SEQ ID NO:5, a CDRH2 of the CDRH2 sequence in SEQ ID NO:5, and a CDRH3 of the CDRH3 sequence in SEQ ID NO:5. In some other embodiments, the antibody is an IgG comprising a light chain complementarity region (CDR) of the CDRL1 sequence in SEQ ID NO:11, a CDRL2 of the CDRL2 sequence in SEQ ID NO:11, and a CDRL3 of the CDRL3 sequence in SEQ ID NO:11, and a heavy chain complementarity determining region (CDR) of the CDRH1 sequence in SEQ ID NO:7, a CDRH2 of the CDRH2 sequence in SEQ ID NO:7, and a CDRH3 of the CDRH3 sequence in SEQ ID NO:7. In some embodiments, the antibody is an IgG comprising the amino acid sequences of: SEQ ID NO:20 or SEQ ID NO:21 (21B12 CDRH1), and SEQ ID NO:22 (21B12 CDRH2), and SEQ ID NO:23 (21B12 CDRH3), and SEQ ID NO:24 (21B12 CDRL1), and SEQ ID NO:25 (21B12 CDRL2), and SEQ ID NO:26 (21B12 CDRL3).

In the crystals or formulations described herein, the anti-PCSK9 IgG antibody can comprise the heavy and light chain variable regions of an antibody having at least 70%, at least 80%, at least 90%, at least 95%, at least 98%, at least 99% sequence identity to antibody, 21B12. Thus, in some embodiments, the antibody is an IgG comprising a light chain variable region comprising an amino acid sequence that is at least 70% identical to that of SEQ ID NO:9 or SEQ ID NO:11 and a heavy chain variable region that comprises an amino acid sequence that is at least 70% identical to that of SEQ ID NO:5 or SEQ ID NO:7. In some embodiments, the antibody is an IgG comprising a light chain variable region comprising an amino acid sequence that is at least 80% identical to that of SEQ ID NO:9 or SEQ ID NO:11 and a heavy chain variable region that comprises an amino acid sequence that is at least 80% identical to that of SEQ ID NO:5 or SEQ ID NO:7. In some embodiments, the antibody is an IgG comprising a light chain variable region comprising an amino acid sequence that is at least 90% identical to that of SEQ ID NO:9 or SEQ ID NO:11 and a heavy chain variable region that comprises an amino acid sequence that is at least 90% identical to that of SEQ ID NO:5 or SEQ ID NO:7. In some embodiments, the antibody is an IgG comprising a light chain variable region comprising an amino acid sequence that is at least 95% identical to that of SEQ ID NO:9 or SEQ ID NO:11 and a heavy chain variable region that comprises an amino acid sequence that is at least 95% identical to that of SEQ ID NO:5 or SEQ ID NO:7. In some embodiments, the antibody is an IgG comprising a light chain variable region comprising an amino acid sequence that is at least 98% identical to that of SEQ ID NO:9 or SEQ ID NO:11 and a heavy chain variable region that comprises an amino acid sequence that is at least 98% identical to that of SEQ ID NO:5 or SEQ ID NO:7. In some embodiments, the antibody is an IgG comprising a light chain variable region comprising an amino acid sequence that is at least 99% identical to that of SEQ ID NO:9 or SEQ ID NO:11 and a heavy chain variable region that comprises an amino acid sequence that is at least 99% identical to that of SEQ ID NO:5 or SEQ ID NO:7. In some embodiments, the antibody is an IgG comprising a light chain variable region comprising the amino acid sequence of SEQ ID NO:9 or SEQ ID NO:11 and a heavy chain variable region that comprises an amino acid sequence of SEQ ID NO:5 or SEQ ID NO:7. In some embodiments, the antibody comprises a light chain variable region comprising the amino acid sequence of SEQ ID NO:9 and a heavy chain variable region that comprises an amino acid sequence of SEQ ID NO:5. In some embodiments, the antibody comprises a light chain variable region comprising the amino acid sequence of SEQ ID NO:11 and a heavy chain variable region that comprises an amino acid sequence of SEQ ID NO:7.

In the crystals or formulations described herein, the anti-PCSK9 IgG antibody can comprise the heavy and light chain variable regions described above that are each fused to a suitable constant region. In some embodiments, the antibody comprises the mature heavy and light chains of antibody 21B12, (SEQ ID NOS:16 or 17, 21B12 mature light chain and SEQ ID NOS:18 or 19, 21B12 mature heavy chain). In some embodiments, the antibody comprises SEQ ID NO:16 and SEQ ID NO:18. In some embodiments, the antibody comprises SEQ ID NO:17 and SEQ ID NO:19. In some embodiments, the antibody comprises amino acid sequences obtainable by expressing in mammalian host cells the cDNA encoding the heavy and/or light chain, or alternatively the heavy and/or light chain variable regions, each fused to a suitable constant region, of antibody, 21B12, as described herein. In some embodiments, the antibody binds to PCSK9 of SEQ ID NO: 1 with a KD binding affinity of $10^{-7}$ or less (lower numbers meaning higher binding affinity.

The antibody crystals described herein can be characterized, for example, by size, shape, morphology, salt content, crystal packing, and other properties. In some embodiments, the crystal length ranges from about 10 μM to about 1000 μM, optionally with a morphology that is rod shaped, plate-shaped, block-shaped, UFO shaped, football shaped, leaf shaped, wheat shaped, singlet shaped, feather-shaped, ellipsoidal, straw-shaped, chrysanthemum-shaped, or spherical or mixtures thereof. Optionally, the crystals are in clusters. The crystals are also characterized by x-ray diffraction. For example, antibody 21B12 crystals may exhibit a rod shape, block shape, hexagonal shape, leaf sharp, surfboard shape or plate shape, or a mixture thereof, or other shapes. In some embodiments, antibody 21B12 crystals exhibited rod or hexagonal shapes.

In some or any embodiments, the antibody crystals described herein are characterized by the type of salt. Suitable salts for the production of antibody 21B12 crystals include, but are not limited to, one or more of the following: sodium dihydrogen phosphate, di-potassium hydrogen phosphate, sodium chloride, ammonium sulfate, ammonium chloride, ammonium citrate dibasic, ammonium citrate tribasic, magnesium formate dehydrate, potassium sodium tartrate tetrahydrate, tacsimate, sodium citrate dihydrate, sodium acetate trihydrate, di-ammonium tartrate, potassium sodium tartrate, sodium malonate, acetate, calcium acetate, cacodylate, CHES, lithium sulfate, magnesium chloride, magnesium sulfate, zinc acetate, cesium chloride, ammonium phosphate, sodium phosphase, potassium phosphate, sodium fluoride, potassium iodide, sodium idodide, ammonium iodide, sodium thiocyanate, potassium thiocyanate, sodium formate, potassium formate, ammonium formate, malic acid, succinic acid, ammonium nitrate, sodium nitrate, potassium thiocyanate, ammonium acetate and tascsimate. For example, other salts (including hydrates) for the production of antibody 21B12 crystals can include other dihydrogen phosphate salts, hydrogen phosphate salts, phosphate salts, fluoride salts, chloride salts, sulfate salts, tartrate salts, tacsimate salts, citrate salts, acetate salts, malonate salts, cacodylate salts, and iodide salts, thiocyanate salts, formate salts; with, for example, monovalent (e.g. sodium, potassium, ammonium) or divalent cations (e.g. including but not limited to zinc, magnesium, calcium).

In some or any embodiments, the antibody crystals are characterized by crystallization additives, which can influence the crystal growth and/or shape. Suitable crystallization additives include, but are not limited to, one or more of the following: precipitants such as PEG having a molecular weight of about 400 kD to about 20,000 kD, or about 1000 kD to about 5000 kD (e.g., PEG3350) or 2-methyl-2,4-pentanediol (MPD), surfactants including but not limited to polysorbate 20, polysorbate 80, polysorbate 100, or Triton X100, amino acids including but not limited to arginine, cysteine, glycine, histidine, lysine, proline etc., alpha amino acids or n-acyl-alpha amino acids including but not limited to n-acetyl L-arginine (also known as N-alpha N-acetly L-arginine or N2-acetyl-L-arginine), short peptides, small organic molecules, organic salts, nucleotides and carbohydrates. In some or any embodiments, the crystals are also characterized by the process by which they are produced, including remaining impurities. In some embodiments, the additives (e.g., PEG, MPD, glycerol) are at about 0.1% to about 95% w/v or v/v, or about 0.1% to about 70%, or about 0.1% to about 50%, or about 0.1% to about 10%, or about 10% to about 50%, or about 20%-50%, or at least 10%, or at least 20%.

Another aspect of the invention provides methods of making the crystals described herein. In some embodiments, the method comprises combining a solution of antibody 21B12 with a crystallization reagent comprising an appropriate salt, including any of the previously described salts, and/or a crystallization additive, including any of the previously described additives. In any of the embodiments described herein, the salt in the crystallization reagent is present at a concentration of about 0.1M to about 30M, optionally 0.1M to about 10M, or about 1M to about 10M. In any of the embodiments described herein, the additives (e.g., PEG, MPD, glycerol) are present at a concentration of about 0.1% to about 95% w/v or v/v, or about 0.1% to about 70%, or about 0.1% to about 50%, or about 0.1% to about 10%, or about 10% to about 50%, or about 20%-50%, or at least 10%, or at least 20%.

Methods of making antibody crystals optionally further comprise removing at least a portion of the crystallization buffer (e.g., by centrifugation) after the crystals are formed. In some embodiments, the crystals are then placed into a solution comprising an organic additive (e.g., ethanol or isopropanol). In some embodiments, excipients (e.g., sucrose, trehalose, sorbitol or proline) are added to the solution.

The methods of making the antibody crystals optionally further comprise the step of drying the crystals that have formed (e.g., by air drying the crystals or exposing the crystals to a vacuum or nitrogen gas).

Exemplary methods for producing the antibody crystals described herein include vapor diffusion and batch crystallization, which are known in the art.

Another aspect described herein are crystalline formulations (e.g., powder crystalline and liquid crystalline formulations) and methods of using antibody crystals described herein to prepare medicaments, such as crystalline formulations, for therapy of mammals including humans. Therapy of any of the conditions described herein is contemplated, optionally using any of the dosing and timing regimens described herein. The crystalline formulations comprise antibody crystals, e.g. antibody, 21B12 having one or more of the properties described herein (e.g. size, length, shape, salt content, additive content, crystal packing or other properties).

The crystalline formulations are suitable for parenteral administration, e.g. are sterile, have endotoxin levels acceptable for parenteral administration, e.g. <0.25 EU/mL or 0.008 EU/mg, and comprise pharmaceutically acceptable excipients. The crystalline formulations are also preferably of high protein concentrations, e.g. at least 100 mg/ml, 120 mg/ml 140 mg/mL, 150 mg/mL, 160 mg/mL, 170 mg/mL, 180 mg/mL, 190 mg/mL, 200 mg/mL, 210 mg/mL, 220 mg/mL, 230 mg/mL, 240 mg/mL, 250 mg/mL, 260 mg/mL, 270 mg/mL, 280 mg/mL, 290 mg/mL, 300 mg/mL, 310 mg/mL, 320 mg/mL, 330 mg/mL, 340 mg/mL, 350 mg/mL, 360 mg/mL, 370 mg/mL, 380 mg/mL, 390 mg/mL, 400 mg/mL, 410 mg/mL, 420 mg/mL, 430 mg/mL, 440 mg/mL, 450 mg/mL, 460 mg/mL, 480 mg/mL, 500 mg/mL or higher.

In some or any embodiments, the crystal formulation comprises excipients including, but not limited to amino acids, sucrose, trehalose and sorbitol, or other sugars or polyols.

In some or any embodiments, the crystalline formulations have a pH ranging from about 2 to about 12, or about 6 to about 9, or about 6 to 8.5, or about 7 to about 7.5 and an osmolality ranging from about 180 to about 420 mOsm/kg, or about 200 to about 400 mOsm/kg, or about 250 to about 350 mOsm/kg. While isotonic (250-350 mOsm/kg) and physiologic pH (about 7-7.5) is preferred, formulations may be prepared outside of these ranges as long as the crystals are formulated in physiological relevant conditions.

Optionally, the crystalline formulation suitable for parenteral administration (e.g., subcutaneous or intramuscular) is presented in a container, such as a single dose vial, multi-dose vial, syringe, pre-filled syringe or injection device. In some or any embodiments, the container comprises a single dose of an anti-PCSK9 antibody (e.g., about 100 mg to about 500 mg of anti-PCSK9 antibody). In one exemplary embodiment, a container may contain about 100 mg or 110 mg or 120 mg 130 mg or 140 mg or 150 mg 160 mg or 170 mg or 180 mg or 190 mg or 200 mg or 210 mg or 220 mg 230 mg or 240 mg or 250 mg 260 mg or 270 mg or 280 mg or 290 mg or 300 mg of the crystalline formulation of anti-PCSK9 antibody and would be suitable for administering a single dose of about 2, 3, 4, 5 or 6 up to about 16 mg/kg body weight. In other embodiments, a container may contain about 150 mg, or about 160 mg, or about 170 mg, or about 180 mg, or about 190 mg, or about 200 mg, or about 210 mg or about 220 mg or about 230 mg; or about 240 mg, or at about 250 mg; or about 250-450 mg; or about 280 mg, or about 290 mg or about 300 mg, or about 350 mg or about 360 mg; or about 420 mg or about 430 mg or about 440 mg or about 450 mg; or about 500 mg to about 1200 mg; or about 550 mg, or about 600 mg, or about 700 mg, or about 800 mg, or about 900 mg, or about 1000 mg, or about 1100 mg, or about 1200 mg of the crystalline formulation of anti-PCSK9 antibody. In any of such embodiments, the container may be suitable for administering a single dose of about 2, 3, 4, 5 or 6 up to about 16 mg/kg body weight. In any of these embodiments, the container may comprise the antibody at a high protein concentration such as those described herein. In any of these embodiments, the container may comprise a powdered formulation and be for reconstitution in a volume of about 0.5-2 mL.

Also disclosed are methods of reconstituting any of the foregoing powdered formulations comprising adding a sterile diluent to achieve a high protein constitution such as those described herein.

Also disclosed herein is a kit comprising such a container and a label comprising instructions to use the appropriate volume or amount of the crystalline formulation necessary to achieve a dose of from about 100 mg to about 1200 mg of anti-PCSK9 antibody, or from about 2-16 mg/kg of patient body weight.

Also disclosed herein are crystalline formulations (e.g., powder crystalline and/or liquid crystalline formulations) that are stable at room temperature for at least 1 month, 3 months, 6 months, 7 months, 8 months, 9 months, 10 months, 11 months, 1 year, 18 months, 2 years, 3 years, 4 years, 5 years, 6 years, 7 years, 8 years, 9 years, 10 years or longer. In some embodiments, the crystalline formulation comprises antibody 21B12 crystals and the formulation is stable at room temperature for at least 1 month, 3 months, 6 months, 7 months, 8 months, 9 months, 10 months, 11 months, 1 year, 18 months, 2 years, 3 years, 4 years, 5 years, 6 years, 7 years, 8 years, 9 years, 10 years or more.

Also described herein are methods of using the formulations described herein to treat and/or prevent cholesterol related disorders. In some embodiments, a "cholesterol related disorder" (which includes "serum cholesterol related disorders") includes any one or more of the following: familial hypercholesterolemia, non-familial hypercholesterolemia, hyperlipidemia, heart disease, metabolic syndrome, diabetes, coronary heart disease, stroke, cardiovascular diseases, Alzheimer's disease and generally dyslipidemias, which can be manifested, for example, by an elevated total serum cholesterol, elevated LDL, elevated triglycerides, elevated VLDL, and/or low HDL. Some non-limiting examples of primary and secondary dyslipidemias that can be treated using the formulations describe herein, either alone, or in combination with one or more other agents include the metabolic syndrome, diabetes mellitus, familial combined hyperlipidemia, familial hypertriglyceridemia, familial hypercholesterolemias, including heterozygous hypercholesterolemia, homozygous hypercholesterolemia, familial defective apolipoprotein B-100; polygenic hypercholesterolemia; remnant removal disease, hepatic lipase deficiency; dyslipidemia secondary to any of the following: dietary indiscretion, hypothyroidism, drugs including estrogen and progestin therapy, beta-blockers, and thiazide diuretics; nephrotic syndrome, chronic renal failure, Cushing's syndrome, primary biliary cirrhosis, glycogen storage diseases, hepatoma, cholestasis, acromegaly, insulinoma, isolated growth hormone deficiency, and alcohol-induced hypertriglyceridemia. The formulations described herein can also be useful in preventing or treating atherosclerotic diseases, such as, for example, cardiovascular death, non-cardiovascular or all-cause death, coronary heart disease, coronary artery disease, peripheral arterial disease, stroke (ischaemic and hemorrhagic), angina pectoris, or cerebrovascular disease and acute coronary syndrome, myocardial infarction and unstable angina. In some embodiments, the formulations described here are useful in reducing the risk of: fatal and nonfatal heart attacks, fatal and non-fatal strokes, certain types of heart surgery, hospitalization for heart failure, chest pain in patients with heart disease, and/or cardiovascular events because of established heart disease such as prior heart attack, prior heart surgery, and/or chest pain with evidence of clogged arteries and/or transplant-related vascular disease. In some embodiments, the formulations described herein are useful in preventing or reducing the cardiovascular risk due to elevated CRP or hsCRP. In some embodiments, the formulations described herein can be used to reduce the risk of recurrent cardiovascular events. Exemplary doses of anti-PCSK9 antibody to treat or prevent cholesterol related disorders range from about 100 mg to about 1200 mg, or about 220 mg to about 450 mg, or about 280 mg to about 450 mg of anti-PCSK9 antibody or 1 mg/kg to about 16 mg/kg, or about 3 mg/kg to 10 mg/k, or about 5-7 mg/kg body weight of anti-PCSK9 antibody.

As will be appreciated by one of skill in the art, diseases or disorders that are generally addressable (either treatable or preventable) through the use of statins can also benefit from the application of the formulations described herein. In addition, in some embodiments, disorders or disease that can benefit from the prevention of cholesterol synthesis or increased LDLR expression can also be treated by the formulations described herein. In addition, as will be appreciated by one of skill in the art, the use of the formulations described herein can be especially useful in the treatment of diabetes. Not only is diabetes a risk factor for coronary heart disease, but insulin increases the expression of PCSK9. That is, people with diabetes have elevated plasma lipid levels (which can be related to high PCSK9 levels) and can benefit from lowering those levels. This is generally discussed in more detail in Costet et al. ("Hepatic PCSK9 Expression is Regulated by Nutritional Status via Insulin and Sterol Regulatory Element-binding Protein 1C", J. Biol. Chem., 281: 6211-6218, 2006), the entirety of which is incorporated herein by reference.

In another aspect, described herein are methods of lowering the serum LDL cholesterol level in a mammalian subject comprising administering a crystalline formulation described herein to the mammalian subject in an amount effective to lower serum LDL cholesterol level, as compared to a predose serum LDL cholesterol level. In some embodiments, the serum LDL cholesterol level in the mammalian subject is reduced by at least about 15%, 20%, 25%, 30%, 35%. 40%, 45%, 50%, 55%, 60%, 65%, 70%, 75%, 80%, 85%, 90% or more, as compared to a predose serum LDL cholesterol level. In some embodiments the serum LDL cholesterol level is reduced and the reduction is sustained for a period of at least about 7 days, 2 weeks, 3 weeks, 4 weeks, 1 month, 5 weeks, 6 weeks, 7 weeks, 8 weeks, 2 months, 3 months or longer.

In another aspect, described herein are methods of lowering the PCSK9 values in a mammalian subject comprising administering a crystalline formulation described herein to the mammalian subject in an amount effective to lower PCSK9 values, as compared to a predose PCSK9 value. In some embodiments, the PCSK9 value in the mammalian subject is reduced by at least about 60%, 65%, 70%, 75%, 80%, 85%, 90% or more, as compared to a predose PCSK9 value. In some embodiments the PCSK9 value is reduced and the reduction is sustained for a period of at least about 7 days, 2 weeks, 3 weeks, 4 weeks, 1 month, 5 weeks, 6 weeks, 7 weeks, 8 weeks, 2 months, 3 months or longer.

In another aspect, described herein are methods of lowering the total cholesterol level in a mammalian subject comprising administering a crystalline formulation described herein to the mammalian subject in an amount effective to lower total cholesterol level, as compared to a predose total cholesterol level. In some embodiments, the total cholesterol level in the mammalian subject is reduced by at least about 20%, 25%, 30%, 35%, 40%, 45%, 50%, 55%, 60% or more, as compared to a predose total cholesterol level. In some embodiments the total cholesterol level is reduced and the reduction is sustained for a period of at least about 7 days, 2 weeks, 3 weeks, 4 weeks, 1 month, 5 weeks, 6 weeks, 7 weeks, 8 weeks, 2 months, 3 months or longer.

In another aspect, described herein are methods of lowering the non-HDL cholesterol level in a mammalian subject comprising administering a crystalline formulation described herein to the mammalian subject in an amount effective to lower non-HDL cholesterol level, as compared to a predose non-HDL cholesterol level. In some embodiments, the total cholesterol level in the mammalian subject is reduced by at least about 30%, 35%, 40%, 45%, 50%, 55%, 60%, 65%, 70%, 75%, 80%, 85% or more, as compared to a predose non-HDL cholesterol level. In some embodiments the non-HDL cholesterol level is reduced and the reduction is sustained for a period of at least about 7 days, 2 weeks, 3 weeks, 4 weeks, 1 month, 5 weeks, 6 weeks, 7 weeks, 8 weeks, 2 months, 3 months or longer.

In another aspect, described herein are methods of lowering the ApoB level in a mammalian subject comprising administering a crystalline formulation described herein to the mammalian subject in an amount effective to lower the ApoB level, as compared to a predose ApoB level. In some embodiments, the ApoB level in the mammalian subject is reduced by at least about 20%, 25%, 30%, 35%, 40%, 45%, 50%, 55%, 60%, 65%, 70%, 75%, or more, as compared to a predose ApoB level. In some embodiments the ApoB level is reduced and the reduction is sustained for a period of at least about 7 days, 2 weeks, 3 weeks, 4 weeks, 1 month, 5 weeks, 6 weeks, 7 weeks, 8 weeks, 2 months, 3 months or longer.

In another aspect, described herein are methods of lowering the Lipoprotein A ("Lp(a)") level in a mammalian subject comprising administering a crystalline formulation described herein to the mammalian subject in an amount effective to lower the Lp(a) level, as compared to a predose Lp(a) level. In some embodiments, the Lp(a) level in the mammalian subject is reduced by at least about 20%, 25%, 30%, 35%, 40%, 45%, 50%, 55%, 60%, 65%, or more, as compared to a predose Lp(a) level. In some embodiments the Lp(a) level is reduced and the reduction is sustained for a period of at least about 7 days, 2 weeks, 3 weeks, 4 weeks, 1 month, 5 weeks, 6 weeks, 7 weeks, 8 weeks, 2 months, 3 months or longer.

It should be understood that while various embodiments in the specification are presented using "comprising" language, under various circumstances, a related embodiment may also be described using "consisting of" or "consisting essentially of" language. It is to be noted that the term "a" or "an", refers to one or more, for example, "an immunoglobulin molecule," is understood to represent one or more immunoglobulin molecules. As such, the terms "a" (or "an"), "one or more," and "at least one" can be used interchangeably herein.

It should also be understood that when describing a range of values, the characteristic being described could be an individual value found within the range. For example, "a pH from about pH 4 to about pH 6," could be, but is not limited to, pH 4, 4.2, 4.6, 5.1, 5.5, etc. and any value in between such values. Additionally, "a pH from about pH 4 to about pH 6," should not be construed to mean that the pH of a formulation in question varies 2 pH units in the range from pH 4 to pH 6 during storage, but rather a value may be picked in that range for the pH of the solution, and the pH remains buffered at about that pH. In some embodiments, when the term "about" is used, it means the recited number plus or minus 5%, 10%, 15% or more of that recited number. The actual variation intended is determinable from the context.

In any of the ranges described herein, the endpoints of the range are included in the range. However, the description also contemplates the same ranges in which the lower and/or the higher endpoint is excluded. Additional features and variations of the invention will be apparent to those skilled in the art from the entirety of this application, including the drawing and detailed description, and all such features are intended as aspects of the invention. Likewise, features of the invention described herein can be re-combined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention.

BRIEF DESCRIPTION OF THE FIGURES

FIG. 1A depicts an amino acid sequence of the mature form of the PCSK9 with the pro-domain underlined.

FIG. $1B_1$-$1B_4$ depict amino acid and nucleic acid sequences of PCSK9 with the pro-domain underlined and the signal sequence in bold.

FIGS. 2A and 2B depict the amino acid and nucleic acid sequences for the variable domains of antibody, 21B12, CDRs are underlined and/or boxed.

FIG. 3 depicts the amino acid sequences for various constant domains.

FIGS. 4A and 4B depict the amino acid sequences for mature heavy chains and mature light chains of antibody, 21B12.

DETAILED DESCRIPTION OF THE INVENTION

Described herein are crystals of anti-PCSK9 immunoglobulin type G (IgG) antibodies. In some embodiments, the crystals of anti-PCSK9 immunoglobulin type G (IgG) antibodies are suitable for use in crystalline formulations for parenteral administration. In some embodiments, the crystals of anti-PCSK9 immunoglobulin type G (IgG) antibodies are suitable for purification and drug substance storage. Also described herein are methods of using such crystals of anti-PCSK9 immunoglobulin type G (IgG) antibodies to prepare crystalline formulations for use as medicaments; formulations comprising high concentrations of a crystalline anti-PCSK9 antibodies, methods of using these formulations for treatment, methods of administering these formulations, e.g. subcutaneously or intramuscularly, and containers or kits comprising these formulations.

I. Antibodies in the Formulation

In some embodiments, the anti-PCSK9 antibody in the formulation is present at a concentration (a "high protein concentration") of at least about 100 mg/ml, about 101 mg/ml, about 102 mg/ml, about 103 mg/ml, about 104 mg/ml, about 105 mg/ml, about 106 mg/ml, about 107 mg/ml, about 108 mg/ml, about 109 mg/ml, about 110 mg/ml, about 111 mg/ml, about 112 mg/ml, about 113 mg/ml, about 114 mg/ml, about 115 mg/ml, about 116 mg/ml, about 117 mg/ml, about 118 mg/ml, about 119 mg/ml, about 120 mg/ml, about 121 mg/ml, about 122 mg/ml, about 123 mg/ml, about 124 mg/ml, about 125 mg/ml, about 126 mg/ml, about 127 mg/ml, about 128 mg/ml, about 129 mg/ml, about 130 mg/ml, about 131 mg/ml, about 132 mg/ml, about 132 mg/ml, about 133 mg/ml, about 134 mg/ml, about 135 mg/ml, about 136 mg/ml, about 137 mg/ml, about 138 mg/ml, about 139 mg/ml, about 140 mg/ml, about 141 mg/ml, about 142 mg/ml, about 143 mg/ml, about 144 mg/ml, about 145 mg/ml, about 146 mg/ml, about 147 mg/ml, about 148 mg/ml, about 149 mg/ml, about 150 mg/ml, about 151 mg/ml, about 152 mg/ml, about 153 mg/ml, about 154 mg/ml, about 155 mg/ml, about 156 mg/ml, about 157 mg/ml, about 158 mg/ml, about 159 mg/ml, about 160 mg/ml, about 161 mg/ml, about 162 mg/ml, about 163 mg/ml, about 164 mg/ml, about 165 mg/ml, about 166 mg/ml, about 167 mg/ml, about 168 mg/ml, about 169 mg/ml, about 170 mg/ml, about 171 mg/ml, about 172 mg/ml, about 173 mg/ml, about 174 mg/ml, about 175 mg/ml, about 176 mg/ml, about 177 mg/ml, about 178 mg/ml, about 179 mg/ml, about 180 mg/ml, about 181 mg/ml, about 182 mg/ml, about 183 mg/ml, about 184 mg/ml, about 185 mg/ml, about 186 mg/ml, about 187 mg/ml, about 188 mg/ml, about 189 mg/ml, about 190 mg/ml, about 191 mg/ml, about 192 mg/ml, about 193 mg/ml, about 194 mg/ml, about 195 mg/ml, about 196 mg/ml, about 197 mg/ml, about 198 mg/ml, about 199 mg/ml, about 200 mg/ml, about 201 mg/ml, about 202 mg/ml, about 203 mg/ml, about 204 mg/ml, about 205 mg/ml, about 206 mg/ml, about 207 mg/ml, about 208 mg/ml, about 209 mg/ml, about 210 mg/ml, about 211 mg/ml, about 212 mg/ml, about 213 mg/ml, about 214 mg/ml, about 215 mg/ml, about 216 mg/ml, about 217 mg/ml, about 218 mg/ml, about 219 mg/ml, about 220 mg/ml, about 221 mg/ml, about 222 mg/ml, about 223 mg/ml, about 224 mg/ml, about 225 mg/ml, about 226 mg/ml, about 227 mg/ml, about 228 mg/ml, about 229 mg/ml, about 230 mg/ml, about 231 mg/ml, about 232 mg/ml, about 232 mg/ml, about 233 mg/ml, about 234 mg/ml, about 235 mg/ml, about 236 mg/ml, about 237 mg/ml, about 238 mg/ml, about 239 mg/ml, about 240 mg/ml, about 241 mg/ml, about 242 mg/ml, about 243 mg/ml, about 244 mg/ml, about 245 mg/ml, about 246 mg/ml, about 247 mg/ml, about 248 mg/ml, about 249 mg/ml, about 250 mg/ml, and may range up to e.g., about 450 mg/ml, about 440 mg/ml, 430 mg/ml, 420 mg/ml, 410 mg/ml, 400 mg/ml, about 390 mg/ml, about 380 mg/ml, about 370 mg/ml, about 360 mg/ml, about 350 mg/ml, about 340 mg/ml, about 330 mg/ml, about 320 mg/ml, about 310 mg/ml, about 300 mg/ml, about 290 mg/ml, about 280 mg/ml, about 270 mg/ml, or about 260 mg/ml. Any range featuring a combination of the foregoing endpoints is contemplated, including but not limited to: about 70 mg/ml to about 250 mg/ml, about 100 mg/ml to about 250 mg/ml, about 150 mg/ml to about 250 mg/ml, about 150 mg/ml to about 300 mg/ml, about 150 mg/ml to about 320 mg/ml or about 150 mg/ml to about 350 mg/ml.

In some embodiments, the anti-PCSK9 antibody is antibody 21B12. Antibody 21B12 was previously described in U.S. Pat. No. 8,030,457, the disclosure of which including sequence listing is incorporated herein by reference in its entirety.

The anti-PCSK9 antibody described herein binds to PCSK9 of SEQ ID NO: 1 with a KD of $10^{-6}$ or less, or $10^{-7}$ or less, or $10^{-8}$ or less, or $10^{-9}$ or less (lower numbers meaning higher binding affinity). Affinity can be determined by any means known in the art, including via Biacore technology.

The term "21B12 antibody" as used herein refers to an IgG immunoglobulin composed of two light chains and two heavy chains, wherein the light chain comprises a light chain complementarity region (CDR) of the CDRL1 sequence in SQ ID NO:9, a CDRL2 of the CDRL2 sequence in SQ ID NO:9, and a CDRL3 of the CDRL3 sequence in SQ ID NO:9, and the heavy chain comprises a heavy chain complementarity determining region (CDR) of the CDRH1 sequence in SEQ ID NO:5, a CDRH2 of the CDRH2 sequence in SEQ ID NO:5, and a CDRH3 of the CDRH3 sequence in SEQ ID NO:5. In some other embodiments, the antibody is an IgG comprising a light chain complementarity region (CDR) of the CDRL1 sequence in SEQ ID NO:11, a CDRL2 of the CDRL2 sequence in SEQ ID NO:11, and a CDRL3 of the CDRL3 sequence in SEQ ID NO:11, and a heavy chain complementarity determining region (CDR) of the CDRH1 sequence in SEQ ID NO:7, a CDRH2 of the CDRH2 sequence in SEQ ID NO:7, and a CDRH3 of the CDRH3 sequence in SEQ ID NO:7. In some embodiments, the 21B12 antibody comprises the amino acid sequences of: SEQ ID NO:24 (21B12 CDRL1), and SEQ ID NO:25 (21B12 CDRL2), and SEQ ID NO:26 (21B12 CDRL3) and SEQ ID NO:20 or SEQ ID NO:21 (21B12 CDRH1), and SEQ ID NO:22 (21B12 CDRH2), and SEQ ID NO:23 (21B12 CDRH3).

In some embodiments, the anti-PCSK9 IgG antibody comprises the heavy and light chain variable regions of an antibody having at least 70%, at least 80%, at least 90%, at least 95%, at least 98%, at least 99% sequence identity to antibody, 21B12. Thus, in some embodiments, the antibody is an IgG comprising a light chain variable region comprising an amino acid sequence that is at least 70% identical to that of SEQ ID NO:9 or SEQ ID NO:11 and a heavy chain variable region that comprises an amino acid sequence that is at least 70% identical to that of SEQ ID NO:5 or SEQ ID NO:7. In some embodiments, the antibody is an IgG comprising a light chain variable region comprising an amino acid sequence that is at least 80% identical to that of SEQ ID NO:9 or SEQ ID NO:11 and a heavy chain variable region that comprises an amino acid sequence that is at least 80% identical to that of SEQ ID NO:5 or SEQ ID NO:7. In some embodiments, the antibody is an IgG comprising a light chain variable region comprising an amino acid sequence that is at least 90% identical to that of SEQ ID NO:9 or SEQ ID NO:11 and a heavy chain variable region that comprises an amino acid sequence that is at least 90% identical to that of SEQ ID NO:5 or SEQ ID NO:7. In some embodiments, the antibody is an IgG comprising a light chain variable region comprising an amino acid sequence that is at least 95% identical to that of SEQ ID NO:9 or SEQ ID NO:11 and a heavy chain variable region that comprises an amino acid sequence that is at least 95% identical to that of SEQ ID NO:5 or SEQ ID NO:7. In some embodiments, the antibody is an IgG comprising a light chain variable region comprising an amino acid sequence that is at least 98% identical to that of SEQ ID NO:9 or SEQ ID NO:11 and a heavy chain variable region that comprises an amino acid sequence that is at least 98% identical to that of SEQ ID NO:5 or SEQ ID NO:7. In some embodiments, the antibody is an IgG comprising a light chain variable region comprising an amino acid sequence that is at least 99% identical to that of SEQ ID NO:9 or SEQ ID NO:11 and a heavy chain variable region that comprises an amino acid sequence that is at least 99% identical to that of SEQ ID NO:5 or SEQ ID NO:7.

In some embodiments, the light chain of the 21B12 antibody comprises the amino acid sequence of SEQ ID NO:9 or SEQ ID NO:11 (21B12 light chain variable region) and the heavy chain of the 21B12 antibody comprises the amino acid sequence of SEQ ID NO:5 or SEQ ID NO:7 (21B12 heavy chain variable domain). In some embodiments, the light chain of the 21B12 antibody comprises the amino acid sequence of SEQ ID NO:9 (21B12 light chain variable region) and heavy chain of the 21B12 antibody comprises the amino acid sequence of SEQ ID NO:5 (21B12 heavy chain variable region). In some embodiments, the light chain of the 21B12 antibody comprises the amino acid sequence of SEQ ID NO:11 (21B12 light chain variable region) and heavy chain of the 21B12 antibody comprises the amino acid sequence of SEQ ID NO:7 (21B12 heavy chain variable region). In some embodiments, the light chain variable region is fused to a light chain constant region, and the heavy chain variable region is fused to an IgG constant region. In some embodiments, the 21B12 antibody comprises the heavy and/or light chain variable region of antibody 21B12, SEQ ID NO:5 (21B12 heavy chain variable region) fused to a human heavy chain constant region of isotype IgG1, 2, 3 or 4 (e.g., native, consensus or modified, and a number of modifications that are known not to affect binding are known in the art), and/or SEQ ID NO:9 (21B12 light chain variable region) fused to a human light chain constant region (e.g., native, consensus or modified and a number of modifications that are known not to affect binding are known in the art), or SEQ ID NO:7 (21B12 heavy chain variable region) fused to a human heavy chain constant region of isotype IgG1, 2, 3 or 4, and/or SEQ ID NO:11 (21B12 light chain variable region) fused to a human light chain constant region. In some embodiments, the antibody comprises the mature heavy and light chains of antibody 21B12, (SEQ ID NO:16 or 17, 21B12 mature light chain and SEQ ID NO:18 or 19, 21B12 mature heavy chain). In some embodiments, the antibody comprises SEQ ID NO:16 and SEQ ID NO:18. In some embodiments, the antibody comprises SEQ ID NO:17 and SEQ ID NO:19.

In some embodiments, the antibody comprises amino acid sequences obtainable by expressing in mammalian host cells the cDNA encoding the heavy and/or light chain, or alternatively the heavy and/or light chain variable region, of antibody 21B12. The term "antibody" refers to an intact immunoglobulin, e.g. in the case of IgG a tetrameric immunoglobulin composed of two heavy chains and two light chains. (e.g., chimeric, humanized, or human versions preferably having full length heavy and/or light chains, optionally with mutations within the framework or constant regions that retain the anti-PCSK9 binding properties).

An "isolated" antibody refers to an antibody, as that term is defined herein, that has been identified and separated from a component of its natural environment. Contaminant components of its natural environment are materials that would interfere with diagnostic or therapeutic uses for the antibody, and may include enzymes, hormones, and other proteinaceous or nonproteinaceous solutes. In certain embodiments, the antibody will be purified (1) to greater than 95% by weight of antibody, and most preferably more than 99% by weight, (2) to a degree sufficient to obtain at least 15 residues of N-terminal or internal amino acid sequence, or (3) to homogeneity by SDS-PAGE under reducing or nonreducing conditions using Coomassie blue or, preferably, silver stain. Isolated naturally occurring antibody includes the antibody in situ within recombinant cells since at least one component of the antibody's natural environment will not be present. Ordinarily, however, isolated antibody will be prepared by at least one purification step.

A "monoclonal" antibody refers to an antibody obtained from a population of substantially homogeneous antibodies, i.e., the individual antibodies comprising the population are identical except for possible naturally occurring mutations that may be present in minor amounts, compared to a "polyclonal" antibody which refers to a mixed population of antibodies of diverse sequence that bind diverse epitopes. The phrase "humanized antibody" refers to an antibody derived from a sequence of a non-human antibody, typically a rodent monoclonal antibody, which comprises modifications that render the sequence more human-like. Alternatively, a humanized antibody may be derived from a chimeric antibody. The phrase "human" antibody refers to an antibody derived from human sequences, e.g. through screening libraries of human antibody genes through known techniques such as phage display, or produced using transgenic animals that have no endogenous immunoglobulin production and are engineered to contain human immunoglobulin loci.

An "immunoglobulin G" or "native IgG antibody" is a tetrameric glycoprotein. In a naturally-occurring immunoglobulin, each tetramer is composed of two identical pairs of polypeptide chains, each pair having one "light" (about 25 kDa) and one "heavy" chain (about 50-70 kDa). The amino-terminal portion of each chain includes a "variable" ("V") region of about 100 to 110 or more amino acids primarily responsible for antigen recognition. The carboxy-terminal portion of each chain defines a constant region primarily responsible for effector function Immunoglobulins can be assigned to different classes depending on the amino acid sequence of the constant domain of their heavy chains. Heavy chains are classified as mu ($\mu$), delta ($\Delta$), gamma ($\gamma$), alpha ($\alpha$), and epsilon ($\epsilon$), and define the antibody's isotype as IgM, IgD, IgG, IgA, and IgE, respectively. Several of these may be further divided into subclasses or isotypes, e.g. IgG1, IgG2, IgG3, IgG4, IgA1 and IgA2. Different isotypes have different effector functions; for example, IgG1 and IgG3 isotypes have antibody-dependent cellular cytotoxicity (ADCC) activity. Human light chains are classified as kappa ($\kappa$) and lambda ($\lambda$) light chains. Within light and heavy chains, the variable and constant regions are joined by a "J" region of about 12 or more amino acids, with the heavy chain also including a "D" region of about 10 more amino acids. See generally, Fundamental Immunology, Ch. 7 (Paul, W., ed., 2nd ed. Raven Press, N.Y. (1989)).

The term "hypervariable" region refers to amino acid residues from a complementarity determining region or CDR (i.e., residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, 5th Ed. Public Health Service, National Institutes of Health, Bethesda, Md. (1991)). "Framework" or FR residues are those variable region residues other than the hypervariable region residues.

The term "variant" when used in connection with antibodies refers to a polypeptide sequence of an antibody that contains at least one amino acid substitution, deletion, or insertion in the variable region or the portion equivalent to the variable region, provided that the variant retains the desired binding affinity or biological activity. In addition, the antibodies as described herein may have amino acid modifications in the constant region to modify effector function of the antibody, including half-life or clearance, ADCC and/or CDC activity. Such modifications can enhance pharmacokinetics or enhance the effectiveness of the antibody in treating cancer, for example. See Shields et al., J. Biol. Chem., 276(9):6591-6604 (2001), incorporated by reference herein in its entirety. In the case of IgG1, modifications to the constant region, particularly the hinge or CH2 region, may increase or decrease effector function, including ADCC and/or CDC activity. In other embodiments, an IgG2 constant region is modified to decrease antibody-antigen aggregate formation. In the case of IgG4, modifications to the constant region, particularly the hinge region, may reduce the formation of half-antibodies.

The term "modification" when used in connection with antibodies or polypeptides described herein, includes but is not limited to, one or more amino acid change (including substitutions, insertions or deletions); chemical modifications that do not interfere with PCSK9-binding activity; covalent modification by conjugation to therapeutic or diagnostic agents; labeling (e.g., with radionuclides or various enzymes); covalent polymer attachment such as pegylation (derivatization with polyethylene glycol) and insertion or substitution by chemical synthesis of non-natural amino acids. In some embodiments, modified polypeptides (including antibodies) of the invention will retain the binding properties of unmodified molecules of the invention.

The term "derivative" when used in connection with antibodies or polypeptides of the invention refers to antibodies or polypeptides that are covalently modified by conjugation to therapeutic or diagnostic agents, labeling (e.g., with radionuclides or various enzymes), covalent polymer attachment such as pegylation (derivatization with polyethylene glycol) and insertion or substitution by chemical synthesis of non-natural amino acids. In some embodiments, derivatives of the invention will retain the binding properties of underivatized molecules of the invention.

Proteins and non-protein agents may be conjugated to the antibodies by methods that are known in the art. Conjugation methods include direct linkage, linkage via covalently attached linkers, and specific binding pair members (e.g., avidin-biotin). Such methods include, for example, that described by Greenfield et al., Cancer Research 50, 6600-6607 (1990) for the conjugation of doxorubicin and those described by Arnon et al., Adv. Exp. Med. Biol. 303, 79-90 (1991) and by Kiseleva et al., Mol. Biol. (USSR) 25, 508-514 (1991) for the conjugation of platinum compounds.

II. Production of Crystals, Crystal Formulations and Compositions

Polypeptide crystals are grown by controlled crystallization of polypeptides from aqueous solutions or from aqueous solutions containing organic solvents or additives. Solution conditions that may be controlled include, for example, the rate of evaporation of solvent, organic solvents or additives, the presence of appropriate co-solutes and buffers, pH, and temperature. A comprehensive review of the various factors affecting the crystallization of proteins has been published by McPherson (1985, Methods Enzymol 114: 112-120). In addition, McPherson and Gilliland (1988, J Crystal Growth, 90: 51-59) have compiled comprehensive lists of polypeptides that have been crystallized, as well as the conditions under which they were crystallized. A compendium of crystals and crystallization recipes, as well as a repository of coordinates of solved protein structures, is maintained by the Protein Data Bank at the Brookhaven National Laboratory (www.rcsb.org/pdb/; Bernstein et al., 1977, J Mol Biol 112: 535-542). It should be noted, however, that the conditions reported in most of the above-cited references have been optimized to yield, in most instances, a few large, diffraction quality crystals. Accordingly, it will be appreciated by those of skill in the art that these conditions vary from protein to protein, and do not provide a high yielding process for the large scale production of crystals of any given polypeptide.

In general, crystals are produced by combining the polypeptide (i.e., antibody) to be crystallized with an appropriate aqueous solvent or aqueous solvent containing appropriate crystallization agents, such as salts or organic solvents or additives (collectively the "crystallization reagent"). The solvent is combined with the polypeptide and may be subjected to agitation at a temperature determined experimentally to be appropriate for the induction of crystallization and acceptable for the maintenance of polypeptide activity and stability. Laboratory-scale methods for crystallization include hanging drop vapor diffusion, sitting drop vapor diffusion, microdialysis, microbatch, under oil, in gel and sandwich drop methods. The solvent can optionally include co-crystallization additives, such as precipitants, fatty acids, reducing agents, glycerol, sulfobetaine, surfactants, polyols, divalent cations, co-factors, or chaotropes, and amino acids as well as buffer species to control pH.

"Co-crystallization additives" include compounds that facilitate crystallization of a polypeptide and/or compounds that stabilize the protein and protect against denaturation. Examples of co-solutes include ammonium acetate, ammonium chloride, ammonium fluoride, ammonium formate, ammonium nitrate, ammonium phosphate, ammonium sulfate, cadmium chloride, cadmium sulfate, calcium acetate, calcium chloride, cesium chloride, cobaltous chloride, $CH_3(CH_2)_{15}N(CH_3)_3{}^+Br.^-$ (CTAB), di-ammonium citrate, di-ammonium hydrogen phosphate, di-ammonium phosphate, di-ammonium tartrate, di-potassium phosphate, di-sodium phosphate, di-sodium tartrate, DL-malic acid, ferric chloride, L-proline, lithium acetate, lithium chloride, lithium nitrate, lithium sulfate, magnesium acetate, magnesium chloride, magnesium formate, magnesium nitrate, magnesium sulfate, n-acyl-alpha amino acids including but not limited to n-acetyl L-arginine, nickel chloride, potassium acetate, potassium bromide, potassium chloride, potassium citrate, potassium fluoride, potassium formate, potassium nitrate, potassium phosphate, potassium sodium tartrate, potassium sulfate, potassium thiocyanate, sodium acetate, sodium bromide, sodium chloride, sodium citrate, sodium fluoride, sodium formate, sodium malonate, sodium nitrate, sodium phosphate, sodium sulfate, sodium thiocyanate, succinic acid, tacsimate, tri-ammonium citrate, tri-lithium citrate, trimethylamine N-oxide, tri-potassium citrate, tri-sodium citrate, zinc acetate, zinc sulfate, and other compounds that function to supply co-solutes. "Crystallization" include compounds that maintain the pH of a solution in a desired range to facilitate crystallization of a polypeptide. Examples include ACES (N-(2-acetamido)-2-aminoethanesulfonic acid), BES (N,N-bis(2-hydroxyethyl)-2-aminoethanesulfonic acid), Bicine (N,N-Bis(2-hydroxyethyl)glycine), BIS-TRIS (2,2-bis-(hydroxymethyl)-2,2',2"-nitrilotriethanol), boric acid, CAPS (3-[cyclohexylamino]-1-propanesulfonic acid), citric acid, EPPS (HEPPS, 4-(2-Hydroxyethyl)piperazine-1-propanesulfonic acid), Gly-Gly ($NH_2CH_2CONHCH_2COOH$, glycyl-glycine), HEPES (4-(2-hydroxyethyl)piperazine-1-ethanesulfonic acid), imidazole, MES (2-morpholinoethanesulfonic acid), MOPS (3-(N-morpholino)-propanesulfonic acid), PIPES (piperazine-1,4-bis(2-ethanesulfonic acid)), potassium chloride, sodium acetate, sodium bicarbonate, sodium phosphate monobasic (sodium dihydrogen phosphate), sodium phosphate dibasic, TAPS(N-[tris-(hydroxymethyl)methyl]-3-aminopropanesulfonic acid), TAPSO(N-[tris(hydroxymethyl)methyl]-3-amino-2-hydroxypropanesulfon-ic acid), TES (N-[tris(hydroxymethyl)methyl]-2-aminoethanesulfonic acid), Tricine (N-[tris(hydroxymethyl)methyl]glycine), Tris-HCl, TRIZMA (2-amino-2-(hydroxymethyl)-1,3-propanediol), and other compounds that function to maintain a solution at or near a specified pH.

The selection of precipitants are one factor affecting crystallization. For example, PEG products, e.g. of molecular weight 200 to 20,000 kD, can be used. PEG3350 is a long polymer precipitant or dehydrant which works by volume exclusion effect. Lyotropic salts, such as ammonium sulfate, promote precipitation processes, as do short-chain fatty acids, such as caprylic acid. Polyionic species also are useful precipitants.

Antibodies for use in formulations for subcutaneous injection, for example, preferably are precipitated at a physiologic pH range and in a crystallization reagent that provides isotonic osmolality.

The need for additives, co-solutes, buffers, etc. and their concentrations are determined experimentally to facilitate crystallization. Some examples of suitable crystallization conditions for a polypeptide are described in Examples 1, 2 and 3 below.

Antibody 21B12 is crystallized under a variety of conditions. Various morphologies of Antibody 21B12 crystals can be grown under scale-up conditions whereby the antibody in a liquid formulation is added to a volume of known crystallization reagent and stored in a sealed container. Antibody 21B12 crystals can be grown under these conditions in less than 24 hours, at room temperature and have been shown to produce between about 30% to about 99%% yield.

In an industrial-scale process, the controlled precipitation leading to crystallization can best be carried out by the simple combination of polypeptide, precipitant, co-solutes and, optionally, buffers in a batch process. As another option, polypeptides may be crystallized by using polypeptide precipitates as the starting material ("seeding"). In this case, polypeptide precipitates are added to a crystallization solution and incubated until crystals form. Alternative laboratory crystallization methods, such as dialysis or vapor diffusion, can also be adopted. McPherson, supra and Gilliland, supra, include a comprehensive list of suitable conditions in their reviews of the crystallization literature. Occasionally, in cases in which the crystallized polypeptide is to be cross-linked, incompatibility between an intended crosslinking agent and the crystallization medium might require exchanging the crystals into a more suitable solvent system.

According to some embodiments, polypeptide crystals, crystal formulations and compositions are prepared by the following process: first, the polypeptide is crystallized. Next, excipients or ingredients as described herein are added directly to the mother liquor. Alternatively, the crystals are suspended in a solution of excipient or other formulary ingredients, after the mother liquor is removed, for a minimum of 1 hour to a maximum of 24 hours. The excipient concentration is typically between about 0.01 to 30% w/w, which corresponds to a polypeptide crystal concentration of 99.99 to 70% w/w, respectively. In one embodiment, the excipient concentration is between about 0.1 to 10%, which corresponds to a crystal concentration of 99.9 to 90% w/w, respectively. The mother liquor can be removed from the crystal slurry either by filtration, buffer exchange, or by centrifugation. Subsequently, the crystals are washed with any isotonic injectable vehicle as long as the these vehicles do not dissolve the crystals, optionally with solutions of 50 to 100% of one or more organic solvents or additives such as, for example, ethanol, methanol, isopropanol or ethyl acetate, or polyethelene glycol (PEG), either at room temperature or at temperatures between −20° C. to 25° C. In addition, water can be used to wash the crystals. The crystals are the dried either by passing a stream of nitrogen, air, or inert gas over the crystals. Finally, micronizing of the crystals can be performed if necessary. The drying of polypeptide crystals is the removal of water, organic solvent or additive, or liquid polymer by means including drying with $N_2$, air, or inert gases; vacuum oven drying; lyophilization; washing with a volatile organic solvent or additive followed by evaporation of the solvent; or evaporation in a fume hood. Typically, drying is achieved when the crystals become a free-flowing powder. Drying may be carried out by passing a stream of gas over wet crystals. The gas may be selected from the group consisting of: nitrogen, argon, helium, carbon dioxide, air or combinations thereof. The diameter of the particles achieved can be in the range of 0.1 to 100 micrometers, or in the range of 0.2 to 10 micrometers, or in the range of 10 to 50 micrometers, or in the range of 0.5 to 2 micrometers. For formulations to be administered by inhalation, in one embodiment the particles formed from the polypeptide crystals are in the range of 0.5 to 1 micrometers.

According to some embodiments, when preparing protein crystals, protein crystal formulations or compositions, enhancers, such as surfactants are not added during crystallization. According to some other embodiments, when preparing protein crystals, protein crystal formulations or compositions, enhancers, such as surfactants are added during crystallization. Excipients or ingredients are added to the mother liquor after crystallization, at a concentration of between about 1-10% w/w, alternatively at a concentration of between about 0.1-25% w/w, alternatively at a concentration of between about 0.1-50% w/w. These concentrations correspond to crystal concentrations of 99-90% w/w, 99.9-75% w/w and 99.9-50% w/w, respectively. The excipient or ingredient is incubated with the crystals in the mother liquor for about 0.1-3 hrs, alternatively the incubation is carried out for 0.1-12 hrs, alternatively the incubation is carried out for 0.1-24 hrs.

In some or any embodiments, the ingredient or excipient is dissolved in a solution other than the mother liquor, and the protein crystals are removed from the mother liquor and suspended in the excipient or ingredient solution. In some embodiments, the excipient or ingredient solution (or resuspension vehicle) is a mixture of excipients or ingredients or surfactants that is isotonic and injectable. In some embodiments, the excipient or ingredient solution (or resuspension vehicle) is not a mixture of excipients or ingredients or surfactants that is isotonic and injectable. The ingredient or excipient concentrations and the incubation times are the same as those described above.

Polypeptide Crystals

As used herein, "crystal" or "crystalline" refers to one form of the solid state of matter, which is distinct from a second form—the amorphous solid state. Crystals display characteristic features including a lattice structure, characteristic shapes, and optical properties such as refractive index and birefringence. A crystal consists of atoms arranged in a pattern that repeats periodically in three dimensions (C. S. Barrett, Structure of Metals, 2nd ed., McGraw-Hill, New York, 1952, p. 1). In contrast, amorphous material is a non-crystalline solid form of matter, sometimes referred to as an amorphous precipitate. Such precipitates have no molecular lattice structure characteristic of the crystalline solid state and do not display birefringence or other spectroscopic characteristics typical of the crystalline forms of matter.

Polypeptide crystals are polypeptide molecules arranged in a crystal lattice. Polypeptide crystals contain a pattern of specific polypeptide-polypeptide interactions that are repeated periodically in three dimensions. The polypeptide crystals of this invention are to be distinguished from amorphous solid forms or precipitates of polypeptides, such as those obtained by lyophilizing a polypeptide solution.

In polypeptide crystals, the polypeptide molecules form asymmetric units which are arranged together to form symmetric units. The geometric structure of the symmetric units of polypeptide crystals can be, for example, cubic, hexagonal, monoclinic, orthorhombic, tetragonal, triclinic, or trigonal. The overall structure of the crystals in their entirety can be, for example, in the form of bipyramids, cubes, needles, plates, prisms, rhomboids, rods, or spheres, or combinations thereof. Other observed forms include block-shaped, UFO shaped, football shaped, leaf shaped, wheat shaped, singlet shaped, feather-shaped, straw-shaped, chrysanthemum-shaped, spherical or mixtures thereof. In some embodiments, the crystals are observed in clusters. Crystals that are of the "cubic" structural class can more specifically have octadecahedral or dodecahedral crystal forms. The diameter of the crystals is defined as the Martin's diameter. It is measured as the length of the line, parallel to the ocular scale, that divides the randomly oriented crystals into two equal projected areas. Crystals in forms such as needles or rods will also have a maximal dimension that is referred to herein as the length of the crystal. The crystals are also characterized by x-ray diffraction.

Testing Properties of Crystalline Polypeptides

After polypeptide crystals are formed, they can be subjected to various analyses to confirm their polypeptide content and to further examine their physical structure. For example, if necessary individual crystals can be removed from the crystallization solution and washed with aqueous or organic solvents or additives, then dried (for example, by air drying, by passing a stream of inert gas over the crystal, by lyophilization, or by vacuum). Crystals can be isolated, removed from the crystal growth drop, and then mounted for X-ray diffraction.

Crystals can also be characterized by a variety of means described in the art. See, e.g., Basu et al., Expert Opin. Biol. Thera. 4, 301-317 (2004), incorporated herein by reference in its entirety for its disclosure of protein crystal production and formulation procedures, and analytical tools for characterizing crystals and their component protein. While powder X-ray diffraction is commonly used to identify crystalline material, it requires very large and perfect protein crystals and is not commonly applied to the protein microcrystals typically used in crystalline formulations. Electron diffraction and solid state nuclear magnetic resonance (ss-NMR) can be applied to characterize crystals. Crystal size, shape and morphology (e.g. surface morphology) can be inspected, for example, by light microscopy, transmission electron microscopy, scanning electron microscopy, atomic force microscopy, and/or light scattering (e.g. photon correlation spectroscopy or DLS, low angle laser light scattering or LAALS). Total surface area and porosity of crystals can also be characterized. Mass spectrometry, micro-attenuated total reflectance Fourier transform infrared spectroscopy (FTIR) and/or differential scanning calorimetry (DSC) can provide information about protein primary and secondary structure.

As another example, polypeptide crystals can be removed from crystallization solution and washed or rinsed, or the majority of crystallization solution can be removed from the crystals and replaced with a different solution. In this way, the particular salt that was using in the crystallization procedure can be replaced in the crystal lattice with a different salt. In one embodiment of the invention, crystallized Antibody 21B12 is separated from the crystallization buffer and placed in a solution containing a salt of sodium, potassium, or magnesium (for example, sodium acetate, sodium chloride, sodium citrate, sodium phosphate, sodium sulfate, potassium chloride, potassium citrate, or magnesium sulfate). For X-ray diffraction, the replacement solution can contain heavy atoms useful in determining the atomic coordinates of the crystallized polypeptide.

In a further example, polypeptide crystals can be removed from crystallization solution and solubilized in an appropriate buffer for further testing, such as an SDS-containing buffer for analysis of the polypeptide that had been crystallized by gel electrophoresis. Methods for analysis of proteins by gel electrophoresis are well known and include staining a gel with silver or Coomassie blue dye, and comparing the electrophoretic migration of the polypeptide that had been crystallized with the migration of polypeptide markers of known molecular weight. In another method, the polypeptide is visualized in the gel by use of a labeled antibody that specifically binds to the polypeptide. Polypeptides that have been crystallized can also be solubilized in buffers appropriate for amino acid sequencing by Edman degradation, for mass spectrometry, for other spectrographic scattering, refraction, diffraction, or absorption studies, or for labeling of the polypeptide by attachment of a label molecule to the polypeptide.

III. Formulations for Therapeutic Administration

As used herein, the term "composition" as used herein means a mixture comprising at least two components. In particular, described herein are compositions comprising a crystalline anti-PCSK9 antibody, or prepared using a crystalline anti-PCSK9 antibody. In some embodiments, the composition or formulation comprising or prepared using a crystalline anti-PCSK9 antibody is prepared such that it is suitable for injection and/or administration to a patient in need thereof. Compositions to be administered for pharmaceutical purposes to patients are substantially sterile and do not contain any agents that are unduly toxic or infectious to the recipient.

In some embodiments, crystalline anti-PCSK9 antibodies, such as crystalline antibody 21B12, are administered in the form of a physiologically acceptable composition (also referred to herein as a pharmaceutical composition or as a pharmaceutical formulation) comprising a crystalline anti-PCSK9 antibody that is formulated with one or more of the following: physiologically acceptable carriers, excipients, or diluents. Such carriers, excipients, or diluents are nontoxic to recipients at the dosages and concentrations employed. Ordinarily, the preparation of such compositions entails combining the crystalline anti-PCSK9 antibody with one or more of the following: buffers, antioxidants such as ascorbic acid, low molecular weight polypeptides (such as those having fewer than 10 amino acids), proteins, amino acids such as Leucine, Proline, Alanine, Valine, Glycine, Serine, Asparagine, Glutamine, Aspartic acid, Glutamic acid, Methionine, Tryptophan, Phenylalanine, Isoleucine, Threonine, Cysteine, Tyrosine, Histidine, Lysine and Arginine, carbohydrates such as glucose, sucrose or dextrins, chelating agents such as EDTA, glutathione and other stabilizers and excipients. In liquid formulations, neutral buffered saline or saline mixed with nonspecific serum albumin are exemplary appropriate diluents. In accordance with appropriate industry standards, preservatives may also be added, such as benzyl alcohol. Further examples of components that may be employed in pharmaceutical formulations are presented in Remington's Pharmaceutical Sciences, 16$^{th}$ Ed., Mack Publishing Company, Easton, Pa., 1980, and in the Handbook of Pharmaceutical Excipients, published jointly by the American Pharmaceutical Association and the Pharmaceutical Society of Great Britain.

In one embodiment, it is contemplated that the formulation described herein is prepared in a bulk formulation and as such, the components of the pharmaceutical composition are adjusted so that they are higher than would be required for administration, and are diluted appropriately prior to administration.

The antibody crystals described herein can be formulated as a solid crystalline or powder formulation in forms suitable for storage and handling, and in forms suitable for inhalation or pulmonary administration, for example in the form of powders for the preparation of aerosol formulations. In an further embodiment, the antibody crystals can be formulated in a liquid solution of such crystals, or in a slurry of such crystals. In another embodiment, the antibody crystals are used to prepare a liquid formulation, such as an aqueous formulation, for therapeutic administration.

A. Solid Crystalline Formulations

Solid formulations of antibody crystals include crystals that have been substantially isolated from liquid solution or dried, and are present as free crystals or as particles in for example powder form. In the present context the expression "powder" refers to a collection of essentially dry particles, i.e. the moisture content being below about 10% by weight, or below 6% by weight, or below 4% by weight. Polypeptide crystals or powders can be optionally combined with carriers or surfactants. Suitable carrier agents include 1) carbohydrates, e.g. monosaccharides such as fructose, galactose, glucose, sorbose, and the like; 2) disaccharides, such as lactose, trehalose and the like; 3) polysaccharides, such as raffinose, maltodextrins, dextrans, and the like; 4) alditols, such as mannitol, xylitol, and the like; 5) inorganic salts, such as sodium chloride, and the like; and 6) organic salts, such as sodium citrate, sodium ascorbate and the like. In certain embodiments, the carrier is selected from the group consisting of trehalose, raffinose, mannitol, sorbitol, xylitol, inositol, sucrose, sodium chloride, and sodium citrate. Surfactants can be selected from the group consisting of salts of fatty acids, bile salts, phospholipids or polysorbates. Fatty acids salts include salts of $C_{10-14}$ fatty acids, such as sodium caprate, sodium laurate, and sodium myristate. Bile salts include salts of ursodeoxycholate, taurocholate, glycocholate, and taurodihydrofusidate. Polysorbates include polysorbate 20 and polysorbate 80. In one embodiment, the surfactant is a salt of taurocholate such as sodium taurocholate. Phospholipids that can be used as surfactants include lysophosphatidylcholine. In one embodiment, the surfactant is polysorbate 20, and in another embodiment, the surfactant is polysorbate 80.

B. Crystals in Solution or Slurries

Also described herein is a method for rendering polypeptide crystals suitable for storage in suspensions comprising replacing the crystallization buffer (the mother liquor) with a non-aqueous solvent. In yet another embodiment, the crystalline slurry can be rendered solid by spinning out the first solvent and washing the remaining crystalline solid using a second organic solvent or additive to remove water, followed by evaporation of the non-aqueous solvent. Non-aqueous slurries of crystalline therapeutic proteins are especially useful for subcutaneous delivery.

In one such embodiment, the polypeptide crystals described herein are combined with liquid organic additives with the object of stabilizing the polypeptide crystals. Such a mixture can be characterized as an aqueous-organic mixture that comprises n % organic additive, where n is between 1 and 99 and m % aqueous solution, where m is 100-n. Examples of organic additives include phenolic compounds, such as m-cresol or phenol or a mixture thereof, and acetone, methyl alcohol, methyl isobutyl ketone, chloroform, 1-propanol, isopropanol, 2-propanol, acetonitrile, 1-butanol, 2-butanol, ethyl alcohol, cyclohexane, dioxane, ethyl acetate, dimethylformamide, dichloroethane, hexane, isooctane, methylene chloride, tert-butyl alcohol, toluene, carbon tetrachloride, or combinations thereof.

C. Liquid Formulations

Another embodiment provided herein is an aqueous formulation that allows for stable long-term storage of a pharmaceutical composition wherein a crystalline anti-PCSK9 antibody is the active ingredient used in the preparation of the pharmaceutical composition. This formulation is useful, in part, because it is more convenient to use for the patient, as this formulation does not require any extra steps such as rehydrating. As used herein, a "solution" or "liquid formulation" is meant to mean a liquid preparation that contains one or more chemical substances dissolved in a suitable solvent or mixture of mutually miscible solvents.

Reconstitution is the dissolution of polypeptide crystals or crystal formulations or compositions in an appropriate buffer or pharmaceutical formulation.

D. Components of Pharmaceutical Formulations

The present pharmaceutical composition is prepared by combining, in addition to a crystalline anti-PCSK9 antibody as described above, one or more of the following types of ingredients or excipients listed in the paragraphs below, many or all of which are available from commercial suppliers. It will be understood by one of ordinary skill in the art that the combining of the various components to be included in the composition can be done in any appropriate order, namely, the buffer can be added first, middle or last and the tonicity modifier can also be added first, middle or last. It is also to be understood by one of ordinary skill in the art that some of these chemicals can be incompatible in certain combinations, and accordingly, are easily substituted with different chemicals that have similar properties but are compatible in the relevant mixture. There is knowledge in the art regarding the suitability of various combinations of excipients and other ingredients or materials present in, for example, the containers used for storage of the pharmaceutical composition and/or the devices used for therapeutic administration (see, for example, Akers, 2002, J Pharm Sci 91: 2283-2300).

Non-limiting examples of additional agents that can be included in the formulations described herein include acidifying agents (including, but not limited to, acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid, and other suitable acids); active ingredients (including, but not limited to, additional active ingredients to reduce injection site discomfort, and non-steroidal anti-inflammatory drugs such as, for example, tromethamine, in an appropriate dosage); aerosol propellants (including, but not limited to, butane, dichlorodifluoromethane, dichlorotetrafluoroethane, isobutane, propane and trichloromonofluoromethane); alcohol denaturants (including, but not limited to, denatonium benzoate, methyl isobutyl ketone, sucrose octacetate); alkalizing agents (including, but not limited to, strong ammonia solution, ammonium carbonate, diethanolamine, diisopropanolamine, potassium hydroxide, sodium bicarbonate, sodium borate, sodium carbonate, sodium hydroxide, trolamine); anticaking agents (including, but not limited to, calcium silicate, magnesium silicate, colloidal silicon dioxide and talc); antifoaming agents (including, but not limited to, dimethicone and simethicone); chelating agents (also called sequestering agents) (including, but not limited to, edetate disodium, ethylenediaminetetraacetic acid and salts and edetic acid); coating agents (including, but not limited to, sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyethylene glycol, polyvinyl acetate phthalate, shellac, sucrose, titanium dioxide, carnauba wax, microcrystalline wax and zein); colors (including, but not limited to, caramel, erythrosine (FD&C Red No. 3); FD&C Red No. 40; FD&C Yellow No. 5; FD&C Yellow No. 6; FD&C Blue No. 1; red, yellow, black, blue or blends and ferric oxide); complexing agents (including, but not limited to, ethylenediaminetetraacetic acid (EDTA) and salts thereof, edetic acid, gentisic acid ethanolmaide and oxyquinoline sulfate); desiccants (including, but not limited to. calcium chloride, calcium sulfate and silicon dioxide); filtering aids (including, but not limited to, powdered cellulose and purified siliceous earth); flavors and perfumes (including, but not limited to, anethole, anise oil, benzaldehyde, cinnamon oil, cocoa, ethyl vanillin, menthol, methyl salicylate, monosodium glutamate, orange flower oil, orange oil, peppermint, peppermint oil, peppermint spirit, rose oil, stronger rose water, thymol, tolu balsam tincture, vanilla, vanilla tincture and vanillin); humectants (including, but not limited to, glycerin, hexylene glycol, propylene glycol and sorbitol); ointment bases (including, but not limited to, lanolin, anhydrous lanolin, hydrophilic ointment, white ointment, yellow ointment, polyethylene glycol ointment, petrolatum, hydrophilic petrolatum, white petrolatum, rose water ointment and squalane); plasticizers (including, but not limited to, castor oil, diacetylated monoglycerides, diethyl phthalate, glycerin, mono- and diacetylated monoglycerides, polyethylene glycol, propylene glycol, triacetin and triethyl citrate); polymer membranes (including, but not limited to, cellulose acetate); solvents (including, but not limited to, acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, polyethylene glycol, propylene carbonate, propylene glycol, sesame oil, water for injection, sterile water for injection, sterile water for irrigation and purified water); sorbents (including, but not limited to powdered cellulose, charcoal, purified siliceous earth; and carbon dioxide sorbents: barium hydroxide lime and soda lime); stiffening agents (including, but not limited to, hydrogenated castor oil, cetostearyl alcohol, cetyl alcohol, cetyl esters wax, hard fat, paraffin, polyethylene excipient, stearyl alcohol, emulsifying wax, white wax and yellow wax); suppository bases (including, but not limited to, cocoa butter, hard fat and polyethylene glycol); Suspending and/or viscosity-increasing agents (including, but not limited to, acacia, agar, alginic acid, aluminum monostearate, bentonite, purified bentonite, magma bentonite, carbomer 934p, carboxymethylcellulose calcium, carboxymethylcellulose sodium, carboxymethycellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth and xanthan gum); sweetening agents (including, but not limited to, aspartame, dextrates, dextrose, excipient dextrose, fructose, mannitol, saccharin, calcium saccharin, sodium saccharin, sorbitol, solution sorbitol, sucrose, compressible sugar, confectioner's sugar and syrup); tablet binders (including, but not limited to, acacia, alginic acid, sodium carboxymethylcellulose, microcrystalline cellulose, dextrin, ethylcellulose, gelatin, liquid glucose, guar gum, hydroxypropyl methylcellulose, methycellulose, polyethylene oxide, povidone, pregelatinized starch and syrup); tablet and/or capsule diluents (including, but not limited to, calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar and confectioner's sugar); tablet disintegrants (including, but not limited to, alginic acid, microcrystalline cellulose, croscarmellose sodium, corspovidone, polacrilin potassium, sodium starch glycolate, starch and pregelatinized starch); tablet and/or capsule lubricants (including, but not limited to, calcium stearate, glyceryl behenate, magnesium stearate, light mineral oil, polyethylene glycol, sodium stearyl fumarate, stearic acid, purified stearic acid, talc, hydrogenated vegetable oil and zinc stearate); ehicles (include, but are not limited to flavored and/or sweetened (aromatic elixir, compound benzaldehyde elixir, iso-alcoholic elixir, peppermint water, sorbitol solution, syrup, tolu balsam syrup); oleaginous (almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, seame oil, soybean oil, squalane); solid carriers such as sugar spheres; and sterile vehicles (bacteriostatic water for injection, bacteriostatic sodium chloride injection); and water-repelling agents (including, but not limited to, cyclomethicone, dimethicone and simethicone);

Aggregation inhibitors, reduce a polypeptide's tendency to associate in inappropriate or unwanted ternary or quaternary complexes, can also be included in the formulations described herein. Suitable aggregation inhibitors include the amino acids L-arginine and/or, L-cysteine, which can act to reduce aggregation of polypeptides containing an Fc domain over long periods, e.g., two years or more. The concentration of the aggregation inhibitor in the formulation can be between about 1 mM to 1M, or about 10 mM to about 200 mM, or about 10 mM to about 100 mM, or about 15 MM to about 75 mM, or about 150 mM to about 250 mM, or about 25 mM.

Antioxidants may also be included in the formulations described herein. Antioxidants contemplated for use in the preparation of the formulations include amino acids such as glycine and lysine, chelating agents such as EDTA and DTPA, and free-radical scavengers such as sorbitol and mannitol. Additional antioxidants include ascorbic acid, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, sodium thiosulfate, sufur dioxide, tocopherol, and tocopherols excipient. Also contemplated for use in inhibiting oxidation is nitrogen or carbon dioxide overlay. Nitrogen or carbon dioxide overlay can be introduced to the headspace of a vial or prefilled syringe during the filling process.

Buffering agents, which maintain the pH of the pharmaceutical formulation in a desired range, can also be included in the formulations described herein. When the pH of the pharmaceutical composition is set at or near physiological levels, comfort of the patient upon administration is maximized. In particular, in certain embodiments the pH of a pharmaceutical composition is within a pH range of about 4.0 to 8.4, or a pH range of about 5.0 to 8.0, or a pH range of about 5.8 to 7.4, or about 6.2 to 7.0. It is to be understood that the pH can be adjusted as necessary to maximize stability and solubility of the polypeptide in a particular formulation and as such, a pH outside of physiological ranges, yet tolerable to the patient, is within the scope of the invention. Various buffers suitable for use in the pharmaceutical composition of the invention include histidine, alkali salts (sodium or potassium phosphate or their hydrogen or dihydrogen salts), sodium citrate/citric acid, sodium acetate/acetic acid, potassium citrate, maleic acid, ammonium acetate, tris-(hydroxymethyl)-aminomethane (tris), various forms of acetate and diethanolamine, ammonium carbonate, ammonium phosphate, boric acid, lactic acid, phosphoric acid, potassium metaphosphate, potassium phosphate monobasic, sodium lactate solution, and any other pharmaceutically acceptable pH buffering agent known in the art. pH-adjusting agents such as hydrochloric acid, sodium hydroxide, or a salt thereof, may also be included in order to obtain the desired pH. One suitable buffer is sodium phosphate for maintaining pharmaceutical compositions at or near pH 6.2. In another example, acetate is a more efficient buffer at pH 5 than pH 6 so less acetate may be used in a solution at pH 5 than at pH 6. The concentration of the buffer in the formulation can be between about 1 mM to about 1M, or about 10 mM to about 300 mM.

Polymeric carriers can also be included in the formulations described herein. Polymeric carriers are polymers used for encapsulation of polypeptide crystals for delivery of polypeptide, including biological delivery. Such polymers include biocompatible and biodegradable polymers. The polymeric carrier may be a single polymer type or it may be composed of a mixture of polymer types. Polymers useful as the polymeric carrier, include for example, poly(acrylic acid), poly(cyanoacrylates), poly(amino acids), poly(anhydrides), poly(depsipeptide), poly(esters) such as poly(lactic acid) or PLA, poly(lactic-co-glycolic acid) or PLGA, poly (B-hydroxybutryate), poly(caprolactone) and poly(dioxanone); poly(ethylene glycol), poly((hydroxypropyl)methacrylamide, poly [(organo)phosphazene], poly(ortho esters), poly(vinyl alcohol), poly(vinylpyrrolidone), maleic anhydride-alkyl vinyl ether copolymers, pluronic polyols, albumin, natural and synthetic polypeptides, alginate, cellulose and cellulose derivatives, collagen, fibrin, gelatin, hyaluronic acid, oligosaccharides, glycaminoglycans, sulfated polysaccharides, or any conventional material that will encapsulate polypeptide crystals.

Preservatives, such as antimicrobial preservatives, are also contemplated for use in the formulations described herein. Suitable preservatives include, but are not limited to, benzalkonium chloride, benzalkonium chloride solution, benzelthonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, and thymol. The amount of preservative included will be in the range of 0% to 2% (w/v) or about 1% (w/v).

Solubilizing agents and stabilizers (also referred to as emulsifying agents, co-solutes, or co-solvents) that increase the solubility of the polypeptide and/or stabilize the polypeptide while in solution (or in dried or frozen forms) can also be added to a pharmaceutical composition. Examples of solubilizing and stabilizing agents include but are not limited to sugars/polyols such as: sucrose, lactose, glycerol, xylitol, sorbitol, mannitol, maltose, inositol, trehalose, glucose; polymers such as: serum albumin (bovine serum albumin (BSA), human SA (HSA), or recombinant HA), dextran, PVA, hydroxypropyl methylcellulose (HPMC), polyethyleneimine, gelatin, polyvinylpyrrolidone (PVP), hydroxyethylcellulose (HEC); non-aqueous solvents such as: polyhydric alcohols (e.g., PEG, ethylene glycol and glycerol), dimethysulfoxide (DMSO), and dimethylformamide (DMF); amino acids such as: proline, L-methionine, L-serine, sodium glutamic acid, alanine, glycine, lysine hydrochloride, sarcosine, and gamma-aminobutyric acid; surfactants such as: Tween-80, Tween-20, SDS, polysorbate, polyoxyethylene copolymer; and miscellaneous stabilizing excipients such as: potassium phosphate, sodium acetate, ammonium sulfate, magnesium sulfate, sodium sulfate, trimethylamine N-oxide, betaine, metal ions (e.g., zinc, copper, calcium, manganese, and magnesium), CHAPS, monolaurate, 2-O-beta-mannoglycerate; or any of the following: acacia, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 caster oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, polysorbate 100, Triton X-100, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, trolamine, emulsifying wax; wetting and/or solubilizing agents such as benzalkonium chloride, benzethonium chloride, cetylpyridinium chloride, docusate sodium, nonoxynol 9, nonoxynol 10, octoxynol 9, polyoxyl 50 stearate, tyloxapol; or any combination of the above. The concentration of solubilizers/stabilizers in the formulation can be between about 0.001 to 5 weight percent, or about 0.1 to 2 weight percent. In one embodiment, the stabilizer is selected from sorbitan mono-9-octadecenoate poly(oxy-1,2-ethanediyl) derivatives, including but not limited to, polysorbate 80 or polysorbate 20. The amount of polysorbate 20 or 80 to be used in this embodiment is in the range of 0.001% to 1.0% (w/v), such as 0.005% (w/v), in single use or in multi-dose formulations. In another embodiment, free L-methionine in the range of 0.05 mM to 50 mM is included in the formulation: the amount of free L-methionine is 0.05 mM to 5 mM for single use formulations, and 1 mM to 10 mM for multi-dose formulations.

Tonicity modifiers can also be included in the formulations described herein. Tonicity modifiers are understood to be molecules that contribute to the osmolality of a solution. The osmolality of a pharmaceutical composition is preferably regulated in order to maximize the active ingredient's stability and also to minimize discomfort to the patient upon administration. Serum is approximately 300+/−50 milliosmolals per kilogram. It is generally preferred that a pharmaceutical composition be isotonic with serum, i.e., having the same or similar osmolality, which is achieved by addition of a tonicity modifier, thus it is contemplated that the osmolality will be from about 180 to about 420 milliosmolals, however, it is to be understood that the osmolality can be either higher or lower as specific conditions require. Examples of tonicity modifiers suitable for modifying osmolality include, but are not limited to amino acids (e.g., arginine, cysteine, histidine and glycine), salts (e.g., sodium chloride, potassium chloride and sodium citrate) and/or saccharides (e.g., sucrose, glucose, dextrose, glycerin, and mannitol). The concentration of the tonicity modifier in the formulation can be between about 1 mM to 1M, or about 10 mM to about 200 mM. In one embodiment, the tonicity modifier is sodium chloride within a concentration range of 0 mM to 200 mM. In another embodiment, the tonicity modifier is sorbitol or trehalose and no sodium chloride is present.

In certain embodiments, the formulation comprises a compound selected from the following, or any combination thereof: salts of 1) amino acids such as glycine, arginine, aspartic acid, glutamic acid, lysine, asparagine, glutamine, proline; 2) carbohydrates, e.g. monosaccharides such as glucose, fructose, galactose, mannose, arabinose, xylose, ribose; 3) disaccharides, such as lactose, trehalose, maltose, sucrose; 4) polysaccharides, such as maltodextrins, dextrans, starch, glycogen; 5) alditols, such as mannitol, xylitol, lactitol, sorbitol; 6) glucuronic acid, galacturonic acid; 7) cyclodextrins, such as methyl cyclodextrin, hydroxypropyl-.beta.-cyclodextrin and alike; 8) inorganic salts, such as sodium chloride, potassium chloride, magnesium chloride, phosphates of sodium and potassium, boric acid ammonium carbonate and ammonium phosphate; 9) organic salts, such as acetates, citrate, ascorbate, lactate; 10) emulsifying or solubilizing agents like acacia, diethanolamine, glyceryl monostearate, lecithin, monoethanolamine, oleic acid, oleyl alcohol, poloxamer, polysorbates, sodium lauryl sulfate, stearic acid, sorbitan monolaurate, sorbitan monostearate, and other sorbitan derivatives, polyoxyl derivatives, wax, polyoxyethylene derivatives, sorbitan derivatives; 11) viscosity increasing reagents like, agar, alginic acid and its salts, guar gum, pectin, polyvinyl alcohol, polyethylene oxide, cellulose and its derivatives propylene carbonate, polyethylene glycol, hexylene glycol, tyloxapol; and 12) particular ingredients such as sucrose, trehalose, lactose, sorbitol, lactitol, inositol, salts of sodium and potssium such as acetate, phosphates, citrates, borate, glycine, arginine, polyethylene oxide, polyvinyl alcohol, polyethylene glycol, hexylene glycol, methoxy polyethylene glycol, gelatin, hydroxypropyl-β-cyclodextrin.

E. Sustained-Release Forms

In some embodiments, sustained-release forms (also called "controlled-release" forms) of crystalline anti-PCSK9 antibodies are used, including sustained-release forms of crystalline antibody 21B12; sustained- or controlled-release forms comprising crystalline antibody 21B12, and a substance for extending the physical release or biological availability of the crystalline antibody 21B12 over a desired period of time.

Sustained-release forms suitable for use in the disclosed methods include, but are not limited to, crystalline antibody 21B12 that is encapsulated in a sustained-release means such as a slowly-dissolving biocompatible polymer (for example, the polymeric carriers described herein, the alginate microparticles described in U.S. Pat. No. 6,036,978, or the polyethylene-vinyl acetate and poly(lactic-glucolic acid) compositions described in U.S. Pat. No. 6,083,534), admixed with such a polymer (including topically applied hydrogels), and or encased in a biocompatible semi-permeable implant. Further embodiments of the invention include additional sustained-release forms such as polymeric microparticles, wherein a mixture of the active ingredient and sustained-release means such as polymers (for example, PLGA) are dispersed within a continuous phase, and the resulting dispersion is directly lyophilized to remove water and organic solvents or additives and form said microparticles (U.S. Pat. No. 6,020,004, incorporated herein by reference in its entirety); injectable gel compositions comprising a biodegradable anionic polysaccharide such as an alginate ester, a polypeptide, and at least one bound polyvalent metal ion (U.S. Pat. No. 6,432,449, incorporated herein by reference in its entirety); injectable biodegradable polymeric matrices having reverse thermal gelation properties and optionally pH-responsive gelation/de-gelation properties (U.S. Pat. Nos. 6,541,033 and 6,451,346, incorporated herein by reference in their entireties); biocompatible polyol:oil suspensions, such as those wherein the suspension comprises polyol in the range of from about 15% to about 30% by weight (U.S. Pat. No. 6,245,740, incorporated by reference in its entirety). Such sustained release forms are suitable for continuous delivery of polypeptides through administration in the form of a depot, wherein the depot can be an implant, or can be in the form of injectable microspheres, nanospheres, or gels. The above listed U.S. patents (U.S. Pat. Nos. 6,036,978; 6,083,534; 6,020,004; 6,432,449; 6,541,033; 6,451,346, and 6,245,740) are incorporated in their entirety by reference herein. In addition, sustained- or controlled-release forms of crystalline polypeptides of the invention comprise types of sustained release means such as those described in Kim, C., 2000, "Controlled Release Dosage Form Design", Techonomic Publishing Co., Lancaster Pa., which include the following: natural polymers (gelatin, sodium alginic acid, xanthan gum, arabic gum, or chitosan), semi-synthetic polymers or cellulose derivatives (methylcellulose, ethylcellulose, hydroxyethylcellulose, hydroxypropylcellulose, hydroxyethylmethylcellulose, hydroxypropylmethylcellulose, sodium carboxymethylcellulose, cellulose acetate, cellulose acetate butyrate, cellulose acetate proprionate, cellulose acetatephthalate, or hydroxypropylmethylcellulose phthalate), and synthetic polymers (ion exchange resins (methacrylic acid, sulfonated polystyrene/divinylbenzene), polyacrylic acid (Carbopol), poly (MMA/MAA), poly(MMA/DEAMA), poly(MMA/EA), poly(vinylacetate phthalate), poly(vinyl alcohol), poly(vinyl pyrrolidone), poly(lactic acid), poly(glycolic acid), poly (lactic/glycolic acid), polyethylene glycol, polyethylene oxide, poly(dimethyl silicone), poly(hydroxyethyl methacrylate), poly(ethylene/vinyl acetate), poly(ethylene/vinyl alcohol), polybutadiene, poly(anhydride), poly(orthoester), and poly(glutamic acid)).

Further embodiments disclosed herein include antibody 21B12 crystals encapsulated in at least one polymeric carrier to form microspheres by virtue of encapsulation within the matrix of the polymeric carrier to preserve their native and biologically active tertiary structure, as described in U.S. Pat. No. 6,541,606, which is incorporated in its entirety by reference herein. Antibody 21B12 crystals or formulations thereof to be encapsulated are suspended in a polymeric carrier such as PLGA which is dissolved in an organic solvent or additive. Such encapsulated Antibody 21B12 crystals maintain the biological activity of antibody 21B12 for a longer period of time than antibody 21B12 in solution when stored under comparable conditions.

IV. Kits

As an additional aspect, described herein are kits which comprise one or more formulations described herein packaged in a manner which facilitates their use for administration to subjects. In one embodiment, such a kit includes a formulation described herein (e.g., a composition comprising any of the antibodies described therein), packaged in a container such as a sealed bottle, vessel, single-use or multi-use vial, prefilled syringe, or prefilled injection device, optionally with a label affixed to the container or included in the package that describes use of the compound or composition in practicing the method. In one aspect, the compound or composition is packaged in a unit dosage form. The kit may further include a device suitable for administering the composition according to a specific route of administration. Preferably, the kit contains a label that describes use of an antibody described herein or formulation described herein.

V. Dosages

The dosage regimen involved in a method for treating a condition described herein will be determined by the attending physician, considering various factors which modify the action of drugs, e.g. the age, condition, body weight, sex and diet of the patient, the severity of any infection, time of administration and other clinical factors. In various aspects, the dosage is in the range of 0.1-50 mg of a preparation of antibody per kilogram of body weight (calculating the mass of the protein alone, without chemical modification). In some embodiments, the dosage is about 0.5 mg/kg to 20 mg/kg, or about 0.5-10 mg/kg. In some embodiments, the dosage is about 120 mg to about 1200 mg, or about 280 to about 450 mg.

In various aspects, the dosage of an anti-PCSK9 antibody, e.g., antibody 21B12, can range from at least about 100 mg to at about 1400 mg; or about 120 mg to about 1200 mg; or about 120 mg to about 1000 mg; or about 120 mg to about 800 mg; or about 120 mg to about 700 mg; or about 120 mg to about 480 mg; or about 120 mg up to about 480 mg; or about 100 mg up to about 480 mg; or about 1200 mg to about 480 mg; or about 140 mg to about 480 mg; or about 145 mg to about 480 mg; or about 150 mg to about 480 mg; or about 160 mg to about 480 mg; or about 170 mg to about 480 mg; or about 180 mg to about 480 mg or about 190 mg to about 480 mg or about 200 mg to about 480 mg; or about 210 mg to about 480 mg; or about 220 mg to about 480 mg; or about 230 mg to about 480 mg; or about 240 mg to about 480 mg; or about 250 mg to about 480 mg; or about 260 mg to about 480 mg; or about 270 mg to about 480 mg; or about 280 mg to about 480 mg; or about 290 mg to about 480 mg; or about 300 mg to about 480 mg; or about 310 mg to about 480 mg; or about 320 mg to about 480 mg; or about 330 mg to about 480 mg; or about 340 mg to about 480 mg; or about 350 mg to about 480 mg; or about 360 mg to about 480 mg; or about 370 mg to about 480 mg; or about 380 mg to about 480 mg; or about 390 mg to about 480 mg; or about 400 mg to about 480 mg; or about 410 mg to about 480 mg; or about 420 mg to about 480 mg; or about 430 mg to about 480 mg; or about 440 mg to about 480 mg; or about 450 mg to about 480 mg;

or about 460 mg to about 480 mg; or about 470 mg to about 480 mg of an anti-PCSK9 antibody, e.g., antibody 21B12.

In certain embodiments, the frequency of dosing will take into account the pharmacokinetic parameters of an anti-PCSK antibody and/or any additional therapeutic agents in the formulation used. In certain embodiments, a clinician will administer the formulation until a dosage is reached that achieves the desired effect. In certain embodiments, the formulation can therefore be administered as a single dose, or as two, three, four or more doses (which may or may not contain the same amount of the desired molecule) over time, or as a continuous infusion via an implantation device or catheter. The formulation can also be delivered subcutaneously or intravenously with a standard needle and syringe. In addition, with respect to subcutaneous delivery, pen delivery devices, as well as autoinjector delivery devices, have applications in delivering a pharmaceutical formulation of the present invention. Further refinement of the appropriate dosage is routinely made by those of ordinary skill in the art and is within the ambit of tasks routinely performed by them. In certain embodiments, appropriate dosages can be ascertained through use of appropriate dose-response data. In some embodiments, the amount and frequency of administration can take into account the desired cholesterol level (serum and/or total) to be obtained and the subject's present cholesterol level, LDL level, and/or LDLR levels, all of which can be obtained by methods that are well known to those of skill in the art.

In some embodiments, a dosage of at least about 100 mg; or up to about 110 mg; or up to about 115 mg, or up to about 120 mg; or up to about 140 mg; or up to about 160 mg; or up to about 200 mg; or up to about 250 mg; or up to about 280 mg; or up to 300 mg; or up to 350 mg; or up to 400 mg; or up to 420 mg of an anti-PCSK9 antibody, e.g., antibody 21B12, is administered once every other week, (or every two weeks)(Q2W), to a patient in need thereof.

In certain other embodiments, a dosage of at least about 250 mg; or up to about 280 mg; or up to about 300 mg; or up to about 350 mg; or up to about 400 mg; or up to about 420 mg; or up to about 450 mg; or up to about 480 mg of a an anti-PCSK9 antibody, e.g., antibody 21B12, is administered once every four weeks, (or once a month), to a patient in need thereof.

The formulations are generally administered parenterally, e.g. intravenously, subcutaneously, intramuscularly, via aerosol (intrapulmonary or inhalational administration), or via depot for long-term release. In some embodiments, the formulation is administered intravenously by an initial bolus followed by a continuous infusion to maintain therapeutic circulating levels of drug product. In other embodiments, the formulation is administered as a one-time dose. Those of ordinary skill in the art will readily optimize effective dosages and administration regimens as determined by good medical practice and the clinical condition of the individual patient. The frequency of dosing will depend on the pharmacokinetic parameters of the agents and the route of administration. The optimal pharmaceutical formulation will be determined by one skilled in the art depending upon the route of administration and desired dosage. See for example, Remington's Pharmaceutical Sciences, 18th Ed. (1990, Mack Publishing Co., Easton, Pa. 18042) pages 1435-1712, the disclosure of which is hereby incorporated by reference. Such formulations may influence the physical state, stability, rate of in vivo release, and rate of in vivo clearance of the administered agents. Depending on the route of administration, a suitable dose may be calculated according to body weight, body surface area or organ size. Further refinement of the calculations necessary to determine the appropriate dosage for treatment involving each of the above mentioned formulations is routinely made by those of ordinary skill in the art without undue experimentation, especially in light of the dosage information and assays disclosed herein, as well as the pharmacokinetic data observed in the human clinical trials discussed above. Appropriate dosages may be ascertained through use of established assays for determining blood level dosages in conjunction with appropriate dose-response data. The final dosage regimen will be determined by the attending physician, considering various factors which modify the action of drugs, e.g. the drug's specific activity, the severity of the damage and the responsiveness of the patient, the age, condition, body weight, sex and diet of the patient, the severity of any infection, time of administration and other clinical factors. As studies are conducted, further information will emerge regarding the appropriate dosage levels and duration of treatment for various diseases and conditions.

VI. Therapeutic Uses of the Formulation

As will be appreciated by one of skill in the art, disorders that relate to, involve, or can be influenced by varied cholesterol, LDL, LDLR, PCSK9, VLDL-C, apoprotein B ("ApoB"), lipoprotein A ("Lp(a)"), triglycerides, HDL-C, non-HDL-C, and total cholesterol levels can be addressed by the pharmaceutical formulations of the present invention. In one aspect, the anti-PCS9 antibody formulations can be used in methods to treat and/or prevent and/or reduce the risk of disorders that relate to elevated serum cholesterol levels or in which elevated serum cholesterol levels are relevant. In one aspect, the anti-PCS9 antibody formulations can be used in methods to treat and/or prevent and/or reduce the risk of disorders that relate to elevated PCSK9 values or in which elevated PCSK9 values are relevant. In one aspect, the anti-PCS9 antibody formulations can be used in methods to treat and/or prevent and/or reduce the risk of disorders that relate to elevated total cholesterol levels or in which elevated total cholesterol levels are relevant. In one aspect, the anti-PCS9 antibody formulations can be used in methods to treat and/or prevent and/or reduce the risk of disorders that relate to elevated non-HDL cholesterol levels or in which elevated non-HDL cholesterol levels are relevant. In one aspect, the anti-PCS9 antibody formulations can be used in methods to treat and/or prevent and/or reduce the risk of disorders that relate to elevated ApoB levels or in which elevated ApoB levels are relevant. In one aspect, the anti-PCS9 antibody formulations can be used in methods to treat and/or prevent and/or reduce the risk of disorders that relate to elevated Lp(a) levels or in which elevated Lp(a) levels are relevant. In one aspect, the anti-PCS9 antibody formulations can be used in methods to treat and/or prevent and/or reduce the risk of disorders that relate to elevated triglyceride levels or in which elevated triglyceride levels are relevant. In one aspect, the anti-PCS9 antibody formulations can be used in methods to treat and/or prevent and/or reduce the risk of disorders that relate to elevated VLDL-C levels or in which elevated VLDL-C levels are relevant.

As will be appreciated by one of skill in the art, the anti-PCS9 antibody formulations of the present invention can be therapeutically useful in treating and/or preventing cholesterol related disorders. Exemplary, non-limiting diseases and disorders that can be treated or prevented by the administration of the pharmaceutical formulations of the present invention include familial hypercholesterolemia, non-familial hypercholesterolemia, hyperlipidemia, heart disease, metabolic syndrome, diabetes, coronary heart disease, stroke, cardiovascular diseases, Alzheimer's disease and generally dyslipidemias, which can be manifested, for example, by an elevated total serum cholesterol, elevated LDL, elevated triglycerides, elevated VLDL, and/or low HDL. Some non-limiting examples of primary and secondary dyslipidemias that can be treated using the formulations described herein, either alone, or in combination with one or more other agents include the metabolic syndrome, diabetes mellitus, familial combined hyperlipidemia, familial hypertriglyceridemia, familial hypercholesterolemias, including heterozygous hypercholesterolemia, homozygous hypercholesterolemia, familial defective apolipoprotein B-100; polygenic hypercholesterolemia; remnant removal disease, hepatic lipase deficiency; dyslipidemia secondary to any of the following: dietary indiscretion, hypothyroidism, drugs including estrogen and progestin therapy, beta-blockers, and thiazide diuretics; nephrotic syndrome, chronic renal failure, Cushing's syndrome, primary biliary cirrhosis, glycogen storage diseases, hepatoma, cholestasis, acromegaly, insulinoma, isolated growth hormone deficiency, and alcohol-induced hypertriglyceridemia. The formulations of the present invention can also be useful in preventing or treating atherosclerotic diseases, such as, for example, cardiovascular death, non-cardiovascular or all-cause death, coronary heart disease, coronary artery disease, peripheral arterial disease, stroke (ischaemic and hemorrhagic), angina pectoris, or cerebrovascular disease and acute coronary syndrome, myocardial infarction and unstable angina. In some embodiments, the formulations are useful in reducing the risk of: fatal and nonfatal heart attacks, fatal and non-fatal strokes, certain types of heart surgery, hospitalization for heart failure, chest pain in patients with heart disease, and/or cardiovascular events because of established heart disease such as prior heart attack, prior heart surgery, and/or chest pain with evidence of clogged arteries and/or transplant-related vascular disease. In some embodiments, the formulations are useful in preventing or reducing the cardiovascular risk due to elevated CRP or hsCRP. In some embodiments, the formulations and methods can be used to reduce the risk of recurrent cardiovascular events.

As will be appreciated by one of skill in the art, diseases or disorders that are generally addressable (either treatable or preventable) through the use of statins can also benefit from the application of formulations of this invention. In addition, as will be appreciated by one of skill in the art, the use of formulations of this invention can be especially useful in the treatment of diabetes.

In some embodiments, the formulations of the present invention are administered to those who have diabetes mellitus, abdominal aortic aneurysm, atherosclerosis and/or peripheral vascular disease in order to decrease their serum cholesterol levels to a safer range. In some embodiments, the formulations of this invention are administered to patients at risk of developing any of the herein described disorders. In some embodiments, the formulations of this invention are administered to subjects that smoke, or used to smoke (i.e., former smokers), have hypertension or a familial history of early heart attacks.

The formulation need not cure the subject of the disorder. The formulation may be used therapeutically to ameliorate, in whole or in part, a cholesterol-related disorder or symptom thereof, or to protect, in whole or in part, against further progression of a cholesterol-related disorder or symptom thereof. Indeed, the materials and methods of the invention are particularly useful for lowering serum LDL cholesterol and maintaining the reduction in serum LDL cholesterol over a period of time.

One or more administrations of a formulation described herein may be carried out over a therapeutic period of, for example, about 2 weeks to about 12 months (e.g., about 1 month, about 2 months, about 3 months, about 4 months, about 5 months, about 6 months, about 7 months, about 8 months, about 9 months, about 10 months, or about 11 months). In some embodiments, a subject is administered one or more doses of the formulation to lower serum LDL cholesterol. The term "maintain reduction of serum LDL cholesterol" as used herein means the reduction of serum LDL cholesterol resulting the initial dose of the formulation does not fall more than about 1% to about 5% over the course of about 2 weeks, about 1 month, about 2 months, about 3 months, about 6 months, about 9 months about 1 year, about 18 months, about 2 years, or over the course of the patient's life).

In addition, it may be advantageous to administer multiple doses of the formulation or space out the administration of doses, depending on the therapeutic regimen selected for a particular subject. The formulation can be administered periodically over a time period of one year or less (e.g., 9 months or less, 6 months or less, or 3 months or less). In this regard, the formulation can be administered to the human once every about 7 days, or 2 weeks, or 3 weeks, or 1 month, or 5 weeks, or 6 weeks, or 7 weeks, or 2 months, or 9 weeks, or 10 weeks, or 11 weeks, or 3 months, or 13 weeks, or 14 weeks, or 15 weeks, or 4 months, or 17 weeks, or 18 weeks, or 19 weeks, or 5 months, or 21 weeks, or 22 weeks, or 23 weeks, or 6 months, or 12 months.

VII. Combination Therapy

Treatment of a pathology by combining two or more agents that target the same pathogen or biochemical pathway sometimes results in greater efficacy and diminished side effects relative to the use of the therapeutically relevant dose of each agent alone. In some cases, the efficacy of the drug combination is additive (the efficacy of the combination is approximately equal to the sum of the effects of each drug alone), but in other cases the effect can be synergistic (the efficacy of the combination is greater than the sum of the effects of each drug given alone). As used herein, the term "combination therapy" means the two compounds can be delivered in a simultaneous manner, e.g. concurrently, or wherein one of the compounds is administered first, followed by the second agent, e.g., sequentially. The desired result can be either a subjective relief of one or more symptoms or an objectively identifiable improvement in the recipient of the dosage.

In some embodiments, the formulation is administered prior to, concurrent with, or subsequent to, a standard of care therapeutic for the treatment of decreased bone mineral density. As used herein, the term "standard of care" refers to a treatment that is generally accepted by clinicians for a certain type of patient diagnosed with a type of illness. In some embodiments, the standard of care therapeutic is at least one other cholesterol-lowering (serum and/or total body cholesterol) agent. Exemplary agents include, but are not limited to, statins (atorvastatin, cerivastatin, fluvastatin, lovastatin, mevastatin, pitavastatin, pravastatin, rosuvastatin, simvastatin), Nicotinic acid (Niacin) (NIACOR, NIASPAN (slow release niacin), SLO-NIACIN (slow release niacin), CORDAPTIVE (laropiprant)), Fibric acid (LOPID (Gemfibrozil), TRICOR (fenofibrate), Bile acid sequestrants (QUESTRAN (cholestyramine), colesevelam (WELCHOL), COLESTID (colestipol)), Cholesterol absorption inhibitors (ZETIA (ezetimibe)), Combining nicotinic acid with statin (ADVICOR (LOVASTATIN and NIASPAN), Combining a statin with an absorption inhibitor (VYTORIN (ZOCOR and ZETIA) and/or lipid modifying agents. In some embodiments, the formulation is combined with PPAR gamma agonists, PPAR alpha/gamma agonists, squalene synthase inhibitors, CETP inhibitors, anti-hypertensives, anti-diabetic agents (such as sulphonyl ureas, insulin, GLP-1 analogs, DDPIV inhibitors, e.g., metaformin), ApoB modulators, such as mipomersan, MTP inhibitors and/or arteriosclerosis obliterans treatments. In some embodiments, the formulation is combined with an agent that increases the level of LDLR protein in a subject, such as statins, certain cytokines like oncostatin M, estrogen, and/or certain herbal ingredients such as berberine. In some embodiments, the formulation is combined with an agent that increases serum cholesterol levels in a subject (such as certain anti-psychotic agents, certain HIV protease inhibitors, dietary factors such as high fructose, sucrose, cholesterol or certain fatty acids and certain nuclear receptor agonists and antagonists for RXR, RAR, LXR, FXR). In some embodiments, the formulation is combined with an agent that increases the level of PCSK9 in a subject, such as statins and/or insulin. The combination of the two can allow for the undesirable side-effects of other agents to be mitigated by the formulation.

In some embodiments, the formulation is administered to a subject when treatment of a standard of care therapeutic described herein is contraindicated.

EXAMPLES

Example 1—Crystallization of Antibody, 21B12

Antibody 21B12 in 10 mM sodium acetate, 9% sucrose, pH5.2 consisting of two mature heavy chains (SEQ ID NO:19) and two mature light chains (SEQ ID NO:17) recombinantly produced by DNA encoding each of these chains was crystallized under a variety of conditions.

Crystallization of antibody 21B12 was achieved using 18 different crystallization screens (Hampton Research, Aliso Viejo, Calif. and Rigaku Reagents, Bainbridge Island, Wash.), which employ a method for crystallization of macromolecules known as 'hanging drop' vapor diffusion. A drop composed of a mixture of the protein and the crystallization reagent (the "crystallization buffer" or the "mother liquor" or "crystal growth solution" or the "reservoir solution") is deposited on the underside of a sialanized coverslip, and then the drop on the coverslip is sealed with grease and placed over typically a 24 well VDX tray with sealant (Hampton Research, Aliso Viejo, Calif. (HR3-170)) causing a vapor equilibrium with a liquid reservoir of reagent. To achieve equilibrium, water vapor exchanges between the drop and a 1ml reservoir solution in the well of the tray. As water leaves the drop, the protein undergoes an increase in relative concentration which may eventually lead to supersaturation. It is the supersaturation of protein that is required for crystallization to take place. Typically the drop contains a lower concentration of reagent than the reservoir, and typically, the drop contained half the concentration of reagent in the reservoir, because equal volumes of sample and reagent were mixed to form the drop (this was the case for all crystallization conditions except the LISS (Low Ionic Strength Screen) where the protein was 4 ul, buffer was 2 ul and the precipitant was 5 ul with a total drop volume of 11 ul).

In these experiments, the initial protein concentration in the drop was 1 mg/ml to about 140 mg/ml.

Some of the crystallization screens were set up in 24-well VDX trays with sealant. Each position in the VDX tray contained 1 mL of reagent reservoir, with the reagent reservoir in each well differing in composition from that in the other wells, to establish an array of differing crystallization buffer conditions. 1-10 μL of protein was added to 1-10 μl of reservoir solution to form the drops. Trays were incubated at ambient room temperature.

Some hanging drop vapor diffusion crystal trays were also set up using the Mosquito Crystal (TTP LabTech, Melbourn Science Park, Melbourn, Hertfordshire SG8 6EE, United Kingdom) using clear flat bottom polystyrene 96 well microplates (Catalog #9017—Corning Incorporated, One Riverfront Plaza, Corning, N.Y. 14831, USA) with 100 ul as the well solution, 1:1 ratio of protein to well solution in the drop. The final drop volume was 600 nl. 300 nl of protein was placed on the center of each 96 well plate seal (TTP Labtech Catalog #4150-05100) (which was placed on the 96 well substrate/holder) followed by 300 nl of well solution. The 96 well substrate was inverted and sealed on top of the 96 well plate and were stored at ambient room temperature.

Crystal trays were scanned everyday for a week and then once a week using Carl Zeiss Axiocam MRc Microscope equipped with software Axiovison 4.0, www.zeiss.com. Crystal hits were recorded and characterized using an in house crystal scoring system and morphology description (see Table 1.1). Crystal hits were tested for protein crystals via the touch test, Izit crystal dye (Hampton Research HR4-710) test and by setting up control trays for water and buffer for crystallization screens.

TABLE 1.1

Crystal Scoring System and Morphology Description.

| Score | Description | Score | Description | Morphology | Description | Morphology | Description |
|---|---|---|---|---|---|---|---|
| 0 | no precipitation | 49 | needles | UFO | UFO | TM | trail mix |
| 1 | light precipitation | 50 | plates | FT | footballs | C | clusters |
| 2 | med precipitation | 51 | rods | LV | leaves | T | tiny |
| 3 | heavy precipitation | 52 | blocks | WH | wheat | FW | few |
| 5 | bi-refringence precipitation | | | S | singlet | ST | straws |
| 10 | oil; biphasic | | | FE | feathers | CHR | *chrysanthemum* |
| 15 | crystal balls | | | SK | skin | DR | dried |

Crystallization Screens:

Antibody 21B12 was screened in a total of approximately 2000 conditions using 18 different crystallization screens which resulted in 16 crystal hits (since Wizard IV #13 and Wizard JCSG are the same conditions). Unless specifically noted otherwise below, the crystallization screens were set up in 24-well VDX trays with sealant.

Antibody 21B12 was screened in the LISS (Low Ionic Strength Screen) (Hampton Research HR3-170). The Low Ionic Strength Screen (LISS) is a three part crystallization screen with 18 buffers in a pH range of 2-12, 6 different percentages of precipitant PEG3350 and 24% PEG3350 as dehydrant especially designed for antibody and antibody fragments screening. A total of 108 conditions were screened and antibody 21B12 crystallized in 0.05M Citric acid pH5.5, 12% PEG3350 on day 1 at 10 mg/ml. The crystal morphology resembled leaves.

Antibody 21B12 was screened in Index Screen (Hampton Research HR2-144). The Index screen combines strategies of the Grid screen, Sparse Matrix and Incomplete Factorial with classical, contemporary and new crystallization reagent systems. Index Screen is formulated in zones: classic salts versus pH, neutralized organic acids, high salt and low polymer, high polymer and low salt, low ionic strength versus pH, PEG and salt versus pH, PEG and salt. A total of 96 conditions were screened and antibody 21B12 crystallized in Index #31 (0.8M Potassium sodium tartrate tetrahydrate, 0.1M Tris pH8.5, 0.5% w/v Polyethylene glycol monomethyl ether 5000) on day 1 with crystal morphology of hexagonal blocks.

Antibody 21B12 was screened in Wizard I (Emerald Bio EB-W1-T), Wizard II (Emerald Bio EB-W2-T), Wizard III (Emerald Bio EB-W3-T) and Wizard IV (Emerald Bio EB-W4-T). The primary screen variables are buffers, salts covering a broad range of crystallization space at pH4.5 to pH 10.5. A total of 192 conditions were screened and antibody 21B12 crystallized in Wizard I #13 (1.26M (NH4)2SO4, 0.1M cacodylate pH6.5) and Wizard 1#32 (10% (w/v) PEG 3000, Na/K Phosphate pH6.2) on day 3 and on day 2, respectively, with crystal morphology of hexagonal blocks. Antibody 21B12 crystallized in Wizard II #15 (1.26 M (NH4)2SO4, HEPES pH7.5), and Wizard II #45 (1.26M (NH4)2SO4, MES pH6.0), on day 3 and day 3, respectively, with crystal morphology of hexagonal blocks. Antibody 21B12 crystallized in Wizard IV #13 (800 mM Succinic Acid pH7.0), and Wizard IV #31 (20% (w/v) Polyacrylic acid 5100, 0.1M HEPES pH7.0, 20 mM Magnesium chloride) both on day 1 with crystal morphology of rods.

Antibody 21B12 was screened in Crystal Screen HT (Hampton Research HR2-130). The primary screen variables are salt, pH and precipitants (salts, polymers, volatile organics and non-volatile organics). A total of 96 conditions were screened using Mosquito Crystal and antibody 21B12 crystallized in Crystal screen HT #48 (0.1M Tris HCl pH 8.5, 2.0M Ammonium phosphate monobasic) on day 4 with crystal morphology of hexagonal blocks.

Antibody 21B12 was screened in PEG/ION HT (Hampton Research HR2-139. The primary screen variables are PEG, ion type, ionic strength and pH. The screen combines high purity Polyethylene glycol 3350, 48 different high purity salts, comprising both anions (sulfate, nitrate, tartrate, acetate, chloride, iodide, thiocyanate, formate, citrate, phosphate and fluoride) and cations (sodium, potassium, ammonium, lithium, magnesium and calcium) in a relatively concentration of 0.2M which also works as a pH screen from pH 4-9. A total of 96 conditions were screened using Mosquito crystal and antibody 21B12 crystallized Peg/Ion HT #73 (0.1M Sodium acetate trihydrate pH7.0, 12% (w/v) Polyethylene glycol 3350) on day 4 with crystal morphology as rods.

Antibody 21B12 was screened in Wizard Precipitant Synergy I (Emerald Bio EB-PS-B) and Wizard Precipitant Synergy II (Emerald Bio EB-PS-B). The Wizard Precipitant screen consists of selected combinations of at least two different precipitating reagents, allowing the assessment of crystallization factors in five different dimensions: 8 different salts, 4 different organic solvents, 4 different polyethylene glycols, 9 different additives, pH range from 4.5-8.5. Each of the 64 base formulations contains precipitants at high concentration, close to their maximum solubility, in order to reach or exceed the protein's precipitation point. Corresponding formulations with precipitant concentrations at 67%, and 33%, but same buffer concentration ensures finer grid coverage of crystallization space and systematic crystallization. A total of 192 conditions were screened using Mosquito crystal and antibody 21B12 crystallized in Wizard Precipitant Synergy I #54 (0.66M Lithium sulfate, 0.66% (v/v) PEG400, 0.1M Tris HCl pH8.5) on day 0 with a crystal morphology of hexagonal blocks; Wizard Precipitant Synergy I #2 (1.34M Ammonium sulfate, 1.34% (v/v) PEG400, 0.1M Sodium acetate/Acetic acid pH5.5) on day 3 with crystal morphology of hexagonal blocks; and Wizard Precipitant Synergy I #42 (1.65% (v/v) PEG 400, 0.66M Ammonium citrate/citric acid pH7.5) on day 3 with a crystal morphology of hexagonal blocks. Antibody 21B12 crystallized in Wizard Precipitant Synergy II #83 (0.34% (w/v) PEG 4000, 0.67M Potassium phosphate dibasic/Sodium phosphate monobasic pH7.5) and Wizard Precipitant Synergy II #88 (2% (w/v) PEG 8000, 0.5M Ammonium citrate/Ammonium hydroxide pH8.5), both on day 3 with crystal morphology of rods.

Antibody 21B12 was screened in Wizard JCSG (Emerald Bio EB-JCSG-B). The primary screen variables are: buffers, salts, precipitants (include volatile reagents, high molecular weight polymers and salts) and pH. A total of 96 conditions were screened using Mosquito crystal and antibody 21B12 crystallized in Wizard JCSG #67 (800 mM Succinic acid pH7.0) and Wizard JCSG #71 (1000 mM Succinic acid pH 7.0, 100 mM HEPES free acid/Sodium hydroxide pH7.0, 1% (w/v) PEG 2000 MME) both on day 3 with crystal morphology of hexagonal blocks. Wizard JCSG #67 is the same as condition Wizard IV #13 with 800 mM Succinic acid at pH7.0.

Antibody 21B12 was screened in Wizard pH Buffer Screen (Emerald Bio EB-PH-B) a screen designed to optimize crystal hit condition to simultaneously explore the effects of pH and buffer composition of crystal growth. The Wizard pH buffer screen consists of 12 buffer systems at 8 pH points incrementally varied by 0.4 pH units. Antibody 21B12 was screened in the Wizard pH buffer screen along with 12% PEG3350 and 16% PEG3350. No crystal hits were observed with the 12% PEG3350. Two crystal hits were observed on day 2 with 16% PEG3350. Antibody 21B12 crystallized in Wizard pH Buffer Screen with 16% PEG3350 in 1M phosphate (di)/Sodium (mono) phosphate, 8.2 and 1M phosphate (di)/Sodium (mono) phosphate, 8.6.

Various morphologies of antibody 21B12 crystals can be grown under scale-up conditions whereby the antibody in a liquid formulation is added to a volume of known crystallization reagent and stored in a sealed container. Antibody 21B12 crystals can be grown under these conditions in less than 24 hours.

The foregoing Example demonstrates that antibody 21B12 was crystallizable under a variety of crystallization conditions, but crystals did not form under every condition tested. Approximately 2000 crystallization conditions were tested in a number of different commercially-available (i.e., Hampton Research, Rigaku Reagents) and proprietary screens.

Example 2—Antibody 21B12 Crystal Hits Optimization and Expansion

Certain conditions that proved successful in generating Antibody 21B12 crystals as described in Example 1 were optimized and expanded as follows:

Low Ionic Strength Screen #7 (0.05M Citric Acid pH 5.5, 12% PEG3350) at 4 mg/ml:

Antibody, 21B12, was screened in LISS #7 (0.05M Citric acid pH 5.5, 4% PEG3350) at 72 mg/ml. Antibody, 21B12, crystals were observed at day1 at pH5.5 and day4 at pH5.0. The crystal morphology was blocks. Antibody, 21B12, was screened in LISS #7 (0.05M Citric acid pH5.5, 8% PEG3350) at 72 mg/ml. Antibody, 21B12, crystals were observed at day1 at pH5.5. The crystal morphology was blocks. Antibody, 21B12, was screened in LISS #7 (0.05M Citric acid pH5.5, 12% PEG3350) at 72 mg/ml. Antibody, 21B12, crystals were observed at day4 at pH5.5. The crystal morphology was rods. Antibody, 21B12, was screened in LISS #7 (0.05M Citric acid pH 5.5, 16% PEG3350) at 72 mg/ml. No crystal hits were observed.

Antibody, 21B12, was also screened using the Citric Acid Stock Options (Hampton Research Catalog # HR2-104) pH2.2-6.5 in 0.1 pH unit increments which accounted for 44 conditions. Antibody, 21B12, crystals were observed from pH4.0 to 5.4, pH5.6, pH5.7, pH5.9, pH6.3 and pH6.4 on day1. On Day2 crystals were observed for pH4.0 to pH6.5. At day3, Antibody, 21B12, crystals were observed at pH3.8 while on day4, Antibody, 21B12, crystals were observed at pH3.9. Overall, Antibody, 21B12, in the Citric Acid Stock Options Kit crystallized from pH 3.8 to pH 6.5 in 0.1 pH unit increments.

Index Screen #31 (0.8 M Potassium Sodium Tartrate Tetrahydrate, 0.1M Tris pH 8.5, 0.5% (W/V) Peg Mme 5000):

Index Screen #31 was expanded by screening the potassium sodium tartrate tetrahydrate concentration from 0.2M to 1.2M in 0.2M increments. Antibody, 21B12, crystals were observed on day1 at 0.8M potassium sodium tartrate tetrahydrate with crystal morphology of hexagonal blocks.

Index Screen #31 was expanded by screening the PEG MME 5000 concentration from 0% to 1.5% in 0.5% increments. Antibody, 21B12, crystals were observed on day1 at all PEG MME 5000 concentrations with crystal morphology of hexagonal blocks.

Index Screen #31 was expanded using Tris stock options buffer kit from a pH range of 7.0 to 9.0 in 0.1 pH unit increments. Antibody, 21B12, crystals were observed on day1 at the following pH with crystal morphology of hexagonal blocks: pH 8.0 to pH 8.5 in 0.1 pH unit increments.

Index Screen #31 was expanded by screening various molecular weight PEGs (550 to 10,000). Antibody, 21B12, crystals were observed on day 1 in every PEG attempted, regardless of molecular weight with crystal morphology of blocks.

Index Screen #31 was expanded by screening PEG5000 from 1% to 6%. Antibody, 21B12, crystals were observed at PEG5000 concentrations from 1% to 5% on day 1 or day 2. Crystal morphology was blocks.

Index Screen #31 was expanded by screening Tris pH8.1 to pH 8.5 and tartrate from 0.6M, 0.65M, 0.7M, 0.75M, 0.8M and 0.9M. Antibody, 21B12, crystals were observed at pH 8.1 to 8.4 and tartrate concentrations from 0.6M to 0.9M. Crystal morphology was primarily blocks; crystals grown at pH 8.1 and lower Tartrate concentrations were a mixture of rod and block morphologies.

Index Screen #31 was expanded by screening various protein concentrations: 3 mg/ml, 6 mg/ml, 9 mg/ml, 12 mg/ml, 15 mg/ml, 18 mg/ml, 21 mg/ml, 24 mg/ml, 27 mg/ml, 30 mg/ml, 33 mg/ml, 36 mg/ml, 39 mg/ml, 42 mg/ml, 45 mg/ml, 48 mg/ml, 51 mg/ml, 54 mg/ml, 57 mg/ml, 60 mg/ml, 63 mg/ml, 66 mg/ml, 69 mg/ml and 72 mg/ml. Antibody, 21B12, crystals were observed as small crystals at the following concentrations: 12 mg/ml, 15 mg/ml, 60 mg/ml, 63 mg/ml, 66 mg/ml, 69 mg/ml and 72 mg/ml. Antibody, 21B12, crystals were observed as hexagonal blocks for the rest of the concentrations. Ostwald ripening (dissolution of smaller crystals to form large crystals) was also observed for the following concentrations: 18 mg/ml, 30 mg/ml and 33 mg/ml. Ostwald ripening is observed when smaller crystals dissolve to form a large crystal.

Wizard I #13 (1.26M Ammonium Sulfate, 0.1M Cacodylate pH6.5):

Wizard I #13 was expanded by screening Cacodylate pH range 5.1-7.4 in 0.1 pH unit increments. Antibody, 21B12, crystals were observed at pH6.7, pH6.9, pH7.0, pH 7.2-pH 7.4 on day1. Antibody, 21B12, crystals were observed on day4 at pH5.1. At day7 Antibody, 21B12 crystals were observed at pH5.6 and pH 6.0 with hexagonal blocks as crystal morphology.

Wizard I #13 was expanded by screening the salt concentration range of Ammonium sulfate. A broad salt concentration range was screened, and Antibody, 21B12, crystals were observed at 1.25M and 1.5M final Ammonium sulfate concentration with crystal morphology resembling leaves.

Wizard I #32 (10% (w/v) PEG3000, 0.1M Sodium/Potassium Phosphate pH 6.2):

Antibody, 21B12, crystal hit in Wizard I #32 was further expanded by screening using the Stock Option Phosphate kit (HR2-251) from pH 5.0-pH 8.2 in 0.2 pH unit increments. Antibody, 21B12, crystallized at day2 at pH5.6 with crystal morphology resembling leaves. Antibody, 21B12, crystal hit in Wizard I #32 was further expanded by screening the concentration of the precipitant PEG3000 from 5% to 30% and the salt concentration of Na/K Phosphate from 0.05M to 0.2M at pH 6.2 which did not yield in any crystal hits.

Wizard II #15 (1.26M Ammonium Sulfate, 0.1M HEPES pH7.5):

Wizard II #15 was expanded by screening using the Stock Option HEPES kit (HR2-102) from pH 6.8-pH 8.2 in 0.1 pH unit increments. Antibody, 21B12, crystals were observed at day1 at pH 7.5 and pH8.1. At day 2, Antibody, 21B12, crystals were observed at all other pH units from 6.9 to pH 7.4, pH7.6 to pH 8.2 with crystal morphology of hexagonal blocks.

Wizard II #15 was expanded by screening the concentration of the salt ammonium sulfate from 0.5M to 1.75M in 0.25M increments. Antibody, 21B12, crystallized at day1 at 1.25M and 1.5M salt concentration with crystal morphology of hexagonal blocks.

Wizard II #45 (1.26M Ammonium Sulfate, 0.1M MES pH6.0):

Wizard II #45 was expanded by screening using the Stock Option MES kit (HR2-243) from pH 5.2-pH 7.1 in 0.1 pH unit increments. Antibody, 21B12, crystals were observed at day1 at pH6.3. Antibody, 21B12, crystals were observed at day4 at the following pH units: pH5.3, pH5.9 to pH 6.2, pH6.4 to pH7.1. Antibody, 21B12, crystals were observed at day6 at the following pH units: pH5.2 to pH5.8. Antibody, 21B12, crystals were observed in the HEPES stock options kit at all pH units from pH5.2 to pH 7.1 in 0.1 pH unit increments with crystal morphology of hexagonal blocks.

Wizard II #45 was expanded using the Stock Open Sodium Acetate kit (HR2-233) from pH 3.6-5.6 in 0.1 pH unit increments. Antibody, 21B12, crystals were observed at day1 at pH 4.6-5.6 with crystal morphology of hexagonal blocks Ammonium sulfate concentrations were also expanded from 1.0M to 3.4M using the same pH screen with hexagonal blocks observed after day1 in 1.0-1.2M ammonium sulfate.

Wizard II #45 was expanded by screening the salt ammonium sulfate concentration range from 0.1M to 1.1M with 0.2M increments. No crystals were observed for the salt concentration screening.

Wizard IV #13 and JCSG #67 (800 mM Succinic Acid pH7.0):

Wizard IV #13 and JCSG #67 was expanded by screening using the Stock Option Succinic acid kit (HR2-249) from pH 4.3-pH 6.6 in 0.1 pH unit increments. Antibody, 21B12, crystals were observed at day1 at pH6.3 to pH 6.6. Antibody, 21B12, crystals were observed on day7 at pH6.2. Antibody, 21B12, crystals were observed in the Succinic acid stock options kits from pH units 6.2 to pH 6.6 in 0.1 pH unit increments with crystal morphology of hexagonal blocks.

Wizard IV #13 was screened by exploring the Succinic acid concentration range from 0.1M to 1.1M with 0.2M increments. Antibody, 21B12, crystals were observed at day3 at 0.7M Succinic acid with crystal morphology of hexagonal blocks.

Wizard IV #31(20% (w/v) Polyacrylic Acid 5100, HEPES pH7.0, 20 mM Magnesium Chloride):

Wizard IV #31 was expanded by screening using the Stock Options kit Na-HEPES (HR2-231) from pH 6.8 to pH 8.2 in 0.1 pH unit increment. Antibody, 21B12, crystals were observed on day10 at the following pH6.8 to pH 7.4 in 0.1 pH unit increment, pH7.6 to pH8 with 0.1 pH unit increments and at pH 8.2 with crystal morphology of hexagonal blocks.

Wizard IV #31 was expanded by screening the concentration range of Polyacrylic acid 5100 from 5% to 30% in 5% increments and from 15% to 20% in 1% increments. Antibody, 21B12, crystals were observed for 15% Polyacrylic acid 5100 on day1 and were observed at 19% and 20% on day 10 with crystal morphology of hexagonal blocks.

PegIon HT #73 (0.1M Sodium Acetate Trihydrate pH7.0, 12% (w/v) PEG3350):

PegIon HT #73 was expanded by screening PEG3350 concentrations from 4% to 24% in 4% increments. Antibody, 21B12, crystals were observed on day1 at 8% PEG3350. The crystal morphology was leaves.

PegIon HT #73 was expanded by screening the sodium acetate trihydrate concentration from 0.1M to 1.35M in 0.25M increments. No crystals were observed.

Wizard Precipitant Synergy I #42 (1.65% (w/v) PEG400, 0.66M Ammonium Citrate/Citric Acid pH7.5):

Wizard Precipitant Synergy I #42 was expanded by screening Ammonium citrate/citric acid pH range (pH 4.5, 5.5, 7.5 and 8.5) as well as Ammonium citrate/citric acid concentration range from 0.1M to 1.1M in 0.2M increments. No crystals were observed in either of the expansions.

Wizard Precipitant Synergy I #54 (0.66M Lithium Sulfate, 0.66% (v/v) PEG 400, 0.1M Tris Hcl pH8.5):

Wizard Precipitant Synergy I #54 was expanded by screening Lithium sulfate concentration from 0.1M to 1.25M in 0.15 increments. Antibody, 21B12, crystals were observed at 0.55M, 0.65M and 0.7M on day1 and day3 respectively with crystal morphology of hexagonal blocks.

Wizard precipitant Synergy I #54 was expanded by screening in Tris Stock Options Kit (HR2-100) from pH 7.0 to pH 9.0 in 0.1 pH increments. Antibody, 21B12, crystals were observed at day 1 at the following pH units: pH 8.0 to 8.6 in 0.1 pH unit increments, pH 8.8 and pH8.9 with crystal morphology of hexagonal blocks or rods. Antibody, 21B12, crystals were observed on day 6 at the following pH units: pH 7.0, 7.1, 7.8 and 9.0 with crystal morphology of hexagonal blocks or rods.

Example 3—Batch Crystallization and % Yield

A. Antibody 21B12, (70 mg/ml) in 10 mM sodium acetate, 9% sucrose, pH5.2 was batch crystallized in 1.5 ml centrifuge tubes with a final volume of 100 ul. Antibody 21B12 consisted of two mature heavy chains (SEQ ID NO:19) and two mature light chains (SEQ ID NO:17) recombinantly produced by DNA encoding each of these chains. Equal amounts of Antibody, 21B12, and crystal growth condition as described in Table 3.1 was added in the 1.5 ml centrifuge tube, vortexed and stored at room temperature. Antibody, 21B12, batch crystallized on day 1 for the following crystal hits: LISS7 (0.05M Citric acid pH 5.5, 8% PEG3350), LISS7 (0.05M citric acid p H5.5, 12% PEG3350), Wizard I #32 (20% (w/v) Polyacrylic acid 5100, HEPES pH7.0, 20 mM Magnesium chloride), PEGIon HT #73 (0.1M Sodium Acetate trihydrate pH7.0, 12% (w/v) PEG3350). Antibody, 21B12, crystal morphology resembled leaves in all of the batch crystallization experiments.

TABLE 3.1

| Antibody 21B12 in | Batch vol | Day 0 | Day 1 | Day 2 | Day 3 | Day 4 | Day 7 | Day 8 | Day 9 | Day 10 | Day 11 |
|---|---|---|---|---|---|---|---|---|---|---|---|
| LISS7 (0.05M Citric acid pH 5.5, 4% PEG3350) | 110 ul | – | – | + | + | + | + | + | + | + | + |
| LISS7 (0.05M Citric acid pH 5.5, 8% PEG3350) | 110 ul | Light ppt | + | + | + | + | + | + | + | + | + |
| LISS7 (0.05M Citric acid pH 5.5, 12% PEG3350) | 110 ul | Heavy ppt | Clear, Gel | + | + | + | + | + | + | + | + |
| Index36 | 100 ul | – | – | – | – | – | – | – | – | – | – |
| Wizard I 13 | 100 ul | – | – | – | – | – | – | – | – | – | – |
| Wizard I 32 | 100 ul | – | + | + | + | + | + | + | + | + | + |
| Wizard II 15 | 100 ul | – | – | – | – | – | – | – | – | – | – |
| Wizard II 45 | 100 ul | – | – | – | – | – | – | – | – | – | – |

TABLE 3.1-continued

| Antibody 21B12 in | Batch vol | Day 0 | Day 1 | Day 2 | Day 3 | Day 6 | Day 7 | Day 8 | Day 9 | Day 10 |
|---|---|---|---|---|---|---|---|---|---|---|
| Wizard IV 13 | 100 ul | – | – | – | – | – | – | – | – | – |
| Wizard IV 31 | 100 ul | – | – | – | – | – | – | – | – | – |
| Crystal Screen HT #48 | 100 ul | – | – | – | – | – | – | – | – | – |
| PegIon HT #73 | 100 ul | Biphasic/Gel | + | + | + | + | + | + | + | + |

The symbol "–" means "clear", and the symbol "+" means "crystals".

B. Antibody 21B12 (70 mg/ml) in 10 mM sodium acetate, 9% sucrose, pH5.2 was batch crystallized in glass vials with mini stir bars at room temperature with a stirring speed of 250-450 rpm, as well as maximum speed on manual stir plate which could translate in to 550-800 rpm speeds, to a final volume of 1 ml (conditions as described in Table 3.2). More batch crystallization hits were observed with Antibody 21B12 with stirring as compared to the previous batch crystallization with no stirring. The crystal slurries generated via this technique were homogenous and the crystal size was <50 um by visual inspection via a microscope though settling was clearly observed overnight. Antibody 21B12 consisted of two mature heavy chains (SEQ ID NO:19) and two mature light chains (SEQ ID NO:17) recombinantly produced by DNA encoding each of these chains.

Antibody 21B12 batch crystallized at day 1 for the following crystal hits: LISS7 (0.05M citric acid pH5.5, 12% PEG3350); Wizard I #32 (20% (w/v) Polyacrylic acid 5100 HEPES pH7.0, 20 mM Magnesium chloride); Wizard II #15(1.26M (NH4)2So4, 0.1M HEPES pH 7.5; Wizard IV #13 and Wizard JCSG #67 (800 mM Succinic acid pH7.0); Crystal Screen HT #48 (0.1M Tris HCl pH8.5, 2M Ammonium phosphate monobasic); PEG Ion HT #73 (0.01M Sodium acetate trihydrate pH7.0, 12% (w/v) PEG3350); Wizard Precipitant synergy I #42 (1.65% (v/v) PEG400, 0.66M Ammonium citrate/citric acid pH7.5); Wizard Precipitant Synergy II #83 (0.34% (w/v) PEG4000, 0.67 Potassium phosphate dibasic/sodium phosphate); Wizard Precipitant Synergy II #88 (2% (w/v) PEG8000, 0.5M Ammonium citrate/Ammonium hydroxide pH8.5); and PEGIon HT #73 (0.1M Sodium Acetate trihydrate pH7.0, 12% (w/v) PEG3350).

TABLE 3.2

| Crystal Screens | Crystal Conditions | Starting [ ] mg/ml | A280 nm | Protein in crystalline form mg/ml | % Yield at day 12 | Observations |
|---|---|---|---|---|---|---|
| Low Ionic Strength Screen (LISS) | #7 (0.05M Citric acid pH 5.5 12% PEG 3350) (4 mg/ml antibody was used for this screening) | 120 | 4.216 | 115.784 | 96.5 | Crystalline under microscope |
| Index Screen | # 31 (0.8M Potassium Na tartarate tetrahydrate, 0.1M Tris pH 8.5, 0.5% w/v PEG MME 5000) | 120 | 58.09 | 61.91 | 51.6 | Opalescent but no crystals |
| Wizard I | # 13 (1.26M (NH4)2SO4, 0.1M cacodylate pH 6.5) | 120 | 59.679 | 60.321 | 50.3 | Opalescent but no crystals |
| | #32 (10% (w/v) PEG 3000, 0.1M Na/K Phosphate pH 6.2 ) | 120 | 16.361 | 103.639 | 86.4 | Crystalline under microscope |
| Wizard II | #15 (1.26M (NH4)2SO4, 0.1M HEPES pH 7.5) | 120 | 61.508 | 58.492 | 48.7 | Crystalline under microscope |
| | # 45 (1.26M (NH4)2SO4, 0.1M MES pH 6.0) | 120 | 61.172 | 58.828 | 49.0 | Opalescent but no crystals |
| Wizard IV | #13 (800 mM Succinic Acid pH 7.0) | 120 | 54.635 | 65.365 | 54.5 | Crystalline under microscope |
| | #31(20% (w/v) Polyacrylic acid 5100, HEPES pH 7.0, 20 mM Magnesium chloride) | 120 | n/a | n/a | n/a | Gelated |
| Crystal Screen HT | #48(D12) 0.1M Tris HCl pH 8.5, 2.0M Ammonium phosphate monobasic | 120 | 75.526 | 44.474 | 37.1 | Crystalline under microscope |

TABLE 3.2-continued

| Crystal Screens | Crystal Conditions | Starting [ ] mg/ml | A280 nm | Protein in crystalline form mg/ml | % Yield at day 12 | Observations |
|---|---|---|---|---|---|---|
| Peg/Ion HT | #73 (0.1M Sodium acetate trihydrate pH 7.0, 12% (w/v) Polyethylene glycol 3350) | 120 | 21.84 | 98.16 | 81.8 | Crystalline under microscope |
| Wizard Precipitant Synergy I | #54 (0.66M Lithium sulfate, 0.66% (v/v) PEG400, 0.1M Tris HCl pH 8.5) | 120 | 62.721 | 57.279 | 47.7 | Opalescent but no crystals |
| | #2 (1.34M Ammonium sulfate, 1.34% (v/v) PEG400, 0.1M Sodium acetate/Acetic acid pH 5.5) | 120 | n/a | n/a | n/a | Clear |
| | #42 (1.65% (v/v) PEG 400, 0.66M Ammonium citrate/citric acid pH 7.5) | 120 | 52.881 | 67.119 | 55.9 | Crystalline under microscope |
| Wizard Precipitant Synergy II | #83 (0.34% (w/v)PEG 4000, 0.67M Potassium phosphate dibasic/Sodium phosphate monobasic pH 7.5) | 120 | 58.117 | 61.883 | 51.6 | Crystalline under microscope |
| | #88 (2% (w/v) PEG 8000, 0.5M Ammonium citrate/ Ammonium hydroxide pH 8.5) | 120 | 57.249 | 62.751 | 52.3 | Crystalline under microscope |
| Wizard JCSG | #67 (800 mM Succinic acid pH 7.0) | 120 | n/a | n/a | n/a | condtition same as Wizard IV #13 |
| | #71 (1000 mM Succinic acid pH 7.0, 100 mM HEPES free acid/Sodium hydroxide pH 7.0, 1% (w/v) PEG 2000 MME) | 120 | n/a | n/a | n/a | n/a |

C. Antibody 21B12 (120 mg/ml) in 10 mM sodium acetate, 220 mM proline, 0.010% polysorbate 80, pH5.0 was batch crystallized in glass vials with mini stir bars at room temperature with a stirring speed of 250-450 rpm, as well as maximum speed on manual stir plate which could translate in to 550-800 rpm speeds, to a final volume of 1 ml. Antibody 21B12 consisted of two mature heavy chains (SEQ ID NO:19) and two mature light chains (SEQ ID NO:17) recombinantly produced by DNA encoding each of these chains.

Antibody 21B12 in 10 mM sodium acetate, 220 mM proline, 0.010% polysorbate 80, pH5.0 batch crystallized at day 1 using PEGIon HT (0.1M sodium acetate trihydrate pH7.0, 12% (w/v) polyethylene glycol 3350).

D. Antibody 21B12 (190 mg/ml) in 200 mM n-acetyl L-arginine, 10 mM glutamate, pH5.2 was batch crystallized in glass vials with mini stir bars at room temperature with a stirring speed of 250-450 rpm, as well as maximum speed on manual stir plate which could translate in to 550-800 rpm speeds, to a final volume of 1 ml. Antibody 21B12 consisted of two mature heavy chains (SEQ ID NO:19) and two mature light chains (SEQ ID NO:17) recombinantly produced by DNA encoding each of these chains.

Antibody 21B12 batch crystallized at day 1 using modified PEGIon HT (0.05 M sodium acetate trihydrate pH7.0, 12% (w/v) polyethylene glycol 3350).

Example 4—Creation of Isotonic Injectable Conditions

The ingredients for the PEGIon HT #73 conditions as described in Example 3 above are injectable in humans, however, the osmolality for this condition is hypertonic measuring 457 mOsm/kg using Advanced Instruments model 3900 by TA instruments. Since the acceptable Osmolality range for an isotonic injectable drug is between about 250-350 mOsm/kg, conditions were explored to identify conditions in the appropriate osmolality range. Antibody 21B12 was batch crystallized in glass vial with mini stir bars at room temperature with a stirring speed of 250-450 rpm using the conditions as described in Table 4.1 to a final volume of 1 ml. The sample volume used for measuring osmolality was 250 ul. The osmolality range is 250-350 mOsm/kg.

0.05M Sodium acetate trihydrate pH7.0, with 11% to 13% PEG3350 is isotonic and injectable. 0.6M and 0.07M sodium acetate trihydrate pH7.0, 12% PEG3350 is also isotonic and injectable. The yield for 0.05M Sodium acetate trihydrate pH7.0, 12% PEG3350 was 79%. Antibody 21B12 was scaled up in the condition from 1 ml to 50 mls on a bench scale at room temperature at a 1:1 ratio of protein: crystal growth solution.

TABLE 4.1

| Crystal Conditions | Osmolality |
| --- | --- |
| 0.05M Sodium acetate trihydrate, 8% PEG3350 | 176 mOsm/kg |
| 0.05M Sodium acetate trihydrate, 9% PEG3350 | 198 mOms/kg |
| 0.05M Sodium acetate trihydrate, 10% PEG3350 | 220 mOms/kg |
| 0.05M Sodium acetate trihydrate, 11% PEG3350 | 256 mOms/kg |
| 0.05M Sodium acetate trihydrate, 12% PEG3350 | 305 mOms/kg |
| 0.05M Sodium acetate trihydrate, 13% PEG3350 | 321 mOms/kg |
| 0.06M Sodium acetate trihydrate, 12% PEG33500 | 317 mOsm/kg |
| 0.07M Sodium acetate trihydrate, 12% PEG3350 | 325 mOsm/kg |
| 0.08M Sodium acetate trihydrate, 12% PEG3350 | 382 mOsm/kg |
| 0.09M Sodium acetate trihydrate, 12% PEG3350 | 396 mOsm/kg |

0.05M Sodium acetate trihydrate pH7.0, with 11% to 13% PEG3350 was isotonic and injectable, as was 0.6M and 0.07M Sodium acetate trihydrate pH7.0, 12% PEG3350. The yield for 0.05M Sodium acetate trihydrate pH7.0, 12% PEG3350 was 79%. Antibody 21B12 was scaled up in the condition from 1 ml to 50 mls on a bench scale at room temperature at a 1:1 ratio of protein:crystal growth solution.

Example 5—Assaying Protein Content of Antibody, 21B12, Crystals

Salts are often present in the sample or countersolvent, and these salts may form crystals during crystallization attempts. One popular method of distinguishing the growth of salt crystals from the target crystals of interest is through exposure to a staining dye such as IZIT™, manufactured by Hampton Research of Laguna Niguel, Calif. The IZIT™ dye stains protein crystals blue, but does not stain salt crystals.

Numerous modifications and variations in the practice of the invention are expected to occur to those of skill in the art upon consideration of the presently preferred embodiments thereof. Consequently, the only limitations which should be placed upon the scope of the invention are those which appear in the appended claims.

All of the U.S. patents, U.S. patent application publications, U.S. patent applications, foreign patents, foreign patent applications and non-patent publications referred to in this specification and/or listed in the Application Data Sheet, are incorporated herein by reference, in their entireties.

From the foregoing it will be appreciated that, although specific embodiments of the invention have been described herein for purposes of illustration, various modifications may be made without deviating from the spirit and scope of the invention.

What is claimed is:

1. A crystal comprising a substantially intact anti-PCSK9 IgG antibody comprising light chain complementarity determining region (CDR) of a CDRL1 sequence of SEQ ID NO:24, a CDRL2 sequence of SEQ ID NO:25, and a CDRL3 sequence of SEQ ID NO:26, and a heavy chain complementarity determining region (CDR) of the CDRH1 sequence of SEQ ID NOs:20 or 21, a CDRH2 sequence of SEQ ID NO:22, and a CDRH3 sequence of SEQ ID NO:23.

2. The crystal of claim 1, wherein the anti-PCSK9 IgG antibody comprises a light chain variable region that has the sequence of SEQ ID NO:9 or SEQ ID NO:11 and a heavy chain variable region that has the sequence of SEQ ID NO:5 or SEQ ID NO:7.

3. The crystal of claim 2, wherein the anti-PCSK9 IgG antibody comprises a light chain variable region having the amino acid sequence set forth in SEQ ID NO:9 or SEQ ID NO:11 and a heavy chain variable region comprising the amino acid sequence set forth in SEQ ID NO:5 or SEQ ID NO:7.

4. The crystal of claim 1, wherein the crystal has a length of about 100 μm to about 500 μm.

5. The crystal of claim 1 wherein the crystal has a hexagonal rod or block shape.

6. The crystal of claim 1, wherein the crystal comprises a salt selected from the group consisting of sodium dihydrogen phosphate, di-potassium hydrogen phosphate, sodium chloride, ammonium sulfate, potassium sodium tartrate tetrahydrate, tacsimate, sodium citrate dihydrate, sodium acetate trihydrate, di-ammonium tartrate, sodium malonate, acetate, calcium acetate, cacodylate, CHES, lithium sulfate, magnesium chloride, zinc acetate, cesium chloride, ammonium phosphate, sodium phosphate, potassium phosphate, sodium fluoride, potassium iodide, sodium idodide, ammonium iodide, sodium thiocyanate, potassium thiocyanate, sodium formate, potassium formate, and ammonium formate.

7. A method of making a crystal consisting essentially of a substantially intact anti-PCSK9 IgG antibody, comprising combining a solution of the antibody with a crystallization reagent comprising a salt selected from the group consisting of sodium dihydrogen phosphate, di-potassium hydrogen phosphate, sodium chloride, ammonium sulfate, potassium sodium tartrate tetrahydrate, tacsimate, sodium citrate dihydrate, sodium acetate trihydrate, di-ammonium tartrate, sodium malonate, acetate, calcium acetate, cacodylate, CHES, lithium sulfate, magnesium chloride, zin acetate, cesium chloride, ammonium phosphate, sodium phosphate, potassium phosphate, sodium fluoride, potassium iodide, sodium idodide, ammonium iodide, sodium thiocyanate, potassium thiocyanate, sodium formate, potassium formate, and ammonium formate in a crystallization buffer, optionally at pH of about 6 to about 8, wherein the substantially intact anti-PCSK9 IgG antibody comprises anti-PCSK9 antibody
   a light chain complementarity determining region of the CDRL1 sequence of SEQ ID NO:24, the CDRL2 sequence of SEQ ID NO:25, the CDRL3 sequence of SEQ ID NO:26, and the heavy chain complementarity determining region (CDR) of the CDRH1 sequence of SEQ ID NO:20 or SEQ ID NO:21, the CDRH2 sequence of SEQ ID NO:22, and the CDRH3 sequence of SEQ ID NO:23.

8. The method of claim 7, wherein the concentration of salt in the crystallization buffer is from about 0.1M to about 10M.

9. The method of claim 7, wherein the crystallization buffer further comprises 2-methyl-2,4-pentanediol (MPD) or polyethylene glycol (PEG).

10. The method of claim 9, wherein the MPD is present at a concentration of about 0.1% to about 50%.

11. The method of claim 9, wherein the PEG has a molecular weight of about 400 kDa to about 20,000 kDa.

12. The method of claim 11, wherein the PEG is present at a concentration of about 0.1% to about 50%.

13. The method of claim 7, further comprising removing at least a portion of the crystallization buffer after crystals have formed.

14. The method of claim 13, wherein the portion of crystallization buffer is removed by centrifugation.

15. The method of claim 13, wherein the crystals are placed in a solution comprising an organic additive.

16. The method of claim 15, further comprising the addition of an excipient to the solution.

17. The method of claim 16, wherein the excipient is selected from the group consisting of sucrose, trehalose, and sorbitol.

18. The method of claim 15, wherein the organic additive is ethanol or isopropanol.

19. The method of claim 7, further comprising drying crystals that have formed.

20. The method of claim 19, wherein the crystals are dried by exposure to air, or by exposure to a vacuum, or by exposure to nitrogen gas.

21. An antibody crystal produced by the method of claim 7.

22. A crystalline formulation of the antibody of claim 1.

23. A crystalline formulation of the antibody claim 22 at a protein concentration of 100 mg/ml or greater.

24. The crystalline formulation of claim 22, wherein the crystal comprises a salt selected from the group consisting of sodium dihydrogen phosphate, di-potassium hydrogen phosphate, sodium chloride, ammonium sulfate, potassium sodium tartrate tetrahydrate, tacsimate, sodium citrate dihydrate, sodium acetate trihydrate, di-ammonium tartrate, sodium malonate, acetate, calcium acetate, cacodylate, CHES, lithium sulfate, magnesium chloride, zinc acetate, cesium chloride, ammonium phosphate, sodium phosphate, potassium phosphate, sodium fluoride, potassium iodide, sodium idodide, ammonium iodide, sodium thiocyanate, potassium thiocyanate, sodium formate, potassium formate, and ammonium formate.

25. The crystalline formulation of claim 24, wherein the crystals have a length of about 20 μm to about 1 mm and a morphology of hexagonal rod shapes or block shapes, or a mixture thereof.

26. The crystalline formulation of claim 1 comprising at least 20% PEG3350 precipitant.

27. The crystalline formulation of claim 26, wherein the osmolality of the formulation ranges from about 180 to about 420 mOsm/kg.

28. A container comprising at least 100 to about 450 mg or more of the crystals of claim 1 for reconstitution in a volume of 0.5-2 mL.

29. A container comprising the crystalline formulation of claim 23.

30. The container of any one of claims 28-29, wherein the container is a vial, syringe or injection device.

31. A method of reconstituting the crystalline formulation of claim 22, comprising contacting the formulation with about 0.5-2 mL of sterile diluent.

32. A method of lowering serum LDL cholesterol or treating a disorder associated with increased levels of serum LDL cholesterol in a mammalian subject in need thereof comprising administering a crystal comprising a substantially intact anti-PCSK9 IgG antibody comprising light chain complementarity determining region (CDR) of a CDRL1 sequence of SEQ ID NO:24, a CDRL2 sequence of SEQ ID NO:25, and a CDRL3 sequence of SEQ ID NO:26, and a heavy chain complementarity determining region (CDR) of the CDRH1 sequence of SEQ ID NOs:20 or 21, a CDRH2 sequence of SEQ ID NO:22, and a CDRH3 sequence of SEQ ID NO:23 in an amount effective to lower serum LDL cholesterol levels in the subject as compared to a predose serum LDL cholesterol level.

33. A method of lowering serum LDL cholesterol or treating a disorder associated with increased levels of serum LDL cholesterol in a mammalian subject in need thereof comprising administering a crystalline formulation of a substantially intact anti-PCSK9 IgG antibody comprising light chain complementarity determining region (CDR) of a CDRL1 sequence of SEQ ID NO:24, a CDRL2 sequence of SEQ ID NO:25, and a CDRL3 sequence of SEQ ID NO:26, and a heavy chain complementarity determining region (CDR) of the CDRH1 sequence of SEQ ID NOs:20 or 21, a CDRH2 sequence of SEQ ID NO:22, and a CDRH3 sequence of SEQ ID NO:23 in an amount effective to lower serum LDL cholesterol levels in the subject as compared to a predose serum LDL cholesterol level.

* * * * *

SEQUENCE LISTING

```
<160> NUMBER OF SEQ ID NOS: 26

<210> SEQ ID NO 1
<211> LENGTH: 662
<212> TYPE: PRT
<213> ORGANISM: Homo sapiens

<400> SEQUENCE: 1

Gln Glu Asp Glu Asp Gly Asp Tyr Glu Glu Leu Val Leu Ala Leu Arg
1               5                   10                  15

Ser Glu Glu Asp Gly Leu Ala Glu Ala Pro Glu His Gly Thr Thr Ala
            20                  25                  30

Thr Phe His Arg Cys Ala Lys Asp Pro Trp Arg Leu Pro Gly Thr Tyr
        35                  40                  45

Val Val Val Leu Lys Glu Glu Thr His Leu Ser Gln Ser Glu Arg Thr
    50                  55                  60

Ala Arg Arg Leu Gln Ala Gln Ala Ala Arg Arg Gly Tyr Leu Thr Lys
65                  70                  75                  80

Ile Leu His Val Phe His Gly Leu Leu Pro Gly Phe Leu Val Lys Met
                85                  90                  95

Ser Gly Asp Leu Leu Glu Leu Ala Leu Lys Leu Pro His Val Asp Tyr
            100                 105                 110

Ile Glu Glu Asp Ser Ser Val Phe Ala Gln Ser Ile Pro Trp Asn Leu
        115                 120                 125

Glu Arg Ile Thr Pro Pro Arg Tyr Arg Ala Asp Glu Tyr Gln Pro Pro
    130                 135                 140

Asp Gly Gly Ser Leu Val Glu Val Tyr Leu Leu Asp Thr Ser Ile Gln
145                 150                 155                 160

Ser Asp His Arg Glu Ile Glu Gly Arg Val Met Val Thr Asp Phe Glu
                165                 170                 175
```

-continued

```
Asn Val Pro Glu Glu Asp Gly Thr Arg Phe His Arg Gln Ala Ser Lys
            180                 185                 190

Cys Asp Ser His Gly Thr His Leu Ala Gly Val Val Ser Gly Arg Asp
        195                 200                 205

Ala Gly Val Ala Lys Gly Ala Ser Met Arg Ser Leu Arg Val Leu Asn
    210                 215                 220

Cys Gln Gly Lys Gly Thr Val Ser Gly Thr Leu Ile Gly Leu Glu Phe
225                 230                 235                 240

Ile Arg Lys Ser Gln Leu Val Gln Pro Gly Pro Leu Val Val Leu
                245                 250                 255

Leu Pro Leu Ala Gly Gly Tyr Ser Arg Val Leu Asn Ala Ala Cys Gln
        260                 265                 270

Arg Leu Ala Arg Ala Gly Val Val Leu Val Thr Ala Ala Gly Asn Phe
    275                 280                 285

Arg Asp Asp Ala Cys Leu Tyr Ser Pro Ala Ser Ala Pro Glu Val Ile
        290                 295                 300

Thr Val Gly Ala Thr Asn Ala Gln Asp Gln Pro Val Thr Leu Gly Thr
305                 310                 315                 320

Leu Gly Thr Asn Phe Gly Arg Cys Val Asp Leu Phe Ala Pro Gly Glu
                325                 330                 335

Asp Ile Ile Gly Ala Ser Ser Asp Cys Ser Thr Cys Phe Val Ser Gln
        340                 345                 350

Ser Gly Thr Ser Gln Ala Ala Ala His Val Ala Gly Ile Ala Ala Met
    355                 360                 365

Met Leu Ser Ala Glu Pro Glu Leu Thr Leu Ala Glu Leu Arg Gln Arg
370                 375                 380

Leu Ile His Phe Ser Ala Lys Asp Val Ile Asn Glu Ala Trp Phe Pro
385                 390                 395                 400

Glu Asp Gln Arg Val Leu Thr Pro Asn Leu Val Ala Ala Leu Pro Pro
                405                 410                 415

Ser Thr His Gly Ala Gly Trp Gln Leu Phe Cys Arg Thr Val Trp Ser
        420                 425                 430

Ala His Ser Gly Pro Thr Arg Met Ala Thr Ala Ile Ala Arg Cys Ala
    435                 440                 445

Pro Asp Glu Glu Leu Leu Ser Cys Ser Ser Phe Ser Arg Ser Gly Lys
450                 455                 460

Arg Arg Gly Glu Arg Met Glu Ala Gln Gly Gly Lys Leu Val Cys Arg
465                 470                 475                 480

Ala His Asn Ala Phe Gly Gly Glu Gly Val Tyr Ala Ile Ala Arg Cys
                485                 490                 495

Cys Leu Leu Pro Gln Ala Asn Cys Ser Val His Thr Ala Pro Pro Ala
        500                 505                 510

Glu Ala Ser Met Gly Thr Arg Val His Cys His Gln Gln Gly His Val
    515                 520                 525

Leu Thr Gly Cys Ser Ser His Trp Glu Val Glu Asp Leu Gly Thr His
530                 535                 540

Lys Pro Pro Val Leu Arg Pro Arg Gly Gln Pro Asn Gln Cys Val Gly
545                 550                 555                 560

His Arg Glu Ala Ser Ile His Ala Ser Cys Cys His Ala Pro Gly Leu
                565                 570                 575

Glu Cys Lys Val Lys Glu His Gly Ile Pro Ala Pro Gln Gly Gln Val
        580                 585                 590

Thr Val Ala Cys Glu Glu Gly Trp Thr Leu Thr Gly Cys Ser Ala Leu
```

```
                595                 600                 605
    Pro Gly Thr Ser His Val Leu Gly Ala Tyr Ala Val Asp Asn Thr Cys
        610                 615                 620

Val Val Arg Ser Arg Asp Val Ser Thr Thr Gly Ser Thr Ser Glu Glu
    625                 630                 635                 640

Ala Val Thr Ala Val Ala Ile Cys Cys Arg Ser Arg His Leu Ala Gln
                    645                 650                 655

Ala Ser Gln Glu Leu Gln
                660

<210> SEQ ID NO 2
<211> LENGTH: 2076
<212> TYPE: DNA
<213> ORGANISM: Homo sapiens

<400> SEQUENCE: 2
atgggcaccg tcagctccag gcggtcctgg tggccgctgc cactgctgct gctgctgctg      60
ctgctcctgg gtcccgcggg cgcccgtgcg caggaggacg aggacggcga ctacgaggag     120
ctggtgctag ccttgcgctc cgaggaggac ggcctggccg aagcacccga gcacggaacc     180
acagccacct tccaccgctg cgccaaggat ccgtggaggt tgcctggcac ctacgtggtg     240
gtgctgaagg aggagaccca cctctcgcag tcagagcgca ctgcccgccc cctgcaggcc     300
caggctgccc gccggggata cctcaccaag atcctgcatg tcttccatgg ccttcttcct     360
ggcttcctgg tgaagatgag tggcgacctg ctggagctgg ccttgaagtt gccccatgtc     420
gactacatcg aggaggactc ctctgtcttt gcccagagca tcccgtggaa cctggagcgg     480
attacccctc gcggtaccgg gcggatgaa taccagcccc cgacggagg cagcctggtg       540 gaggtgtatc tcctagacac cagcatacag agtgaccacc gggaaatcga gggcagggtc     600
atggtcaccg acttcgagaa tgtgcccgag gaggacggga cccgcttcca cagacaggcc     660
agcaagtgtg acagtcatgg cacccacctg cagggggtgg tcagcggccg ggatgccggc     720
gtggccaagg gtgccagcat cgcagcctg cgcgtgctca actgccaagg aagggcacg      780 gttagcggca ccctcatagg cctggagttt attcggaaaa gccagctggt ccagcctgtg     840
gggccactgg tggtgctgct gcccctggcg ggtgggtaca gccgcgtcct caacgccgcc     900
tgccagcgcc tggcgagggc tggggtcgtg ctggtcaccg ctgccggcaa cttccgggac     960
gatgcctgcc tctactcccc agcctcagct cccgaggtca tcacagttgg ggccaccaat    1020
gcccaggacc agccggtgac cctggggact tggggaccca ctttggccg ctgtgtggac     1080 ctctttgccc caggggagga catcattggt gcctccagcg actgcagcac ctgctttgtg    1140
tcacagagtg ggacatcaca ggctgctgcc acgtggctg gcattgcagc catgatgctg    1200
tctgccgagc cggagctcac cctggccgag ttgaggcaga actgatcca cttctctgcc     1260 aaagatgtca tcaatgaggc ctggttccct gaggaccagc gggtactgac ccccaacctg     1320
gtggccgccc tgccccccag cacccatggg gcaggttggc agctgttttg caggactgtg     1380
tggtcagcac actcggggcc tacacggatg ccacagcca tcgcccgctg cgccccagat      1440
gaggagctgc tgagctgctc cagtttctcc aggagtggga gcggcgggg cgagcgcatg     1500 gaggcccaag ggggcaagct ggtctgccgg gcccacaacg cttttggggg tgagggtgtc     1560
tacgccattg ccaggtgctg cctgctaccc caggccaact gcagcgtcca cacagctcca    1620
ccagctgagg ccagcatggg gacccgtgtc cactgccacc aacagggcca cgtcctcaca    1680
ggctgcagct cccactggga ggtggaggac cttggcaccc acaagccgcc tgtgctgagg    1740
```

-continued

```
ccacgaggtc agcccaacca gtgcgtgggc cacagggagg ccagcatcca cgcttcctgc      1800
tgccatgccc caggtctgga atgcaaagtc aaggagcatg gaatcccggc ccctcagggg      1860
caggtgaccg tggcctgcga ggagggctgg accctgactg gctgcagcgc cctccctggg      1920
acctcccacg tcctgggggc ctacgccgta gacaacacgt gtgtagtcag gagccgggac      1980
gtcagcacta caggcagcac cagcgaagag gccgtgacag ccgttgccat ctgctgccgg      2040
agccggcacc tggcgcaggc ctcccaggag ctccag                                2076
```

<210> SEQ ID NO 3
<211> LENGTH: 692
<212> TYPE: PRT
<213> ORGANISM: Homo sapiens

<400> SEQUENCE: 3

```
Met Gly Thr Val Ser Ser Arg Arg Ser Trp Trp Pro Leu Pro Leu Leu
1               5                   10                  15

Leu Leu Leu Leu Leu Leu Gly Pro Ala Gly Ala Arg Ala Gln Glu
        20                  25                  30

Asp Glu Asp Gly Asp Tyr Glu Glu Leu Val Leu Ala Leu Arg Ser Glu
    35                  40                  45

Glu Asp Gly Leu Ala Glu Ala Pro Glu His Gly Thr Thr Ala Thr Phe
50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
```

```
                305                 310                 315                 320
        Asp Ala Cys Leu Tyr Ser Pro Ala Ser Ala Pro Glu Val Ile Thr Val
                        325                 330                 335
        Gly Ala Thr Asn Ala Gln Asp Gln Pro Val Thr Leu Gly Thr Leu Gly
                        340                 345                 350
        Thr Asn Phe Gly Arg Cys Val Asp Leu Phe Ala Pro Gly Glu Asp Ile
                        355                 360                 365
        Ile Gly Ala Ser Ser Asp Cys Ser Thr Cys Phe Val Ser Gln Ser Gly
                        370                 375                 380
        Thr Ser Gln Ala Ala Ala His Val Ala Gly Ile Ala Ala Met Met Leu
        385                 390                 395                 400
        Ser Ala Glu Pro Glu Leu Thr Leu Ala Glu Leu Arg Gln Arg Leu Ile
                        405                 410                 415
        His Phe Ser Ala Lys Asp Val Ile Asn Glu Ala Trp Phe Pro Glu Asp
                        420                 425                 430
        Gln Arg Val Leu Thr Pro Asn Leu Val Ala Ala Leu Pro Pro Ser Thr
                        435                 440                 445
        His Gly Ala Gly Trp Gln Leu Phe Cys Arg Thr Val Trp Ser Ala His
                        450                 455                 460
        Ser Gly Pro Thr Arg Met Ala Thr Ala Ile Ala Arg Cys Ala Pro Asp
        465                 470                 475                 480
        Glu Glu Leu Leu Ser Cys Ser Ser Phe Ser Arg Ser Gly Lys Arg Arg
                        485                 490                 495
        Gly Glu Arg Met Glu Ala Gln Gly Gly Lys Leu Val Cys Arg Ala His
                        500                 505                 510
        Asn Ala Phe Gly Gly Glu Gly Val Tyr Ala Ile Ala Arg Cys Cys Leu
                        515                 520                 525
        Leu Pro Gln Ala Asn Cys Ser Val His Thr Ala Pro Pro Ala Glu Ala
                        530                 535                 540
        Ser Met Gly Thr Arg Val His Cys His Gln Gln Gly His Val Leu Thr
        545                 550                 555                 560
        Gly Cys Ser Ser His Trp Glu Val Glu Asp Leu Gly Thr His Lys Pro
                        565                 570                 575
        Pro Val Leu Arg Pro Arg Gly Gln Pro Asn Gln Cys Val Gly His Arg
                        580                 585                 590
        Glu Ala Ser Ile His Ala Ser Cys Cys His Ala Pro Gly Leu Glu Cys
                        595                 600                 605
        Lys Val Lys Glu His Gly Ile Pro Ala Pro Gln Gly Gln Val Thr Val
                        610                 615                 620
        Ala Cys Glu Glu Gly Trp Thr Leu Thr Gly Cys Ser Ala Leu Pro Gly
        625                 630                 635                 640
        Thr Ser His Val Leu Gly Ala Tyr Ala Val Asp Asn Thr Cys Val Val
                        645                 650                 655
        Arg Ser Arg Asp Val Ser Thr Thr Gly Ser Thr Ser Glu Glu Ala Val
                        660                 665                 670
        Thr Ala Val Ala Ile Cys Cys Arg Ser Arg His Leu Ala Gln Ala Ser
                        675                 680                 685
        Gln Glu Leu Gln
            690

<210> SEQ ID NO 4
<211> LENGTH: 345
<212> TYPE: DNA
<213> ORGANISM: Homo sapiens
```

<220> FEATURE:
<221> NAME/KEY: misc_feature
<223> OTHER INFORMATION: Nucleotide sequence of heavy chain variable
      region

<400> SEQUENCE: 4
caggttcagc tggtgcagtc tggagctgag gtgaagaagc ctggggcctc agtgaaggtc      60
tcctgcaagg cttctggtta caccttaacc agctatggta tcagctgggt gcgacaggcc    120
cctggacaag gcttgagtg gatgggatgg gtcagttttt ataatggtaa cacaaactat    180
gcacagaagc tccagggcag aggcaccatg accacagacc catccacgag cacagcctac    240
atggagctga ggagcctgag atctgacgac acggccgtgt attactgtgc gagaggctac    300
ggtatggacg tctggggcca aggaccacg gtcaccgtct cctct                     345

<210> SEQ ID NO 5
<211> LENGTH: 115
<212> TYPE: PRT
<213> ORGANISM: Homo sapiens
<220> FEATURE:
<221> NAME/KEY: MISC_FEATURE
<223> OTHER INFORMATION: Amino acid sequence of heavy chain variable
      region

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
                20                  25                  30

Gly Ile Ser Trp Val Arg Gln Ala Pro Gly Gln Gly Leu Glu Trp Met
            35                  40                  45

Gly Trp Val Ser Phe Tyr Asn Gly Asn Thr Asn Tyr Ala Gln Lys Leu
        50                  55                  60

Gln Gly Arg Gly Thr Met Thr Thr Asp Pro Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
            100                 105                 110

Val Ser Ser
        115

<210> SEQ ID NO 6
<211> LENGTH: 345
<212> TYPE: DNA
<213> ORGANISM: Homo sapiens
<220> FEATURE:
<221> NAME/KEY: misc_feature
<223> OTHER INFORMATION: Alternative Nucleotide sequence of heavy chain
      variable region

<400> SEQUENCE: 6
gaggttcagc tggtgcagtc tggagctgag gtgaagaagc ctggggcctc agtgaaggtc      60
tcctgcaagg cttctggtta caccttaacc agctatggta tcagctgggt gcgacaggcc    120
cctggacaag gcttgagtg gatgggatgg gtcagttttt ataatggtaa cacaaactat    180
gcacagaagc tccagggcag aggcaccatg accacagacc catccacgag cacagcctac    240
atggagctga ggagcctgag atctgacgac acggccgtgt attactgtgc gagaggctac    300
ggtatggacg tctggggcca aggaccacg gtcaccgtct cctct                     345

```
<210> SEQ ID NO 7
<211> LENGTH: 115
<212> TYPE: PRT
<213> ORGANISM: Homo sapiens
<220> FEATURE:
<221> NAME/KEY: MISC_FEATURE
<223> OTHER INFORMATION: Alternative Amino acid sequence of heavy chain
      variable region

<400> SEQUENCE: 7

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
            20                  25                  30

Gly Ile Ser Trp Val Arg Gln Ala Pro Gly Gln Gly Leu Glu Trp Met
        35                  40                  45

Gly Trp Val Ser Phe Tyr Asn Gly Asn Thr Asn Tyr Ala Gln Lys Leu
    50                  55                  60

Gln Gly Arg Gly Thr Met Thr Thr Asp Pro Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
            100                 105                 110

Val Ser Ser
        115

<210> SEQ ID NO 8
<211> LENGTH: 327
<212> TYPE: DNA
<213> ORGANISM: Homo sapiens
<220> FEATURE:
<221> NAME/KEY: misc_feature
<223> OTHER INFORMATION: Nucleotide sequence of light chain variable
      region

<400> SEQUENCE: 8
cagtctgccc tgactcagcc tgcctccgtg tctgggtctc ctggacagtc gatcaccatc       60
tcctgcactg gaaccagcag tgacgttggt ggttataact ctgtctcctg gtaccaacag      120
cacccaggca aagcccccaa actcatgatt tatgaggtca gtaatcggcc ctcagggggtt     180 tctaatcgct tctctggctc caagtctggc aacacggcct ccctgaccat ctctgggctc     240
caggctgagg acgaggctga ttattactgc aattcatata agcaccag catggtattc       300 ggcggaggga ccaagctgac cgtccta                                           327

<210> SEQ ID NO 9
<211> LENGTH: 109
<212> TYPE: PRT
<213> ORGANISM: Homo sapiens
<220> FEATURE:
<221> NAME/KEY: MISC_FEATURE
<223> OTHER INFORMATION: Amino acid sequence of light chain variable
      region

<400> SEQUENCE: 9

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
```

```
                35                  40                  45
Met Ile Tyr Glu Val Ser Asn Arg Pro Ser Gly Val Ser Asn Arg Phe
            50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Asn Ser Tyr Thr Ser Thr
                85                  90                  95

Ser Met Val Phe Gly Gly Gly Thr Lys Leu Thr Val Leu
            100                 105

<210> SEQ ID NO 10
<211> LENGTH: 327
<212> TYPE: DNA
<213> ORGANISM: Homo sapiens
<220> FEATURE:
<221> NAME/KEY: misc_feature
<223> OTHER INFORMATION: Alternative Nucleotide sequence of light chain
      variable region

<400> SEQUENCE: 10
gagtctgccc tgactcagcc tgcctccgtg tctgggtctc ctggacagtc gatcaccatc      60
tcctgcactg gaaccagcag tgacgttggt ggttataact ctgtctcctg gtaccaacag     120
cacccaggca agcccccaa actcatgatt tatgaggtca gtaatcggcc ctcaggggtt     180
tctaatcgct tctctggctc caagtctggc aacacggcct ccctgaccat ctctgggctc     240
caggctgagg acgaggctga ttattactgc aattcatata caagcaccag catggtattc     300
ggcggaggga ccaagctgac cgtccta                                         327

<210> SEQ ID NO 11
<211> LENGTH: 109
<212> TYPE: PRT
<213> ORGANISM: Homo sapiens
<220> FEATURE:
<221> NAME/KEY: MISC_FEATURE
<223> OTHER INFORMATION: Alternative Amino acid sequence of light chain
      variable region

<400> SEQUENCE: 11

Glu Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
            50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Asn Ser Tyr Thr Ser Thr
                85                  90                  95

Ser Met Val Phe Gly Gly Gly Thr Lys Leu Thr Val Leu
            100                 105

<210> SEQ ID NO 12
<211> LENGTH: 326
<212> TYPE: PRT
<213> ORGANISM: Homo sapiens
<220> FEATURE:
<221> NAME/KEY: MISC_FEATURE
<223> OTHER INFORMATION: Human IgG2
```

<400> SEQUENCE: 12

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 13
<211> LENGTH: 327
<212> TYPE: PRT
<213> ORGANISM: Homo sapiens
<220> FEATURE:
<221> NAME/KEY: MISC_FEATURE
<223> OTHER INFORMATION: Human IgG4

<400> SEQUENCE: 13

Ala Ser Thr Lys Gly Pro Ser Val Phe Pro Leu Ala Pro Cys Ser Arg
1               5                   10                  15

-continued

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 14
<211> LENGTH: 105
<212> TYPE: PRT
<213> ORGANISM: Homo sapiens
<220> FEATURE:
<221> NAME/KEY: MISC_FEATURE
<223> OTHER INFORMATION: Human lambda

<400> SEQUENCE: 14

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val

```
                35                  40                  45
Lys Ala Gly Val Glu Thr Thr Thr Pro Ser Lys Gln Ser Asn Asn Lys
        50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 15
<211> LENGTH: 106
<212> TYPE: PRT
<213> ORGANISM: Homo sapiens
<220> FEATURE:
<221> NAME/KEY: MISC_FEATURE
<223> OTHER INFORMATION: Human kappa

<400> SEQUENCE: 15

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 16
<211> LENGTH: 215
<212> TYPE: PRT
<213> ORGANISM: Homo sapiens
<220> FEATURE:
<221> NAME/KEY: MISC_FEATURE
<223> OTHER INFORMATION: 21B12 mature light chain

<400> SEQUENCE: 16

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Asn Ser Tyr Thr Ser Thr
                85                  90                  95

Ser Met Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
```

```
                    115                 120                 125
Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 17
<211> LENGTH: 215
<212> TYPE: PRT
<213> ORGANISM: Homo sapiens
<220> FEATURE:
<221> NAME/KEY: MISC_FEATURE
<223> OTHER INFORMATION: Alternative 21B12 mature light chain

<400> SEQUENCE: 17

Glu Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Asn Ser Tyr Thr Ser Thr
                85                  90                  95

Ser Met Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 18
<211> LENGTH: 441
<212> TYPE: PRT
<213> ORGANISM: Homo sapiens
<220> FEATURE:
```

<221> NAME/KEY: MISC_FEATURE
<223> OTHER INFORMATION: 21B12 mature heavy chain

<400> SEQUENCE: 18

| | | | | | | | | | | | | | | | |
|---|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ala |
| 1 | | | | 5 | | | | | 10 | | | | | 15 | |
| Ser | Val | Lys | Val | Ser | Cys | Lys | Ala | Ser | Gly | Tyr | Thr | Leu | Thr | Ser | Tyr |
| | | | 20 | | | | | 25 | | | | | 30 | | |
| Gly | Ile | Ser | Trp | Val | Arg | Gln | Ala | Pro | Gly | Gln | Gly | Leu | Glu | Trp | Met |
| | | 35 | | | | | 40 | | | | | 45 | | | |
| Gly | Trp | Val | Ser | Phe | Tyr | Asn | Gly | Asn | Thr | Asn | Tyr | Ala | Gln | Lys | Leu |
| | 50 | | | | | 55 | | | | | 60 | | | | |
| Gln | Gly | Arg | Gly | Thr | Met | Thr | Thr | Asp | Pro | Ser | Thr | Ser | Thr | Ala | Tyr |
| 65 | | | | | 70 | | | | | 75 | | | | | 80 |
| Met | Glu | Leu | Arg | Ser | Leu | Arg | Ser | Asp | Asp | Thr | Ala | Val | Tyr | Tyr | Cys |
| | | | | 85 | | | | | 90 | | | | | 95 | |
| Ala | Arg | Gly | Tyr | Gly | Met | Asp | Val | Trp | Gly | Gln | Gly | Thr | Thr | Val | Thr |
| | | | | 100 | | | | | 105 | | | | | 110 | |
| Val | Ser | Ser | Ala | Ser | Thr | Lys | Gly | Pro | Ser | Val | Phe | Pro | Leu | Ala | Pro |
| | | 115 | | | | | 120 | | | | | 125 | | | |
| Cys | Ser | Arg | Ser | Thr | Ser | Glu | Ser | Thr | Ala | Ala | Leu | Gly | Cys | Leu | Val |
| | 130 | | | | | 135 | | | | | 140 | | | | |
| Lys | Asp | Tyr | Phe | Pro | Glu | Pro | Val | Thr | Val | Ser | Trp | Asn | Ser | Gly | Ala |
| 145 | | | | | 150 | | | | | 155 | | | | | 160 |
| Leu | Thr | Ser | Gly | Val | His | Thr | Phe | Pro | Ala | Val | Leu | Gln | Ser | Ser | Gly |
| | | | | 165 | | | | | 170 | | | | | 175 | |
| Leu | Tyr | Ser | Leu | Ser | Ser | Val | Val | Thr | Val | Pro | Ser | Ser | Asn | Phe | Gly |
| | | | | 180 | | | | | 185 | | | | | 190 | |
| Thr | Gln | Thr | Tyr | Thr | Cys | Asn | Val | Asp | His | Lys | Pro | Ser | Asn | Thr | Lys |
| | | | 195 | | | | | 200 | | | | | 205 | | |
| Val | Asp | Lys | Thr | Val | Glu | Arg | Lys | Cys | Cys | Val | Glu | Cys | Pro | Pro | Cys |
| 210 | | | | | 215 | | | | | 220 | | | | | |
| Pro | Ala | Pro | Pro | Val | Ala | Gly | Pro | Ser | Val | Phe | Leu | Phe | Pro | Pro | Lys |
| 225 | | | | | 230 | | | | | 235 | | | | | 240 |
| Pro | Lys | Asp | Thr | Leu | Met | Ile | Ser | Arg | Thr | Pro | Glu | Val | Thr | Cys | Val |
| | | | | 245 | | | | | 250 | | | | | 255 | |
| Val | Val | Asp | Val | Ser | His | Glu | Asp | Pro | Glu | Val | Gln | Phe | Asn | Trp | Tyr |
| | | | 260 | | | | | 265 | | | | | 270 | | |
| Val | Asp | Gly | Val | Glu | Val | His | Asn | Ala | Lys | Thr | Lys | Pro | Arg | Glu | Glu |
| | | 275 | | | | | 280 | | | | | 285 | | | |
| Gln | Phe | Asn | Ser | Thr | Phe | Arg | Val | Val | Ser | Val | Leu | Thr | Val | Val | His |
| | 290 | | | | | 295 | | | | | 300 | | | | |
| Gln | Asp | Trp | Leu | Asn | Gly | Lys | Glu | Tyr | Lys | Cys | Lys | Val | Ser | Asn | Lys |
| 305 | | | | | 310 | | | | | 315 | | | | | 320 |
| Gly | Leu | Pro | Ala | Pro | Ile | Glu | Lys | Thr | Ile | Ser | Lys | Thr | Lys | Gly | Gln |
| | | | | 325 | | | | | 330 | | | | | 335 | |
| Pro | Arg | Glu | Pro | Gln | Val | Tyr | Thr | Leu | Pro | Pro | Ser | Arg | Glu | Glu | Met |
| | | | | 340 | | | | | 345 | | | | | 350 | |
| Thr | Lys | Asn | Gln | Val | Ser | Leu | Thr | Cys | Leu | Val | Lys | Gly | Phe | Tyr | Pro |
| | | | 355 | | | | | 360 | | | | | 365 | | |
| Ser | Asp | Ile | Ala | Val | Glu | Trp | Glu | Ser | Asn | Gly | Gln | Pro | Glu | Asn | Asn |
| | | 370 | | | | | 375 | | | | | 380 | | | |
| Tyr | Lys | Thr | Thr | Pro | Pro | Met | Leu | Asp | Ser | Asp | Gly | Ser | Phe | Phe | Leu |
| 385 | | | | | 390 | | | | | 395 | | | | | 400 |

Tyr Ser Lys Leu Thr Val Asp Lys Ser Arg Trp Gln Gln Gly Asn Val
            405                 410                 415

Phe Ser Cys Ser Val Met His Glu Ala Leu His Asn His Tyr Thr Gln
            420                 425                 430

Lys Ser Leu Ser Leu Ser Pro Gly Lys
            435                 440

<210> SEQ ID NO 19
<211> LENGTH: 441
<212> TYPE: PRT
<213> ORGANISM: Homo sapiens
<220> FEATURE:
<221> NAME/KEY: MISC_FEATURE
<223> OTHER INFORMATION: Alternative 21B12 mature heavy chain

<400> SEQUENCE: 19

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
            20                  25                  30

Gly Ile Ser Trp Val Arg Gln Ala Pro Gly Gln Gly Leu Glu Trp Met
            35                  40                  45

Gly Trp Val Ser Phe Tyr Asn Gly Asn Thr Asn Tyr Ala Gln Lys Leu
    50                  55                  60

Gln Gly Arg Gly Thr Met Thr Thr Asp Pro Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
            100                 105                 110

Val Ser Ser Ala Ser Thr Lys Gly Pro Ser Val Phe Pro Leu Ala Pro
            115                 120                 125

Cys Ser Arg Ser Thr Ser Glu Ser Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
            195                 200                 205

Val Asp Lys Thr Val Glu Arg Lys Cys Cys Val Glu Cys Pro Pro Cys
    210                 215                 220

Pro Ala Pro Pro Val Ala Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Gln Phe Asn Trp Tyr
            260                 265                 270

Val Asp Gly Val Glu Val His Asn Ala Lys Thr Lys Pro Arg Glu Glu
            275                 280                 285

Gln Phe Asn Ser Thr Phe Arg Val Val Ser Val Leu Thr Val Val His
    290                 295                 300

Gln Asp Trp Leu Asn Gly Lys Glu Tyr Lys Cys Lys Val Ser Asn Lys

```
                305                 310                 315                 320
Gly Leu Pro Ala Pro Ile Glu Lys Thr Ile Ser Lys Thr Lys Gly Gln
                    325                 330                 335

Pro Arg Glu Pro Gln Val Tyr Thr Leu Pro Pro Ser Arg Glu Glu Met
                340                 345                 350

Thr Lys Asn Gln Val Ser Leu Thr Cys Leu Val Lys Gly Phe Tyr Pro
            355                 360                 365

Ser Asp Ile Ala Val Glu Trp Glu Ser Asn Gly Gln Pro Glu Asn Asn
        370                 375                 380

Tyr Lys Thr Thr Pro Pro Met Leu Asp Ser Asp Gly Ser Phe Phe Leu
    385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
                420                 425                 430

Lys Ser Leu Ser Leu Ser Pro Gly Lys
            435                 440

<210> SEQ ID NO 20
<211> LENGTH: 5
<212> TYPE: PRT
<213> ORGANISM: Homo sapiens
<220> FEATURE:
<221> NAME/KEY: MISC_FEATURE
<223> OTHER INFORMATION: CDRH1

<400> SEQUENCE: 20

Ser Tyr Gly Ile Ser
1               5

<210> SEQ ID NO 21
<211> LENGTH: 10
<212> TYPE: PRT
<213> ORGANISM: Homo sapiens
<220> FEATURE:
<221> NAME/KEY: MISC_FEATURE
<223> OTHER INFORMATION: CDRH1

<400> SEQUENCE: 21

Gly Tyr Thr Leu Thr Ser Tyr Gly Ile Ser
1               5                   10

<210> SEQ ID NO 22
<211> LENGTH: 17
<212> TYPE: PRT
<213> ORGANISM: Homo sapiens
<220> FEATURE:
<221> NAME/KEY: MISC_FEATURE
<223> OTHER INFORMATION: CDRH2

<400> SEQUENCE: 22

Trp Val Ser Phe Tyr Asn Gly Asn Thr Asn Tyr Ala Gln Lys Leu Gln
1               5                   10                  15

Gly

<210> SEQ ID NO 23
<211> LENGTH: 6
<212> TYPE: PRT
<213> ORGANISM: Homo sapiens
<220> FEATURE:
<221> NAME/KEY: MISC_FEATURE
<223> OTHER INFORMATION: CDRH3
```

```
<400> SEQUENCE: 23

Gly Tyr Gly Met Asp Val
1               5

<210> SEQ ID NO 24
<211> LENGTH: 14
<212> TYPE: PRT
<213> ORGANISM: Homo sapiens
<220> FEATURE:
<221> NAME/KEY: MISC_FEATURE
<223> OTHER INFORMATION: CDRL1

<400> SEQUENCE: 24

Thr Gly Thr Ser Ser Asp Val Gly Gly Tyr Asn Ser Val Ser
1               5                   10

<210> SEQ ID NO 25
<211> LENGTH: 7
<212> TYPE: PRT
<213> ORGANISM: Homo sapiens
<220> FEATURE:
<221> NAME/KEY: MISC_FEATURE
<223> OTHER INFORMATION: CDRL2

<400> SEQUENCE: 25

Glu Val Ser Asn Arg Pro Ser
1               5

<210> SEQ ID NO 26
<211> LENGTH: 9
<212> TYPE: PRT
<213> ORGANISM: Homo sapiens
<220> FEATURE:
<221> NAME/KEY: MISC_FEATURE
<223> OTHER INFORMATION: CDRL3

<400> SEQUENCE: 26

Asn Ser Tyr Thr Ser Thr Ser Met Val
1               5
```